US008523765B2

(12) United States Patent
Kawai

(10) Patent No.: US 8,523,765 B2
(45) Date of Patent: Sep. 3, 2013

(54) MEDICAL CONTROL APPARATUS

(75) Inventor: Toshimasa Kawai, Yokohama (JP)

(73) Assignee: Olympus Medical Systems Corp., Tokyo (JP)

(*) Notice: Subject to any disclaimer, the term of this patent is extended or adjusted under 35 U.S.C. 154(b) by 601 days.

(21) Appl. No.: 12/019,375

(22) Filed: Jan. 24, 2008

(65) Prior Publication Data
US 2008/0221592 A1 Sep. 11, 2008

Related U.S. Application Data

(63) Continuation of application No. PCT/JP2006/314398, filed on Jul. 20, 2006.

(30) Foreign Application Priority Data

Jul. 25, 2005 (JP) .................................. 2005-214726
Jul. 25, 2005 (JP) .................................. 2005-214727
Jul. 25, 2005 (JP) .................................. 2005-214728
Jul. 25, 2005 (JP) .................................. 2005-214729

(51) Int. Cl.
*A61B 1/00* (2006.01)
*G05B 15/00* (2006.01)

(52) U.S. Cl.
USPC ............ 600/141; 600/117; 600/145; 600/146

(58) Field of Classification Search
USPC ......... 600/141–150, 114, 117, 118; 700/245, 700/262
See application file for complete search history.

(56) References Cited

U.S. PATENT DOCUMENTS

| 4,930,494 | A | * | 6/1990 | Takehana et al. ............. 600/145 |
| 4,999,553 | A | * | 3/1991 | Seraji ............................ 700/245 |
| 5,159,249 | A | * | 10/1992 | Megherbi .................... 318/568.1 |
| 5,429,132 | A | * | 7/1995 | Guy et al. ...................... 600/422 |

(Continued)

FOREIGN PATENT DOCUMENTS

| JP | 2845255 | 10/1998 |
| JP | 2917263 | 4/1999 |
| JP | 2004-283618 | 10/2004 |
| JP | 2005-126843 | 5/2005 |

OTHER PUBLICATIONS

Supplementary European Search Report for European Patent Application No. 06 76 8326, mailed Feb. 2, 2011.

(Continued)

*Primary Examiner* — Katherine Dowe
*Assistant Examiner* — Aaron B Fairchild
(74) *Attorney, Agent, or Firm* — Scully, Scott, Murphy & Presser, P.C.

(57) ABSTRACT

A controller includes a servo controller that performs attitude control of the bending portion. A point lock computing section is provided at the servo controller. Based on supplied distal end command value information and position feedback information, the point lock computing section performs computational processing by a distal end link root coordinate position calculating section and an inverse kinematics computing section in order to obtain a servo position command signal for a distal end-side link member and a servo position command signal for a link member other than the link member, and outputs the same to a driving section. Accordingly, point lock is enabled at two locations, namely, the distal end-side link member and an arbitrary link member, while other link members are controlled so as to assume attitudes having redundancy.

12 Claims, 52 Drawing Sheets

(56) References Cited

U.S. PATENT DOCUMENTS

| | | |
|---|---|---|
| 6,743,239 B1 * | 6/2004 | Kuehn et al. .................. 606/139 |
| 2003/0191367 A1 * | 10/2003 | Belson et al. ................. 600/146 |
| 2004/0193014 A1 | 9/2004 | Miyagi et al. |
| 2005/0119527 A1 | 6/2005 | Banik et al. |
| 2005/0154261 A1 * | 7/2005 | Ohline et al. ................. 600/141 |
| 2006/0041188 A1 * | 2/2006 | Dirusso et al. ............... 600/146 |
| 2006/0069310 A1 * | 3/2006 | Couvillon, Jr. ............... 600/148 |
| 2006/0178562 A1 * | 8/2006 | Saadat et al. .................. 600/142 |
| 2009/0171151 A1 * | 7/2009 | Choset et al. ................. 600/114 |

OTHER PUBLICATIONS

English-language abstract only of Japanese Patent Application Publication No. 06-217925 dated Aug. 9, 1994.

English-language abstract only of Japanese Patent Application Publication No. 06-217926 dated Aug. 9, 1994.

* cited by examiner

LINEAR FUNCTION

QUADRATIC FUNCTION s: LAPLACE OPERATOR
P: EXTREMUM (ZERO POINT)

FIG.88
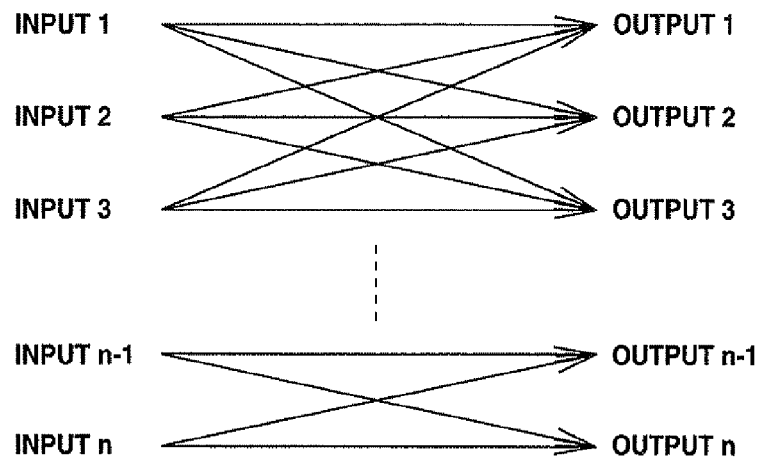
FIG.89
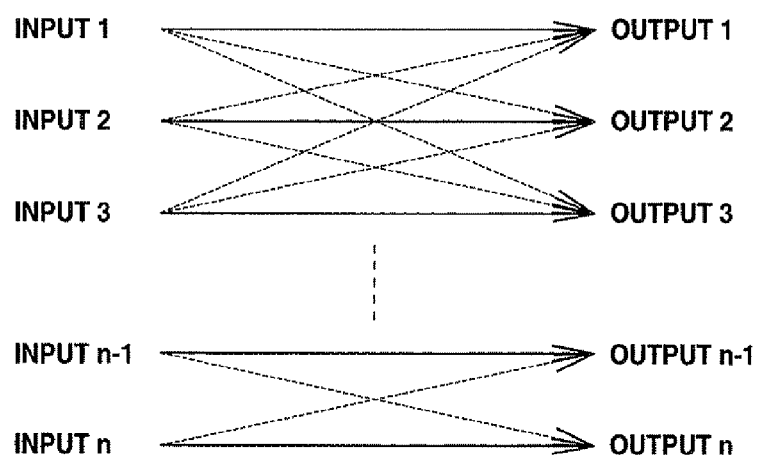
FIG.90
$$\begin{bmatrix} 1 & 0 & 0 & \cdots & 0 \\ 0 & 1 & 0 & \cdots & 0 \\ 0 & 0 & 1 & \cdots & 0 \\ & \vdots & & \vdots & \vdots \\ 0 & 0 & 0 & \cdots & 1 \end{bmatrix}$$
REPLACEMENT MATRIX (SOLID LINE)

FIG.91
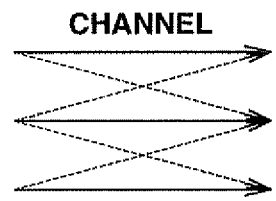
REPLACEMENT MATRIX 1
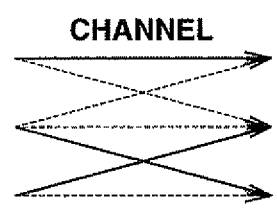
REPLACEMENT MATRIX 2
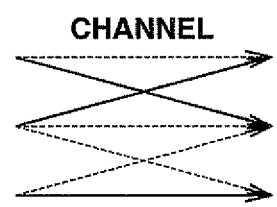
REPLACEMENT MATRIX 3

MEDICAL CONTROL APPARATUS

CROSS REFERENCE TO RELATED APPLICATION

This application is a continuation application of PCT/JP2006/314398 filed on Jul. 20, 2006 and claims the benefit of Japanese Applications No. 2005-214726 filed in Japan on Jul. 25, 2005, No. 2005-214727 filed in Japan on Jul. 25, 2005, No. 2005-214728 filed in Japan on Jul. 25, 2005 and No. 2005-214729 filed in Japan on Jul. 25, 2005 the entire contents of each of which are incorporated herein by their reference.

BACKGROUND OF THE INVENTION

1. Field of the Invention

The present invention relates to a medical control apparatus that controls driving section for causing a bending portion of a medical device to perform bending movements.

2. Description of the Related Art

Conventionally, endoscopes are widely used as medical devices. Such an endoscope is equipped with an elongated insertion portion, and by inserting the insertion portion into a body cavity, an operator is able to observe internal organs inside the body cavity or perform various therapeutic treatment using, as required, a treatment instrument inserted through a treatment instrument channel. In addition, with an endoscope applied to industrial fields, by inserting an elongated insertion portion, a worker is able to observe and examine flaws or corrosion inside a boiler, a turbine, an engine, a chemical plant or the like.

With such an endoscope, a bendable bending portion is provided on a proximal end-side of a distal end portion of an insertion portion. When using the endoscope, a user such as an operator operates bending operation inputting section such as a bending operation lever provided at an operation section to input an instruction on a bending direction or a bending speed of a bending portion as a bending quantity to bending driving section that causes bending movements of the bending portion.

Consequently, based on the bending quantity from the bending operation lever, the bending driving section causes a bending movement of the bending portion by mechanically pulling or relaxing a bending operation wire connected to a bending piece constituting the bending portion.

This type of a conventional endoscope includes an endoscope employing an electrical bending driving system or, in other words, an electric bending endoscope in which rotational movement of a motor built into the inside of the endoscope as bending driving section is electrically controlled, whereby the driving force of the motor pulls or relaxes a bending operation wire to cause bending movements of the bending portion.

For example, disclosed in Japanese Patent No. 2917263 is a technique regarding control section and the like in an electric bending endoscope, which includes a pulley that pulls the bending operation wire and which enables a torque of a motor corresponding to the pulley to be set so as to conform to the type of the insertion portion of the endoscope.

In addition, disclosed in Japanese Patent No. 2845255 is a technique regarding a bending operation apparatus of an electric bending endoscope, which is capable of equalizing load applied to a motor across an entire operation range of a bending portion.

SUMMARY OF THE INVENTION

The present invention comprises: a medical device having a bending portion in which a plurality of link members is respectively consecutively provided so as to be rotationally movable on a distal end-side of an insertion portion to be inserted into a subject to be examined; driving section for causing bending movements of the bending portion by respectively rotationally moving the plurality of link members; designating section that designates at least any one of the link members among the plurality of link members and designates a position and a direction of the link member; and control section that computes respective angles of the plurality of link members so that when the bending portion of the medical device moves, a position and a direction designated by the designating section are maintained when the link member designated by the designating section as well as other link members contiguous to the link member pass the position, and based on the computation results, controls the driving section to rotationally move the plurality of link members.

In addition, the present invention comprises: a medical device having a bending portion in which a plurality of link members is respectively consecutively provided so as to be rotationally movable on a distal end-side of an insertion portion to be inserted into a subject to be examined; driving section for causing bending movements of the bending portion by respectively rotationally moving the plurality of link members; designating section that designates a spatial angle formed by a most distal end-side link member of the insertion portion and a link member connected to the most distal end-side link member among the plurality of link members; and control section that controls the driving section to rotationally move the plurality of link members so that the spatial angle formed by the most distal end-side link member and the link member connected to the most distal end-side link member migrates from the distal end-side towards a proximal end-side so as to sequentially assume angles formed by adjacent link members.

BRIEF DESCRIPTION OF THE DRAWINGS

FIG. 88 relates to the variation of the seventh embodiment of the present invention and is an explanatory diagram for explaining channels settable by the channel setting section shown in FIG. 87, according to the variation of the seventh embodiment;

FIG. 89 relates to the variation of the seventh embodiment of the present invention and is a diagram showing an example of an input/output signal of the channel setting section;

FIG. 90 relates to the variation of the seventh embodiment of the present invention and is a diagram showing a replacement matrix to be used during channel setting by the channel setting section;

FIG. 91 relates to the variation of the seventh embodiment of the present invention and is a diagram showing an example of a channel setting set by the channel setting section;

DETAILED DESCRIPTION OF THE PREFERRED EMBODIMENTS

Embodiments of the present invention will be described below with reference to the drawings.

Figure 1:
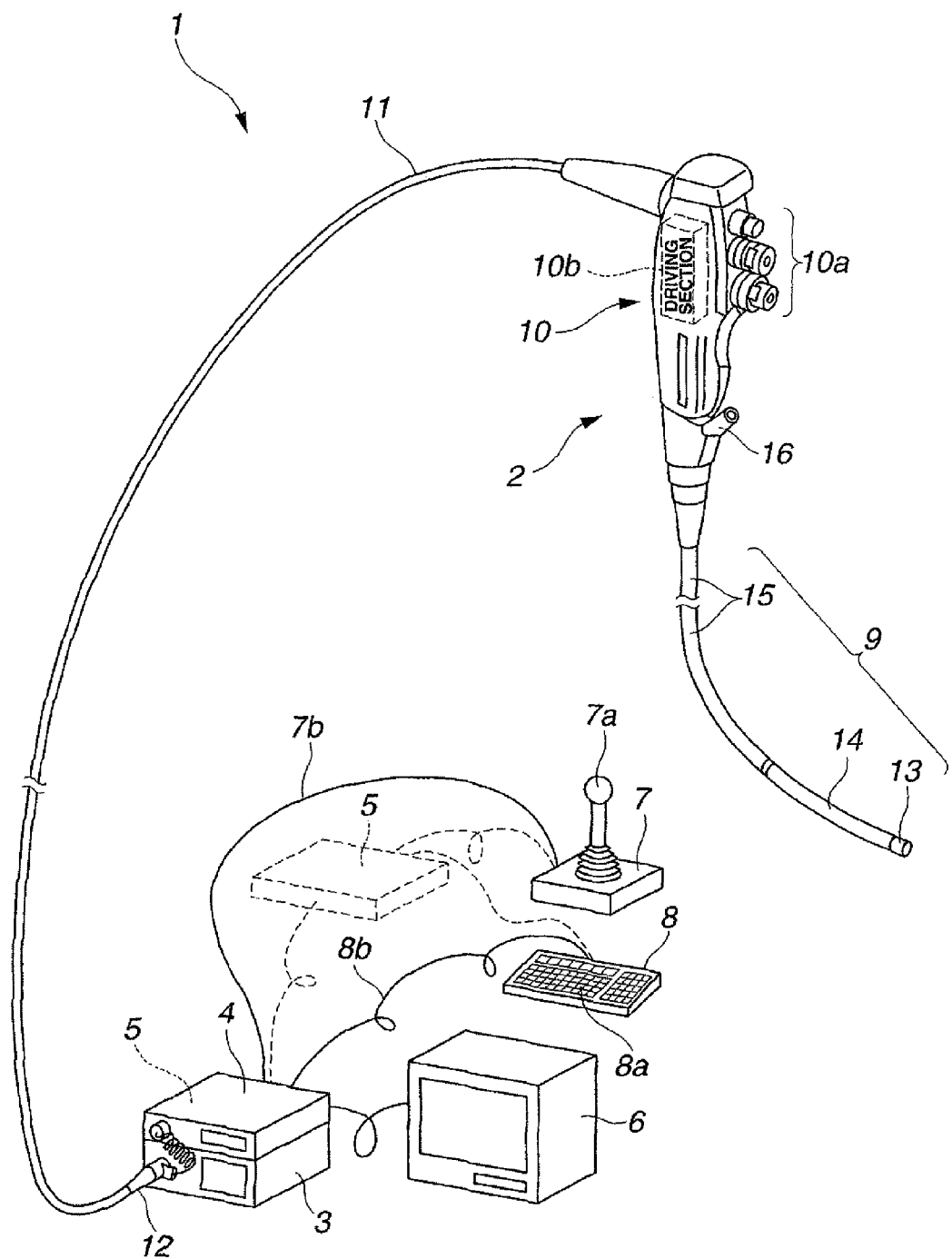
FIG. 1 relates to a first embodiment of the present invention and is a system configuration diagram of an endoscope apparatus configured using a medical control apparatus.

FIGS. 1 to 29 are for describing a basic configuration of a medical control apparatus according to a first embodiment of the present invention, wherein FIG. 1 is a system configuration diagram of an endoscope apparatus configured using the medical control apparatus.

As shown in FIG. 1, an endoscope apparatus 1 using a medical control apparatus according to the present invention comprises image pickup section, not shown, in a distal end portion of an insertion portion thereof, and further includes: an electronic endoscope (hereinafter, simply endoscope) 2 as a medical device provided with a driving section 10b for bending a bending portion 14 of an insertion portion 9, to be described later, either in an operation section 10 or in the bending portion 14; a light source 3 detachably connected to the endoscope 2 and which supplies illumination light thereto; a video processor 4 detachably connected to the endoscope 2, and which controls the image pickup section of the endoscope 2 and also processes a signal obtained from the image pickup section to output a standard video signal; a controller 5 either provided in the video processor 4 or provided separately therefrom, and which controls the driving section 10b of the endoscope 2 so that bending movements of the bending portion 14 are performed; a monitor 6 that displays an endoscopic image obtained through signal processing performed by the video processor 4; an operation command section 7 as designating section to be electrically connected to the controller 5; and a setting value command section 8 as setting value inputting section electrically connected to the controller 5.

Although not shown, the video processor 4 is arranged so that a VTR deck, a video printer, a video disk, an image file recording device or the like is connectable thereto.

The endoscope 2 includes: an elongated insertion portion 9 to be inserted into an observation object part; a grasping portion 10 consecutively provided at a proximal end portion of the insertion portion 9 and having an operation section 10a such as a video switch, an air/water supplying switch or the like; a universal cord 11 which is provided so as to extend from a lateral face of the grasping portion 10 and incorporates a signal cable to be connected to the image pickup section, not shown, or a light guide for transmitting illumination light, or the like; and a connector section 12 which is provided at an end portion of the universal cord 11 and detachably to be connected to the light source 3 and the video processor 4.

The insertion portion 9 is constituted such that: a distal end portion 13 provided at a distal end thereof; a bendable bending portion 14 provided posteriorly (the distal end-side of the insertion portion 9 to be inserted into a subject to be examined) to the distal end portion 13; and a long and flexible tube portion 15 which is provided posteriorly to the bending portion 14 and formed by a soft tubular member, are consecutively provided.

The distal end portion 13 is constituted such that: an image pickup section, as image pickup section, into which is incorporated a solid state image pickup device, not shown, such as a CCD, a circuit board for driving the solid state image pickup device, and the like; a light guide, not shown, that transmits illumination light for illuminating an observation object part inside a body cavity, and the like, are incorporated therein. A configuration of the bending portion 14 will be described later.

The operation command section 7 is electrically connected to the controller 5 via a connecting wire 7b. The operation command section 7 is configured so as to include, for example, a joystick 7a, and by operating the joystick 7a, an operation command value signal for causing the bending portion 14 to perform a bending movement is outputted.

The setting value command section 8 is also electrically connected to the controller 5 via a connecting wire 8b. The setting value command section 8 is configured so as to include, for example, a keyboard 8a, and through key operations performed at the keyboard 8a, various setting values necessary for bending the bending portion 14 is inputted to the controller 5.

Next, a configuration of the bending portion 14 will be described with reference to FIGS. 3 to 8. For simplicity, the description of the bending portion 14 will be made on the assumption that the bending portion 14 is handled as a planar movement driving section (two-dimensional planar movement).

Figure 3:
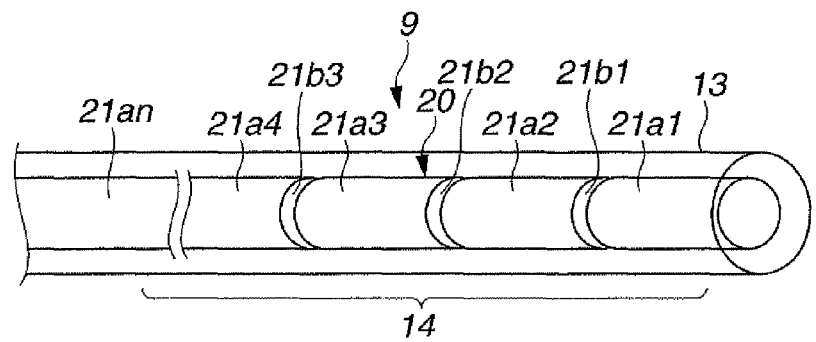
FIG. 3 relates to a first embodiment of the present invention and is a layout diagram presenting a perspective view of a substantial part of an insertion portion driving mechanism seen from a distal end-side of the insertion portion.
Figure 4:
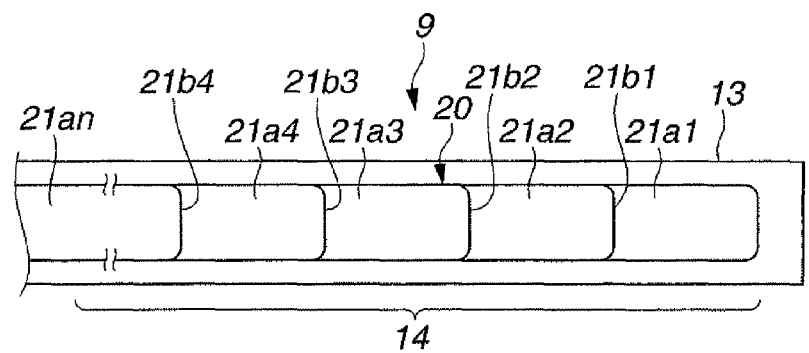
FIG. 4 relates to a first embodiment of the present invention and is a layout diagram showing the substantial part of the insertion portion driving mechanism.
Figure 5:
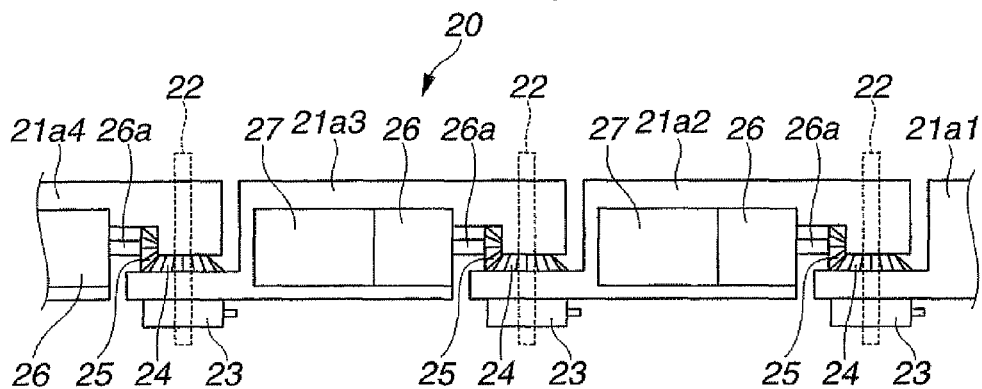
FIG. 5 relates to a first embodiment of the present invention and is a schematic configuration diagram of a bending portion whose driving mechanism is constituted by a motor and a gear.
Figure 6:
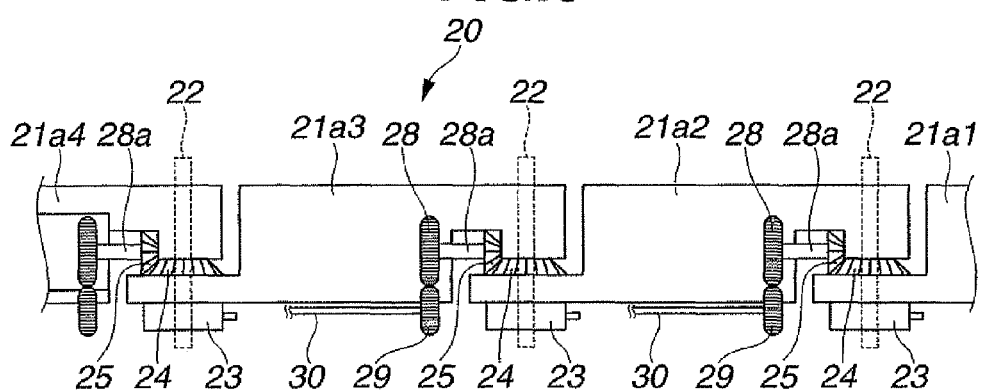
FIG. 6 relates to a first embodiment of the present invention and is a schematic configuration diagram showing a first variation of the bending portion shown in FIG. 5.
Figure 7:
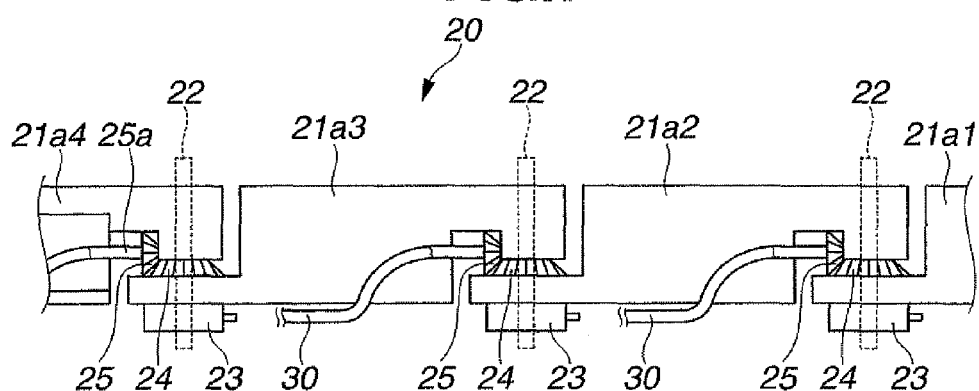
FIG. 7 relates to a first embodiment of the present invention and is a schematic configuration diagram showing a second variation of the bending portion shown in FIG. 5.

FIGS. 3 and 4 are for describing a schematic configuration of a distal end-side of an insertion portion including a bending portion having a driving mechanism with a link structure, wherein FIG. 3 is a layout diagram presenting a perspective view of a substantial part of the insertion portion driving mechanism from a distal end-side of the insertion portion, and FIG. 4 is a layout diagram showing a substantial part of the insertion portion driving mechanism. In addition: FIG. 5 is a schematic configuration diagram of a bending portion whose driving mechanism is constituted by a motor and a gear; FIG. 6 is a schematic configuration diagram showing a first variation of the bending portion shown in FIG. 5; FIG. 7 is a schematic configuration diagram showing a second variation of the bending portion shown in FIG. 5; and FIG. 8 is a perspective view showing a connection configuration of a motor and a flexible shaft.

As shown in FIGS. 3 and 4, the bending portion 14 is provided at the distal end-side of the insertion portion 9 to be inserted into a subject to be examined. The bending portion 14 has an insertion portion driving mechanism 20 configured so that a plurality of link members $21a1$, $21a2$, $21a3$, ..., $21an$ (where n is a natural number) is consecutively connected so as to be respectively rotationally movable by a plurality of joint members $21b1$, $21b2$, $21b3$, ..., $21bn$. In other words, the insertion portion driving mechanism 20 has a multi-joint link structure.

The driving section 10b is constituted by a motor 27 (refer to FIGS. 5 and 8) that is a driving source for respectively rotationally moving the plurality of link members $21a1$, $21a2$, $21a3$, ..., $21an$.

Figure 8:
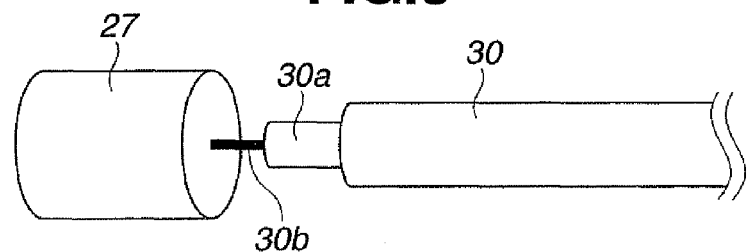
FIG. 8 relates to a first embodiment of the present invention and is a perspective view showing a connection configuration of a motor and a flexible shaft.

In the case where the motor 27 that is the driving section 10b is provided in the operation section 10, as shown in FIG. 8, a flexible shaft 30 is connected via a joint 30a to a driving shaft 27a of the motor 27. Although not shown, the flexible shaft 30 is provided so as to extend in the insertion portion 9, and a proximal end portion thereof is connected to the plurality of link members $21a1$, $21a2$, $21a3$, ..., $21an$. Consequently, the rotational force of each motor 27 is arranged to be respectively transmitted to the plurality of link members 21 via the flexible shaft 30.

In addition, in the case where the motor 27 that is the driving section 10b is provided in the bending portion 14 of the insertion portion 9, as shown in FIG. 5, the motor 27 is respectively disposed in the plurality of link members $21a1$, $21a2$, $21a3$, ..., $21an$ constituting the insertion portion driving mechanism 20. The rotational force of each motor 27 is arranged to be respectively transmitted to the plurality of link members $21a1$, $21a2$, $21a3$, ..., $21an$ by a connecting gear unit 26 or the like to be connected to the motor 27.

The numbers of the link members $21a$ and the joint members $21b$ are not limited to the configuration examples shown in the drawings, and configurations are also possible wherein the numbers thereof are increased or decreased in accordance with the intended use of the endoscope 2. The link member $21a1$ is disposed on a most distal end-side of the distal end portion 13, and is arranged so that link members $21a2$, $21a3$, ..., $21an$ are sequentially connected to a rear end-side thereof. In association therewith, the joint members $21b1$, $21b2$, $21b3$, ..., $21bn$ are also respectively disposed between the link members $21a$ in sequence from the distal end portion 13 side.

A specific configuration of the bending portion 14 is shown in FIG. 5.

As shown in FIG. 5, in the insertion portion driving mechanism 20 of the bending portion 14, the motor 27 that is the driving section 10b is respectively disposed in the plurality of link members $21a1$, $21a2$, $21a3$, ..., $21an$.

The plurality of link members $21a1$, $21a2$, $21a3$, ..., $21an$ is respectively connected by joint shafts 22 that are the joint members $21b1$, $21b2$, $21b3$, ..., $21bn$ so as to be rotationally movable. The joint shafts 22 are shaft members, and a potentiometer 23 as first detecting section is respectively mounted on the joint shafts 22.

The potentiometer 23 is arranged to detect a rotational quantity of the joint shaft 22 and output the same as a state quantity detection signal of the link member $21a$ to the controller 5 via a signal wire, not shown.

A gear 24 that fixes the joint shaft 22 so as to be rotationally movable is respectively fixed to each proximal end-side of the plurality of link members $21a1$, $21a2$, $21a3$, ..., $21an$. A gear 25 securely fixed to a shaft $26a$ of the connecting gear unit 26 meshes with the gear 24. In other words, the connecting gear unit 26 is connected to a driving shaft, not shown, of the motor 27 provided at each of the link members $21a1$, $21a2$, $21a3$, ..., $21an$. The rotational force of the driving shaft is arranged to be transmitted to the gear 25 via the shaft $26a$.

Consequently, the rotational force of the motor 27 is transmitted to the gear 24 via the shaft $26a$ of the connecting gear unit 26 and the gear 25, thereby enabling the link member $21a$ to which the gear 24 is fixed to rotationally move in a predetermined direction.

Since the bending portion 14 shown in FIG. 5 includes, for each link member $21a$, the motor 27, the connecting gear unit 26 and the gears 24 and 25 which constitute the insertion portion driving mechanism 20, by performing rotational control of the motor 27 of a designated link member $21a$ among the plurality of link members $21a1$, $21a2$, $21a3$, ..., $21an$, it is possible to cause rotational movement of only the designated link member $21a$.

In the present embodiment, the driving mechanism 20 of the bending portion 14 may be configured like the first variation shown in FIG. 6 or the second variation shown in FIG. 7. The above-mentioned first and second variations of the bending portion 14 will now be described with reference to FIGS. 6 and 7.

Unlike the bending portion 14 shown in FIG. 5, with the bending portion 14 according to the first and second variations, instead of providing a motor 27 at each link member $21a$, a plurality of motors 27 that is the driving section 10b is provided in the operation section 10. Flexible shafts 30 are respectively connected to driving shafts $30b$ of the motors 27 via joints $30a$. The respective flexible shafts 30 are provided so as to extend in the insertion portion 9, and are respectively connected to the link members $21a$, $21b$, $21c$, ..., $21n$. The rotational force of the motors 27 is arranged to be respectively transmitted to the plurality of link members $21a$, $21b$, $21c$, $21n$ via corresponding flexible shafts 30.

As shown in FIG. 6, while the configuration of the bending portion 14 according to the first variation is approximately the same as the insertion portion driving mechanism 20 shown in FIG. 5, a gear 29 is provided at a distal end-side of a flexible shaft 30 provided at each link member 21a so as to extend therefrom.

A connecting gear 28 meshes with the gear 29. The connecting gear 28 is internally mounted in the link member 21a, and a gear 25 is securely fixed to the side of the connecting gear 28 that is opposite to the shaft 29a. The rotational force from the flexible shaft 30 is transmitted to the gear 24 via the gear 25.

Consequently, the rotational force of the motor 27 is transmitted to the gear 24 via the driving shaft 30b, the joint 30a, the flexible shaft 30, the gear 29, the connecting gear 28, the shaft 29a and the gear 25, thereby enabling the link member 21a to which the gear 24 is fixed to rotationally move in a predetermined direction.

In the same manner as the bending portion 14 shown in FIG. 5, since the bending portion 14 according to the first variation includes, for each link member 21a, the flexible shaft 30, the connecting gear 28 and the gears 24 and 25 which constitute the insertion portion driving mechanism 20, by performing rotational control of the motor 27 of a designated link member 21a among the plurality of link members 21a1 to 21an, it is possible to cause rotational movement of the designated link member 21a.

As shown in FIG. 7, while the configuration of the bending portion 14 according to the second variation is approximately the same as the insertion portion driving mechanism 20 according to the first variation, the connecting gear 28 has been removed and the flexible shaft 30 provided at each link member 21a so as to extend therefrom is now disposed inside each link member 21a.

The gear 25 is provided on the distal end-side of the flexible shaft 30. Therefore, the rotational force from the flexible shaft 30 is arranged to be directly transmitted to the gear 24 fixed to the rear end-side of each link member 21a via the gear 25 without having to travel through a connecting member such as the connecting gear 28. Consequently, in the same manner as in the first variation, it is possible to rotationally move the link member 21a to which the gear 24 is fixed in a predetermined direction.

In the same manner as with the first variation, since the bending portion 14 according to the second variation includes, for each link member 21a, the flexible shaft 30 and the gears 24 and 25 which constitute the insertion portion driving mechanism 20, by performing rotational control of the motor 27 of a designated link member 21a among the plurality of link members 21a1 to 21an, it is possible to cause rotational movement of only the designated link member 21a.

Next, an electrical main configuration of the endoscope apparatus 1 comprising the endoscope 2 having such a bending portion 14 will be described with reference to FIG. 2.

Figure 2:
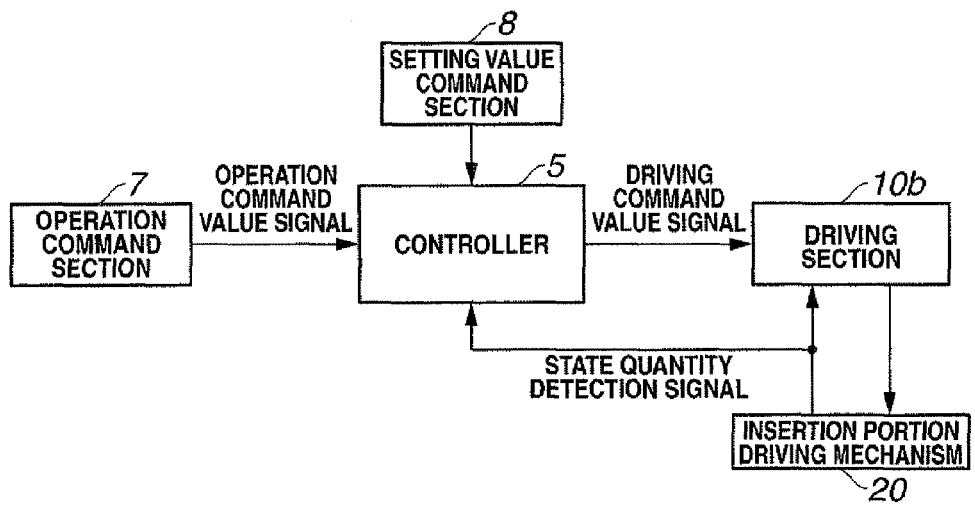
FIG. 2 relates to a first embodiment of the present invention and is a block diagram showing an electrical configuration of major components of the endoscope apparatus.

FIG. 2 is a block diagram showing an electrical configuration of major components of the endoscope apparatus 1.

As shown in FIG. 2, a primary part of the endoscope apparatus 1 is constituted by: an operation command section 7 as operation section and designating section constituted using, for example, a joystick 7a; a setting value command section 8 as setting value inputting section constituted using a keyboard 8a; a controller 5 that outputs a driving command value signal for controlling the driving section 10b based on an operation command value signal from the operation command section 7, a setting value set by the setting value command section 8 and a state quantity detection signal from the potentiometer 23 or the like; driving sections 10b that are the motors 27 or the like that are respectively rotationally controlled based on the driving command value signal from the controller 5; and the insertion portion driving mechanism 20 provided in the bending portion 14 on which attitude control is performed by the rotational force of the driving section 10b.

The operation command section 7 is operation section for instructing bending of the bending portion 14 using the joystick 7a, and outputs an operation command value signal based on operation to the controller 5. The operation command section 7 is also designating section that designates a link member 21a whose two-dimensional position and direction is to be fixed among the plurality of link members 21a1 to 21an constituting the bending portion 14, and outputs the operation command value signal based on the operation to the controller 5.

Figure 9:
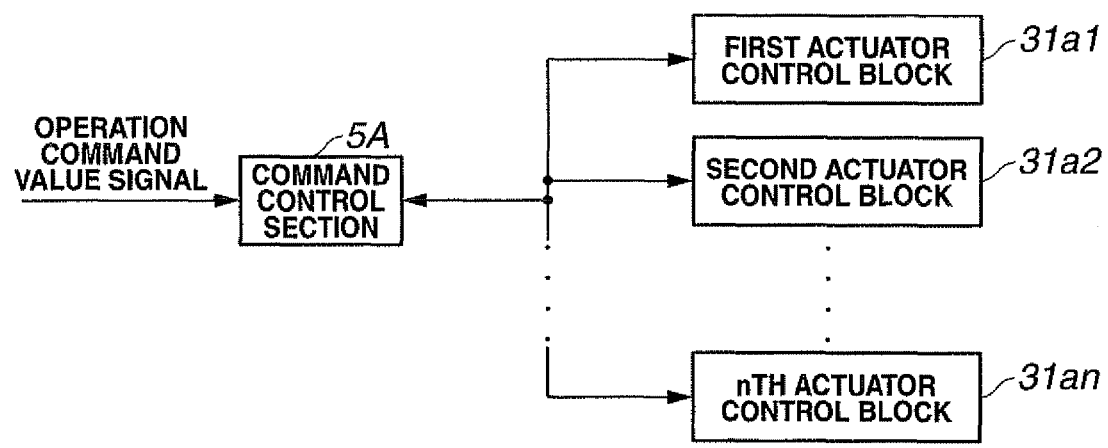
FIG. 9 relates to a first embodiment of the present invention and is a control block diagram of a substantial part including a controller, a driving section and the insertion portion driving mechanism section.

A control block diagram of a substantial part having the controller 5, the driving section 10b and the insertion portion driving mechanism 20 is shown in FIG. 9.

As shown in FIG. 9, the controller 5 (refer to FIG. 2) includes a command control section 5A. The command control section 5A is arranged so that an operation command value signal from the operation command section 7 is supplied thereto.

Based on a supplied operation command value signal and state quantity detection signal, the command control section 5A performs computational processing or the like required to control the driving section 10b provided at an actuator control block 31.

A plurality of first, second, . . . , nth actuator control blocks 31a1 to 31an provided at each of the plurality of link members 21a constituting the insertion portion driving mechanism 20 of the bending portion 14 is electrically connected to the command control section 5A.

Figure 10:
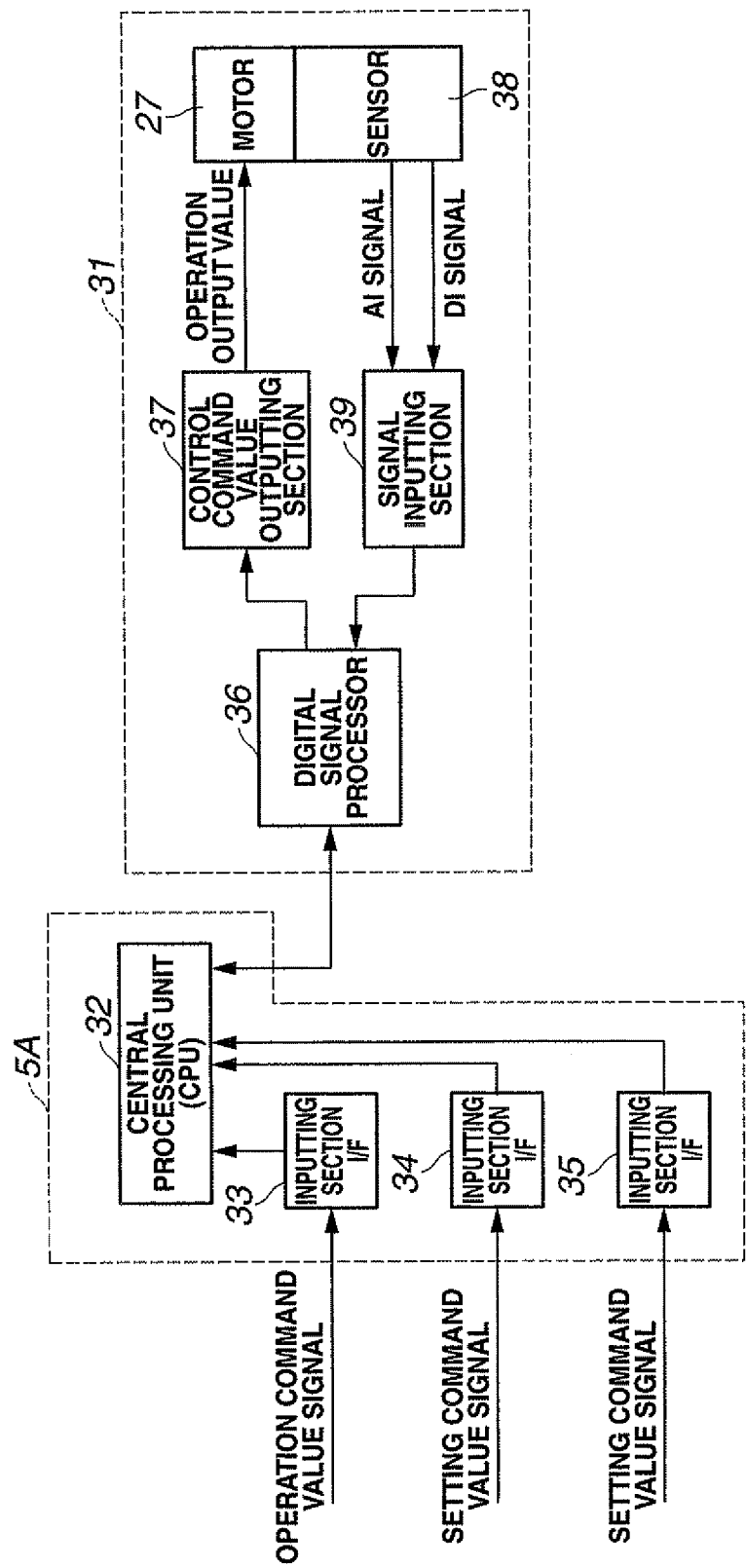
FIG. 10 relates to a first embodiment of the present invention and is a block diagram showing a specific configuration of the command control section and the actuator control block shown in FIG. 9.

FIG. 10 is a block diagram showing a specific configuration of the command control section 5A and the actuator control block 31 shown in FIG. 9.

As shown in FIG. 10, the command control section 5A includes: an inputting section I/F 33 for inputting an operation command value signal from the operation command section 7; inputting sections I/F 34 and I/F 35 for inputting a setting command value from the setting value command section 8; and a central processing unit (e.g., a CPU) 32 that controls driving sections 10b in the first, second, . . . , nth actuator control blocks 31a1 to 31an based on various command value signals inputted via the I/Fs 33 to 35.

In the case where the joystick 7a outputs analog operation command value signals, the inputting section I/F 33 is capable of inputting such an analog signal. In addition, in the case where the joystick 7a outputs other digital operation command value signals, the inputting section I/F 33 is capable of inputting such a digital signal.

An analog setting value command signal required to consecutively move a plurality of link members 21a can also be inputted through the inputting section I/F 34, while digital setting command values for changing parameters and the like can be inputted through the inputting section I/F 35. The inputting section I/F 34 and the inputting section I/F 35 may also be configured as one I/F.

On the other hand, the actuator control block 31 performs various computational processing at high speed, and includes: a digital signal processor (hereinafter referred to as a DSP) 36 that creates and outputs a driving command value signal based on computation results; a control command value outputting section 37 that creates and outputs an operation output value signal based on a driving command value signal (servo command value signal) from the DSP 36; a motor 27 that is the driving section 10b whose rotation is controlled based on the operation output value signal (driving signal) from the control command value outputting section 37; a sensor 38 that is first detecting section such as an encoder that detects rotational positions of the motor 27, a potentiometer 23 that detects rotational angles of the link member 21a, or the like; and a signal inputting section 39 that detects a state quantity detection signal that is position information detected by the sensor 38 and outputs the state quantity detection signal to the DSP 36.

While the motor 27 is used in the present embodiment as the driving section 10b, the present invention is not limited to this arrangement. Instead, configurations are possible in which another actuator is used as the driving section 10b.

Figure 11:
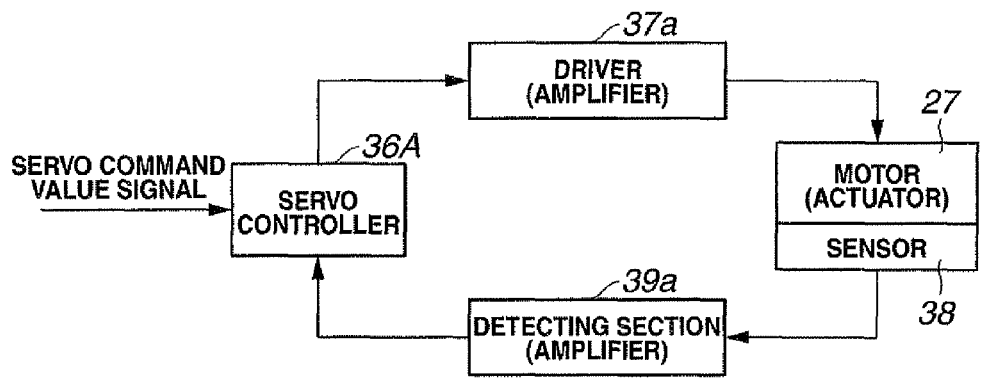
FIG. 11 relates to a first embodiment of the present invention and is a block diagram showing a specific configuration of the actuator control block.
Figure 12:
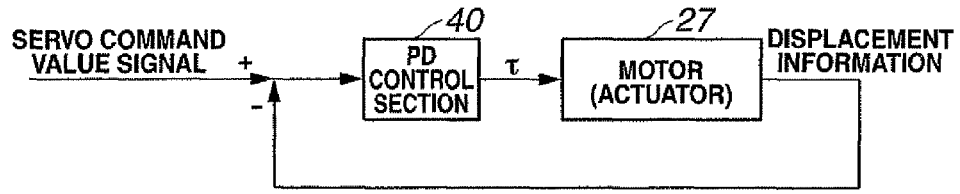
FIG. 12 relates to a first embodiment of the present invention and is a block line diagram of the servo controller shown in FIG. 11.

FIG. 11 is a block diagram showing a specific configuration of the actuator control block, while FIG. 12 is a block diagram of the servo controller shown in FIG. 11.

In the actuator control block 31 shown in FIG. 10, the DSP 36 constitutes the servo controller 36A shown in FIG. 11. The servo controller 36A creates an operation output value signal (driving signal) based on a supplied servo command value signal, and outputs the same to a driver (amplifier) 37a that is the control command value outputting section 37. The servo controller 36A may be replaced with the CPU 32 shown in FIG. 10.

The driver 37a amplifies the supplied operation output value signal to rotate the motor 27. Consequently, due to the rotation of the motor 27, the link member 21a shown in FIG. 5 rotationally moves. At this point, the sensor 38 creates a state quantity detection signal of the link member 21a and outputs the same to a detecting section (amplifier) 39a that is the signal inputting section 39.

The detecting section 39a amplifies the supplied state quantity detection signal and outputs the same to the servo controller 36A. Accordingly, the servo controller 36A is arranged to perform rotational control of the motor 27 while comparing the supplied state quantity detection signal and servo command value signal.

In this case, as shown in FIG. 12, the servo controller 36A creates an operation output value signal (driving signal) based on a supplied servo command value signal and a state detection signal that is displacement information of the motor 27 obtained from the sensor 38 by performing PD control such as known proportional/differential control using a PD control section 40, and rotationally controls the motor 27 by supplying the operation output value signal thereto.

With the endoscope 2 provided with the bending portion 14 having such a multi-joint link structure, in order to perform insertion in a shape conforming to the interior shape of a tube cavity such as the large intestine, it is required that the distal end-side link member 21a1 be controlled to an optimum attitude angle and, at the same time, the plurality of other link members 21a contiguous to the distal end-side link member 21a1 be controlled in conjunction thereto. A basic control method used in the above-described present invention will now be described with reference to FIGS. 13 to 15.

Figure 13:
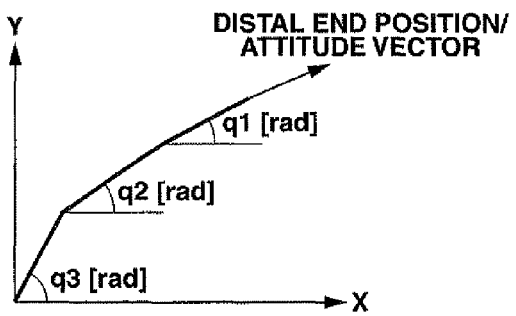
FIG. 13 relates to a first embodiment of the present invention and is an explanatory diagram showing a state in which a distal end portion-side link member assumes a predetermined distal end position and an attitude vector.
Figure 14:
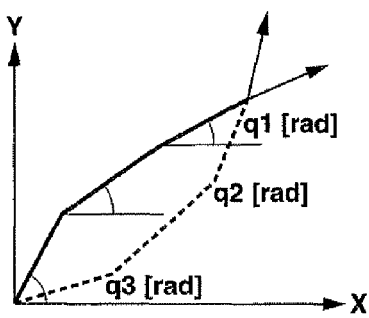
FIG. 14 relates to a first embodiment of the present invention and is an explanatory diagram showing states of other link members which are anticipated when the link member shown in FIG. 13 is in the attitude state shown therein.
Figure 15:
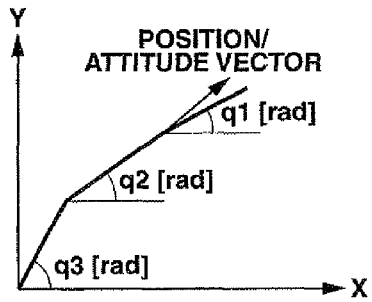
FIG. 15 relates to a first embodiment of the present invention and is an explanatory diagram showing a state of a predetermined position and an attitude vector when attitude control is independently performed on only the distal end portion-side link member.

FIGS. 13 to 15 are for describing attitude control of a bending portion having a multi-joint link structure and are explanatory diagrams corresponding to link members 21a1 to 21a3 on the distal end portion 13 side, wherein: FIG. 13 is a diagram showing a state in which the distal end portion 13 side link member 21a1 assumes a predetermined distal end position and an attitude vector; FIG. 14 is a diagram showing states of other link members which are anticipated when the link member 21a1 shown in FIG. 13 is in the attitude state shown therein; and FIG. 15 is a diagram showing a state of a predetermined position and attitude vector when attitude control is independently performed on only the distal end portion 13 side link member 21a1.

The command control section 5A of the controller 5 according to the present embodiment is arranged so that, when respectively performing attitude control on each of the plurality of link members 21a1 to 21an that constitute the bending portion 14, computational processing based on kinematics (forward kinematics and inverse kinematics), to be described later, is performed.

Computational processing based on forward kinematics refers to computational processing for determining a position/attitude vector of a distal end portion when an angle of each joint (each link member 21a) is known, while computational processing based on inverse kinematics refers to computational processing for determining an angle of each joint (each link member 21a) when a position/attitude vector of a distal end portion is known.

The command control section 5A performs computational processing based on a basic formula that quantifies robot kinematics, to be described later. Such a basic formula that quantifies robot kinematics is provided below. Hereinafter, for simplicity, descriptions will only be given on movement involving three links and limited, as described above, to a two-dimensional plane. However, replacement of two-dimensional planar movement by a three-dimensional planar movement can be accommodated by similarly replacing known robotic coordinate conversion processing with processing by the DH convention (Denavit-Hartenberg convention).

Now, if x denotes end-point coordinates, q denotes joint coordinates and J denotes a Jacobian (velocity vector), the following formula can be defined. It is assumed that x, q and J denote respective vectors.

Position relationship between end-point and joint $x=p(q)$ (Formula 1)

FIG. 13 represents two-dimensional coordinates and therefore may be expressed as $$x = \begin{pmatrix} X \\ Y \end{pmatrix}.$$

Velocity relationship between end-point and joint $(dx/dt)=J \cdot (dq/dt)$ (Formula 2)

By solving the above formulas (Formula 1, Formula 2) and the kinematics (Lagrangian) of each link restraint condition, the following robot dynamics (the relationship between torque $\tau$ (or $\delta^2 q/\delta t^2$) and dynamics at the joint coordinates) can be derived.

$\tau = H(q) \cdot (d^2q/dt^2) + h(q,(dq/dt)) + g(q) - \tau_{EXT}$, (Formula 3)

where H(q) represents an inertial matrix term, h represents a dynamics term dependent on Coriolis and attitude variations, g represents a gravitational force term and $\tau$EXT represents a disturbance element.

With respect to each joint (that is each of the link members 21a denoted by q1, q2 and q3 in FIG. 13) and the end-point position (the position of the distal end-side link member 21a1 and denoted by q1), as for the dynamic relationship between end-point position acceleration and joint acceleration, matrix space can be decomposed into a kernel space (kernel) and a null space (null) using the relationships expressed by Formulas 1 to 3 above and the result of a temporal differentiation operation performed on both sides of Formula 2 by performing matrix decomposition (singular value decomposition or the like) of a relationship expressed as $X=J \cdot (d^2q/dt^2)+(dJ/dt) \cdot (dq/dt)$ and the right-hand side.

Consequently, Formula 4 presented below can be derived.

$$(d^2q/dt^2) = J^\#((d^2x/dt^2) - (dJ/dt) \cdot (dq/dt)) + (I - J^\# \times J) \cdot (d^2q/dt^2)$$ (Formula 4)

Note that the notation # in Formula 4 represents a pseudo-inverse matrix. Generally speaking, in Formula 4, the first term of the left-hand side represents movement of the end-point position and the second term thereof represents movement of the respective joints other than the end-point. Therefore, in the case where the end-point position (the position of the distal end-side link member 21a1 and denoted by q1) is determined, attitudes of subsequent joints (other link members 21a2 to 21an and denoted by q1, q2) are not uniquely determined.

In other words, as shown in FIG. 14, when the position of the distal end portion q1 is determined, attitudes that can be assumed by a link member including q1 and constituted by q2 and q3 may include attitudes depicted by the dotted line in the diagram in addition to those depicted by the solid line, suggesting that the attitude is not uniquely determined. Therefore, each of the link members 21a of the bending portion 14 will acquire redundancy of a robot attitude.

While the command control section 5A of the controller 5 performs a calculation of a torque to be assigned to each link in order to control the link motion equations expressed as Formulas 3 and 4 provided above or, in other words, performs the calculations expressed as Formulas 7 and 8 to be described later, as shown in FIG. 15, the command control section 5A is arranged so as to perform computational processing based on link position/attitude kinematics for the link members 21a2 and 21a3 (q2 and q3) in the stage subsequent to the distal end portion and to perform computational processing based on an algorithm (stored in a memory, not shown) that performs independent driving control for the distal end-side link member 21a1 (q1).

Consequently, when the position and attitude (direction) of the distal end-side link member 21a1 is determined, it is possible to calculate angles of other link members 21 contiguous to the distal end-side link member 21a1 by performing the computational processing described above.

Next, a specific configuration of the servo controller 36A for performing computational processing based on the kinematics (forward kinematics and inverse kinematics) and a control method thereof will be described with reference to FIGS. 16 to 21.

Figure 16:
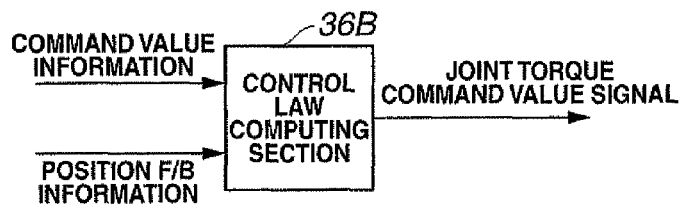
FIG. 16 relates to a first embodiment of the present invention and is a block diagram showing a schematic configuration of a servo controller.
Figure 17:
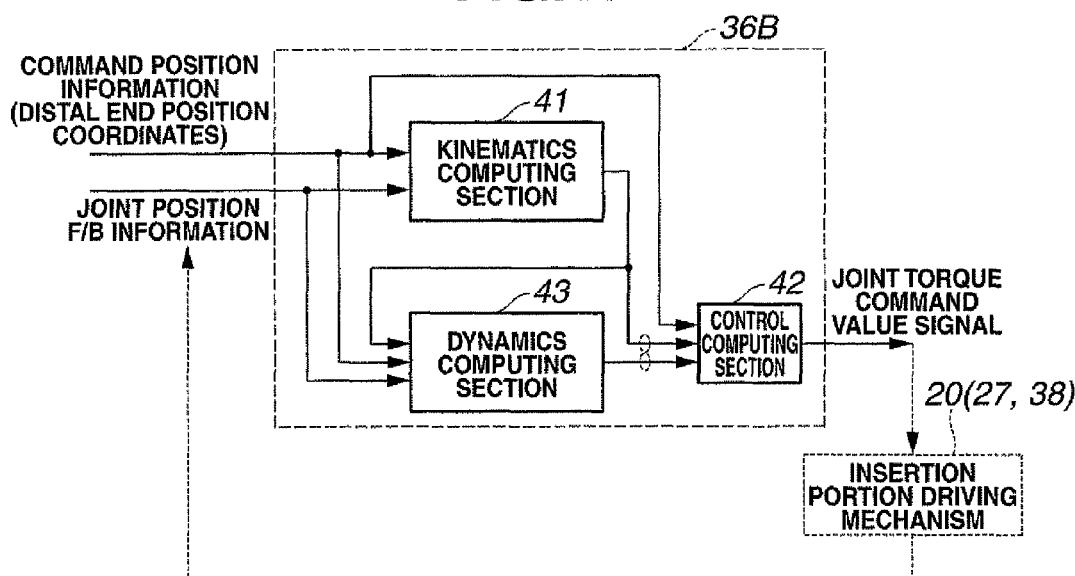
FIG. 17 relates to a first embodiment of the present invention and is a block diagram showing a specific configuration of the control law computing section shown in FIG. 16.
Figure 18:
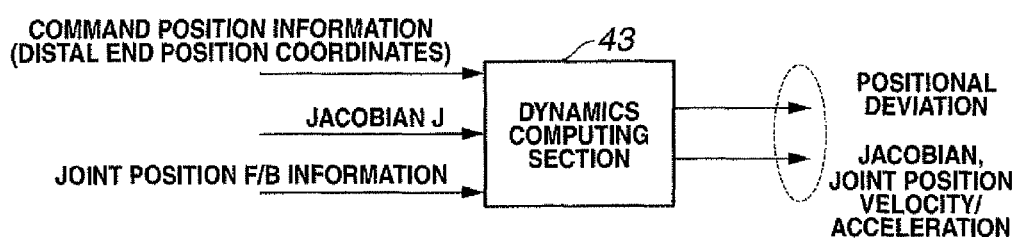
FIG. 18 relates to a first embodiment of the present invention and is a block diagram showing a schematic configuration of the dynamics computing section shown in FIG. 17.
Figure 19:
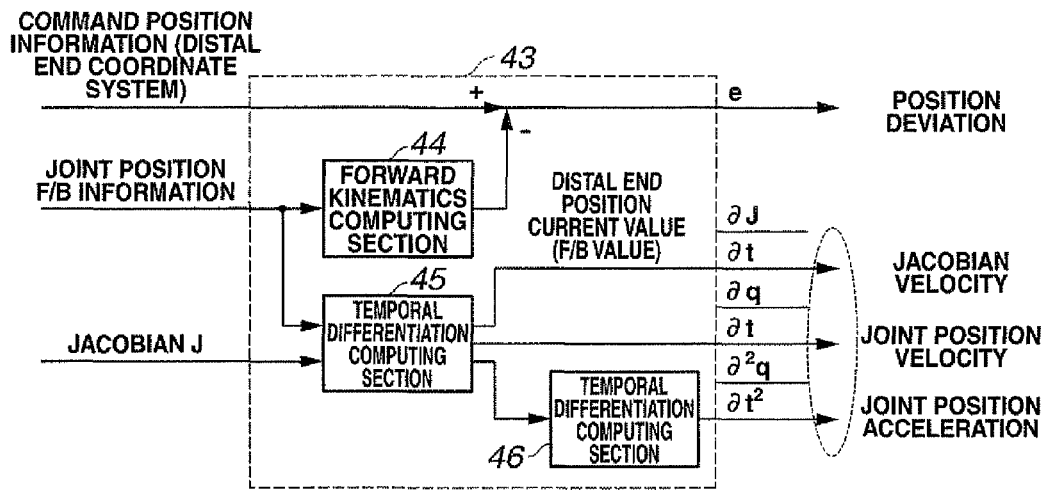
FIG. 19 relates to a first embodiment of the present invention and is a block diagram showing a specific configuration of the dynamics computing section shown in FIG. 18.
Figure 20:
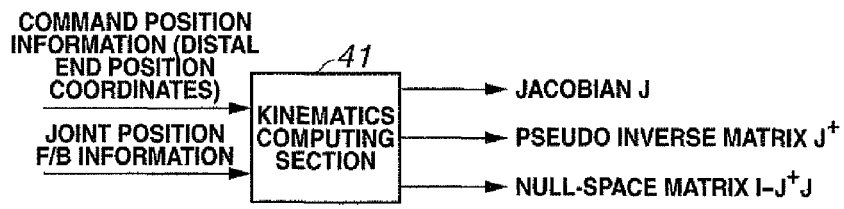
FIG. 20 relates to a first embodiment of the present invention and is a block diagram showing a schematic configuration of the kinematics computing section shown in FIG. 17.
Figure 21:
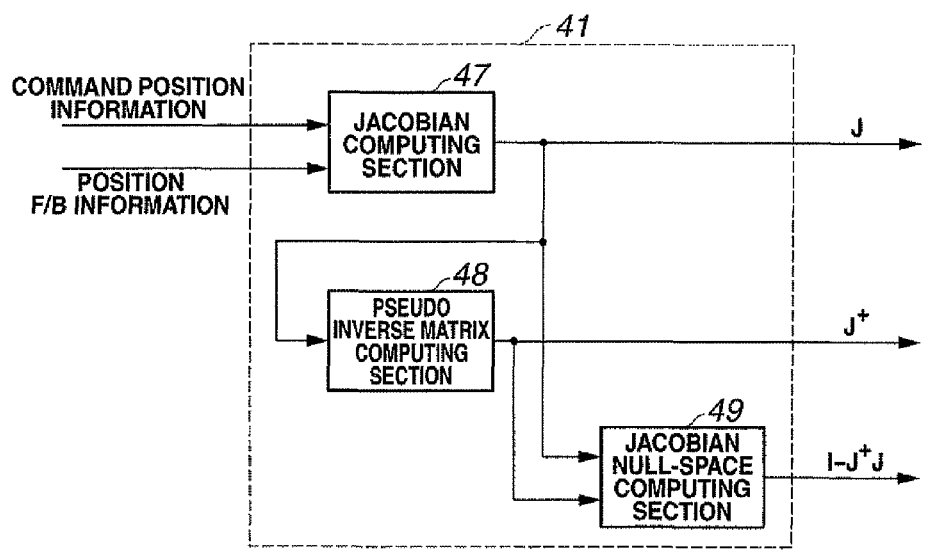
FIG. 21 relates to a first embodiment of the present invention and is a block diagram showing a specific configuration of the kinematics computing section shown in FIG. 20.

FIGS. 16 to 21 are for describing a specific configuration of the servo controller 36A and a control method thereof, wherein: FIG. 16 is a block diagram showing a schematic configuration of the servo controller 36A; FIG. 17 is a block diagram showing a specific configuration of the control law computing section 36B shown in FIG. 16; FIG. 18 is a block diagram showing a schematic configuration of the dynamics computing section 43 shown in FIG. 17; FIG. 19 is a block diagram showing a specific configuration of the dynamics computing section 43 shown in FIG. 18; FIG. 20 is a block diagram showing a schematic configuration of the kinematics computing section 41 shown in FIG. 17; and FIG. 21 is a block diagram showing a specific configuration of the kinematics computing section 41 shown in FIG. 20.

As shown in FIG. 16, the servo controller 36A includes a control law computing section 36B to which is supplied: command value information (also including setting value information) such as setting command value signals including a servo command value signal at the distal end-side link member 21a1 or each link member 21a; and position feedback information (hereinafter referred to as position F/B information) such as a state quantity detection signal at each link member 21a.

Based on the supplied command value information and position F/B information, the control law computing section 36B performs computational processing for obtaining joint torque command value signals as driving command value signals corresponding to each link member 21a at the kinematics computing section 41 and the dynamics computing section 43, to be described later, and outputs the same to the driving section 10b.

A specific configuration of the control law computing section 36B is shown in FIG. 17.

As shown in FIG. 17, the control law computing section 36B includes: the kinematics computing section 41 to which command value position information that is distal end position coordinates of the distal end-side link member 21a1 and joint position F/B information of each joint (each link member 21a) are inputted, and which uses the information to perform computational processing based on kinematics; the dynamics computing section 43 to which a computation result of the kinematics computing section 41, the command value information and the joint position F/B information are inputted, and which uses the information to perform dynamics computational processing to derive a dynamic part of a variation of each link member 21a; and the control computing section 42 to which the command value information and respective computation results of the kinematics computing section 41 and the dynamics computing section 43 are inputted, and which, based on the information, performs computational processing of a joint torque command value signal required to control each link member 21a.

The control law computing section 36B controls the insertion portion driving mechanism (manipulator) 20 by supplying the created joint torque command value signal to the driving section 10b in the actuator control block 31.

At this point, the manipulator 20 outputs joint position F/B information of each joint that is a state quantity detection signal detected by the sensor 38 in the actuator control block 31 to the kinematics computing section 41 and the dynamics computing section 43.

FIG. 18 shows a schematic configuration of the dynamics computing section 43, and FIG. 19 shows a specific configuration of the dynamics computing section.

As shown in FIG. 18, a Jacobian (a velocity vector that is also referred to as J or Jacobian J), to be described later, which is a computation result of the kinematics computing section 41, the command value information and the joint position F/B information are inputted to the dynamics computing section 43, whereby the dynamics computing section 43 performs dynamics computational processing using the information in order to derive a dynamic part of a variation of each link member 21a or, more specifically, a position deviation, a Jacobian JS, joint position velocity/acceleration of each link member 21a, and outputs the same as computational processing results.

More specifically, as shown in FIG. 19, the dynamics computing section 43 includes a forward kinematics computing section 44, a temporal differentiation computing section 45 and a temporal differentiation computing section 46.

The forward kinematics computing section 44 performs computational processing based on above-described forward kinematics using the joint position F/B information. A computation result thereof is subtracted from distal end position information of the distal end-side link member 21a1 by a subtracter to derive a position deviation e of each link member 21a.

The joint position F/B information and the Jacobian J are inputted to the temporal differentiation computing section 45. By performing temporal differentiation computational processing using the joint position F/B information and the Jacobian J, the temporal differentiation computing section 45 creates a displacement of each link member 21a or, more specifically, a Jacobian velocity δJ/δt and a joint position velocity δq/δt.

The temporal differentiation computing section 46 receives the joint position velocity δq/δt as an input, and by performing temporal differentiation computational processing, creates a joint position acceleration δ²q/δt².

FIG. 20 shows a schematic configuration of the kinematics computing section 41, and FIG. 21 shows a specific configuration of the kinematics computing section 41.

As shown in FIG. 20, the command value information and the joint position F/B information are inputted to the kinematics computing section 41. By performing computational processing based on kinematics using the information, the kinematics computing section 41 derives a Jacobian J of the distal end-side link member 21a1, a pseudo-inverse matrix J⁺ of the Jacobian J and a null-space pseudo-inverse matrix (I−J⁺J) of the Jacobian J, and outputs the same as computational processing results.

More specifically, as shown in FIG. 21, the kinematics computing section 41 includes a Jacobian computing section 47, a pseudo-inverse matrix computing section 48, and a Jacobian null-space computing section 49.

The Jacobian computing section 47 performs computational processing for obtaining a Jacobian J based the command position information and the position F/B information, and outputs the obtained Jacobian J to the control computing section 42 shown in FIG. 17, the pseudo-inverse matrix computing section 48 and the Jacobian null-space computing section 49.

Formula 5 that is based on Jacobian computational processing by the Jacobian computing section 47 is presented below.

$$J = \begin{pmatrix} \frac{\partial X_1}{\partial q_1} & \frac{\partial X_1}{\partial q_2} & \cdots & \frac{\partial X_1}{\partial q_n} \\ \vdots & \vdots & \vdots & \vdots \\ \frac{\partial X_n}{\partial q_1} & \frac{\partial X_n}{\partial q_2} & \cdots & \frac{\partial X_n}{\partial q_n} \end{pmatrix}$$ (Formula 5)

The pseudo-inverse matrix computing section 48 receives the Jacobian J as input, and by performing generalized inverse matrix computational processing thereon, creates a pseudo-inverse matrix J⁺ and outputs the same to the control computing section 42 shown in FIG. 17 and the Jacobian null-space computing section 49.

Formula 6 that is based on generalized inverse matrix computational processing is provided below.

$$J^+ = (J^T \cdot J)^{-1} \cdot J^T$$ (Formula 6)

Note that the superscript T in the formula represents a transposed matrix.

By performing Jacobian null-space computational processing on the supplied Jacobian J and pseudo-inverse matrix J⁺, the Jacobian null-space computing section 49 creates a pseudo-inverse matrix I−J⁺J and outputs the same to the control computing section 42 shown in FIG. 17.

Consequently, the Jacobian J, the pseudo-inverse matrix J⁺ of the Jacobian J and the Jacobian null-space pseudo-inverse matrix (I−J⁺J) are to be supplied to the control computing section 42 shown in FIG. 17 as computational processing results of the kinematics computing section 41. The control computing section 42 performs PD control based on the above-described command values and state quantity.

Next, control law formulas necessary for various computational processing performed at the above-mentioned control law computing section 36B shown in FIG. 17 will be described.

The endoscope apparatus 1 that uses a medical control apparatus according to the present invention comprises the insertion portion driving mechanism 20 that includes a plurality of link members 21a and a plurality of joint members 21b and which constitutes a manipulator. Therefore, the control law computing section 36B shown in FIG. 17 derives the joint torque command value signal by performing various computational processing based on the above-described Formula 3 and Formula 4 that are manipulator dynamic equations and further using various formulas based on a manipulator control law, to be described later.

A formula based on the manipulator control law is presented below. In this case, if τ represents joint torque and e represents position deviation, $$\tau = J^\# \cdot \left( \frac{\partial^2 x}{\partial t^2} + K_D \cdot \frac{\partial e}{\partial t} + K_P \cdot e - \frac{\partial J}{\partial t} \cdot \frac{\partial q}{\partial t} \right) + \\ (I - J^\# \cdot J) \cdot \frac{\partial^2 q}{\partial t^2} \cdot \phi + h\left(q, \frac{\partial q}{\partial t}\right) + g(q)$$ (Formula 7)

is derived,
where, KP represents control quantity proportional gain, KD represents control quantity differential gain, e represents a position deviation calculated from a command value and a state quantity, φ represents a control parameter for weighting the above-mentioned redundancy, and h(*,*), g are the parameters described earlier.

$$\phi = -\left( K_{NULL} \cdot \frac{\partial q}{\partial t} + \frac{\partial (I - J^\# \cdot J)}{\partial t} \cdot \frac{\partial q}{\partial t} \right)$$ (Formula 8)

is derived, where $K_{NULL}$ represents a coefficient to be used by the control computing section 42.

With Formula 7, a joint torque τ can be determined by applying various computational processing results obtained by the kinematics computing section 41, the dynamics computing section 43 and the control computing section 42 shown in FIG. 17.

With Formula 8, values other than $K_{NULL}$ are computational results obtained by the kinematics computing section 41.

Meanwhile, when inserting the insertion portion 9 of the endoscope 2 configured as described above into a body cavity, in order to prevent the bending portion 14 from becoming a rigid body, the entire bending portion is desirably provided with flexible dynamic characteristics. To this end, the insertion portion driving mechanism 20 achieves such dynamic characteristics by providing the distal end portion thereof with a combination of a spring 20a and a damper 20b such as those shown in FIG. 22.

Figure 22:
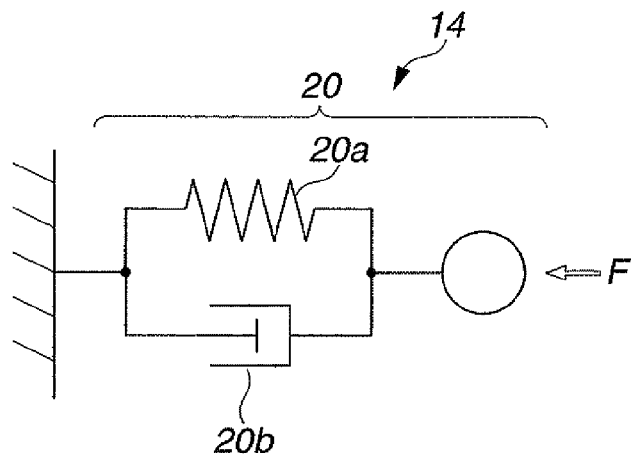
FIG. 22 relates to a first embodiment of the present invention and is an explanatory diagram showing physical properties of an insertion portion upon insertion of the same.
Figure 23:
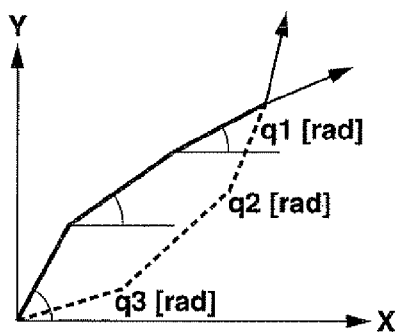
FIG. 23 relates to a first embodiment of the present invention and is an explanatory diagram showing attitude states of other link members when a distal end-side link is fixed.

In other words, due to a viscoelastic effect caused by the spring 20a and the damper 20b, when a force F shown in FIG. 22 is applied to the distal end portion 13 of the insertion portion 9, the bending portion 14 will acquire flexible characteristics or, in other words, compliance characteristics.

A control law implemented by the control computing section 42 will be described below.

First, a motion equation of dynamic characteristics shown in FIG. 22 may be expressed as Formula 9.

$$F = M \cdot \frac{\partial^2 x}{\partial t^2} + D \cdot \frac{\partial x}{\partial t} + Kx \quad \text{(Formula 9)}$$

From Formula 9, if a command position of a manipulator end-point is represented by X, a force applied to the end-point by $F_{TIP}$, and a position occurring as a result thereof by $X_D$, the dynamic characteristics of the distal end having compliance characteristics may be expressed as Formula 10.

$$M \cdot \frac{\partial^2 X}{\partial t^2} + D \cdot \frac{\partial (X - X_D)}{\partial t} + K \cdot (X - X_D) = F_{TIP} \quad \text{(Formula 10)}$$

In this case, a joint force $\tau_F$ equivalent to and opposing $F_{TIP}$ may be expressed as Formula 11.

$$\tau_F = J^T(q) \cdot F \quad \text{(Formula 11)}$$

For simplicity, a motion equation when an external force F is applied from the exterior environment in a state where the distal end portion is immobilized may be expressed with respect solely to a distal end portion mass M as Formula 12.

$$H(q) \cdot \frac{\partial^2 q}{\partial t^2} + h\left(q, \frac{\partial q}{\partial t}\right) + g(q) = \tau + J(q)^T \cdot F \quad \text{(Formula 12)}$$

As described above, Formula 14a and Formula 14b may be derived as manipulator motion equations from Formula 13.

$$\frac{\partial X}{\partial t} = J(q) \cdot \frac{\partial q}{\partial t} \quad \text{(Formula 13)}$$

$$\frac{\partial^2 X}{\partial t} = \frac{\partial J}{\partial t} \cdot \frac{\partial q}{\partial t} + J(q) \cdot \frac{\partial^2 q}{\partial t^2}$$

$$\tau = h\left(q, \frac{\partial X}{\partial t}\right) + g(q) - \quad \text{(Formula 14a)}$$

$$H(q) \cdot J(q)^{-1} \cdot \frac{\partial J}{\partial t} \cdot \frac{\partial q}{\partial t} - H(q) \cdot J(q)^{-1} \cdot$$

$$M(q)^{-1} \cdot \left(D \cdot \frac{\partial (X - X_D)}{\partial t} + K \cdot (X - X_D)\right) +$$

$$(H(q) \cdot J(q)^{-1} \cdot M(q)^{-1} - J(q)^{-1}) \cdot F$$

$$M(q) = (J(q)^{-1})^T \cdot (J_0(q) \cdot R(q)) \cdot (J(q)^{-1}) \quad \text{(Formula 14b)}$$

When manipulator dynamics including parameters of each link is once again described, compliance characteristics may be expressed as Formula 15.

$$M(q) \cdot \frac{\partial^2 X}{\partial t^2} + D \cdot \frac{\partial (X - X_D)}{\partial t} + K \cdot (X - X_D) = K_F F \quad \text{(Formula 15)}$$

Assigning Formula 15 to Formula 14a results in Formula 16.

$$\tau = h\left(q, \frac{\partial X}{\partial t}\right) + g(q) - H(q) \cdot J(q)^{-1} \cdot \frac{\partial J}{\partial t} \cdot \frac{\partial q}{\partial t} - \quad \text{(Formula 16)}$$

$$J^{-T}(q) \cdot D \cdot \frac{\partial (X - X_D)}{\partial t} + K \cdot (X - X_D) - (K_F - I) \cdot F$$

Formula 16 expresses the same relationship as Formula 7, albeit in a different form. In this case, for simplicity, a controlling expression of a torque command where the distal end portion has spring characteristics K is derived.

With Formula 16, since the first and second terms of the right hand-side of Formula 17 presented below can be omitted when velocity is low, Formula 17 is derived. Further assuming that D=0, $K_F$=I, and a distal end displacement $\Delta X$=(X−$X_D$) is relatively small, $\Delta X$=J(q)·Δq is approximately true.

As a result, Formula 18 is derived. Formula 18 indicates what kind of a torque command was created by each joint when K is set as desired compliance characteristics.

$$\tau = -J(q)^T \cdot D \cdot \frac{\partial (X - X_D)}{\partial t} + K \cdot (X - X_D) - (K_D - I) \cdot F \quad \text{(Formula 17)}$$

$$\tau = -J(q)^T \cdot K \cdot J(q) \Delta q \quad \text{(Formula 18)}$$

From the above, with respect to Formula 7 and Formula 16, generally speaking, it may be understood that the first item of the left-hand side of Formula 4 represents a movement of a hand-held position while the second term thereof represents a movement of a joint.

Then, the command control section 5A of the controller 5 performs torque calculations in real-time using Formula 7 and Formula 8, as described above. However, computational processing based on an algorithm for drive controlling the driving section 10b may be performed on a value corresponding to the second term of the Formula 7 as a result of computational processing of weighting in accordance with a movable range of the link member 21a.

Figure 24:
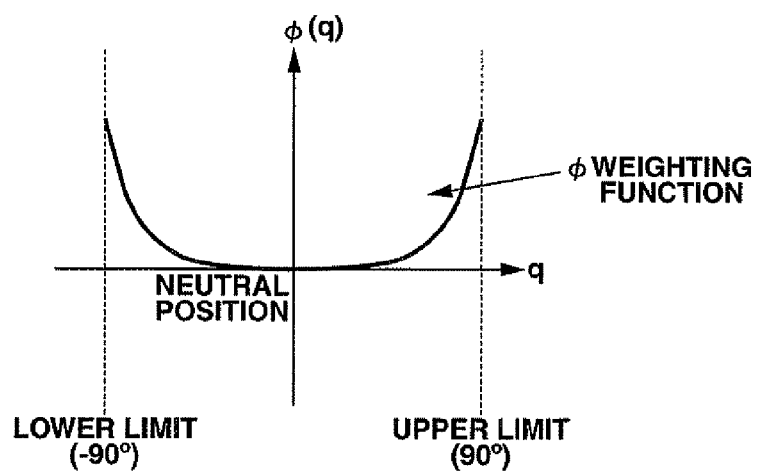
FIG. 24 relates to a first embodiment of the present invention and is a graph showing an example of a weighting function that is a coefficient for obtaining an optimum joint torque command value signal.

Accordingly, computational processing is performed by changing the algorithm of the second term of Formula 7 or $(I-J^{\#} \cdot J) \cdot (d^2 q/dt^2)$ to, for example a weighting function φ that is a parameter like that shown in FIG. 24. In other words, the weighting function φ performs computational processing such that, when determining an angle of each link member 21a, weighting increases at the limit of the movable range of each link and decreases in the vicinity of a neutral position in the movable range. Therefore, the coefficient is for setting weighting of the attitude of each link to an attitude that is as close to neutral as possible, and for eliminating forced attitudes and limiting movement to a mobile range.

For example, a range of ±90 degrees is set in advance as a tolerable range of an angle formed by adjacent link members 21a. In other words, the parameter is arranged so that the angle formed by adjacent link members 21a does not assume an acute angle.

Consequently, it is possible to perform attitude control so that each link member 21a of the insertion portion driving mechanism 20 is mobile and smooth.

For the weighting function φ, weighting functions such as those represented by any of the graphs shown in FIGS. 25 to 29 to be described later may be used. The ordinates of FIGS. 25 to 29 indicate $K_{NULL}$ as expressed in Formula 8, while abscissas thereof indicate a movable range of each link member 21a (a detected angle of each link member 21a). The positive movable limit value is set to 90 degrees and the negative movable limit value is set to −90 degrees.

Figure 25:
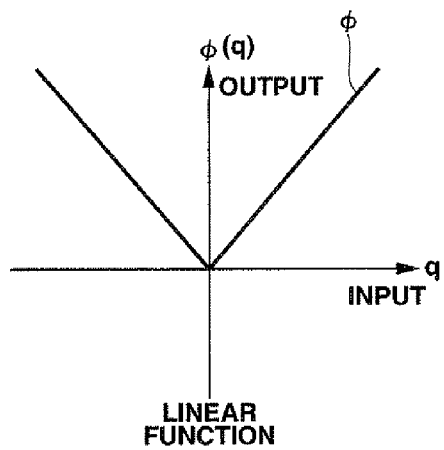
FIG. 25 relates to a first embodiment of the present invention and is a graph showing characteristics of a first variation of the weighting function.

FIG. 25 is a graph showing characteristics of a first variation of the weighting function φ. As shown in FIG. 25, the weighting function φ is a linear function, and is a weighting function obtained by performing computational processing corresponding to position variations of each link member 21a as shown below.

$$\phi = a \cdot |(q_i - q_{i\_org})|, \quad \text{(Formula 19)}$$

where α represents a negative definite value, qi represents each link position, and qi_org represents a link origin position.

Figure 26:
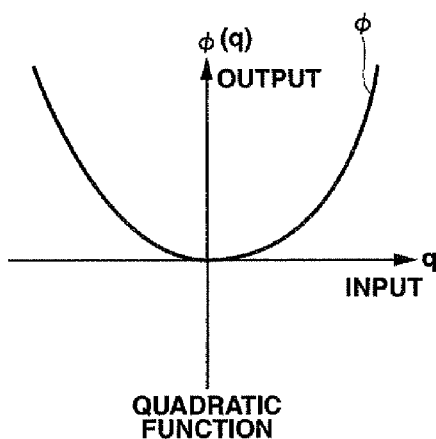
FIG. 26 relates to a first embodiment of the present invention and is a graph showing characteristics of a second variation of the weighting function.

FIG. 26 is a graph showing characteristics of a second variation of the weighting function φ. As shown in FIG. 26, the weighting function φ is a quadratic function, and is a weighting function obtained by performing computational processing corresponding to position variations of each link member 21a as shown below.

$$\phi = a \cdot (q_i - q_{i\_org})^2, \quad \text{(Formula 20)}$$

where, in this case, α represents a negative definite value.

Figure 27:
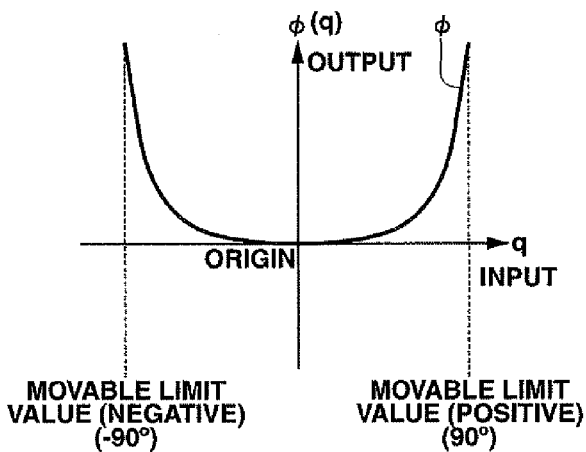
FIG. 27 relates to a first embodiment of the present invention and is a graph showing characteristics of a third variation of the weighting function.

FIG. 27 is a graph showing characteristics of a third variation of the weighting function φ. As shown in FIG. 27, the weighting function φ is a weighting function obtained by performing computational processing of partial differentiation corresponding to position variations of each link member 21a as shown below.

$$\phi = a \sum_{i=1}^{n} \partial W_i / \partial q_i \quad \text{(Formula 21)}$$

where, $W_i = (q_i - q_{i\_org})/(q_i \max - q_i \min)^2$

In this case, α represents a negative definite value, qi represents each link position, qi_org represents a link origin position, qi_max represents a link upper limit angle value, and qi_min represents a link lower limit angle value.

Figure 28:
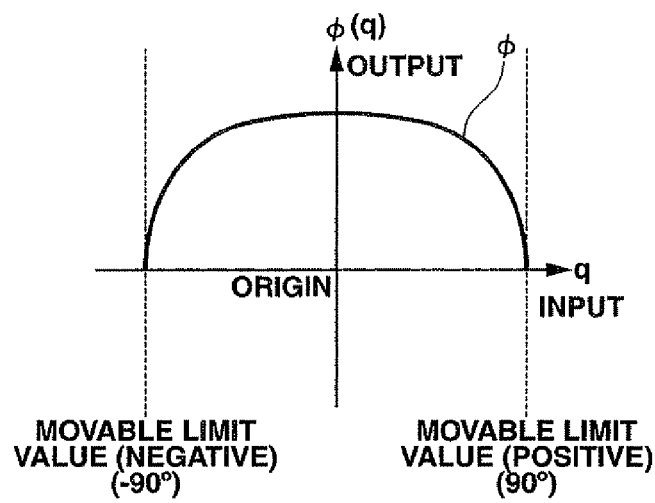
FIG. 28 relates to a first embodiment of the present invention and is a graph showing characteristics of a fourth variation of the weighting function.

FIG. 28 is a graph showing characteristics of a fourth variation of the weighting function φ. As shown in FIG. 28, in some cases, conversely to the weighting function shown in FIG. 27, the weighting function shown in FIG. 28 can be realized as a weighting function that approaches as much as possible the vicinity of the movable limit value by adding an offsetting value of φ to Formula 22, to be described below, to newly set φ and assuming α to be a positive definite value. In this case, α represents a positive definite value.

Figure 29:
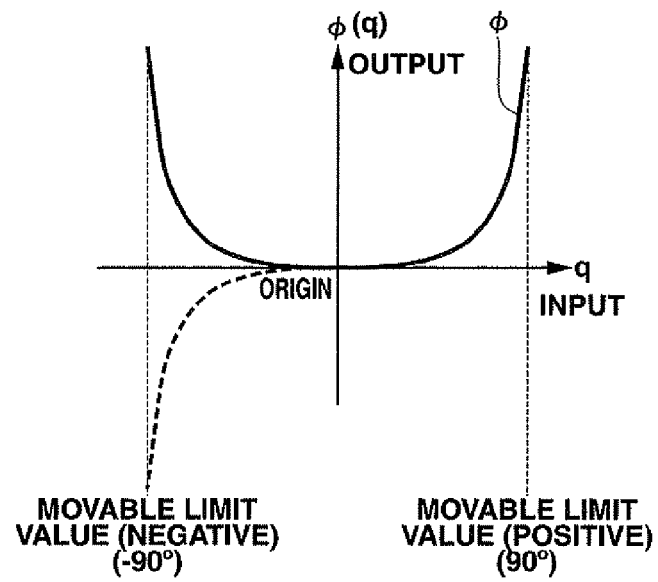
FIG. 29 relates to a first embodiment of the present invention and is a graph showing characteristics of a fifth variation of the weighting function.

FIG. 29 is a graph showing characteristics of a fifth variation of the weighting function φ. As shown in FIG. 29, to achieve the same effects as the fourth variation, the weighting function φ may also be arranged to use an absolute value of a trigonometrical function such as that including the dashed line portion shown in the diagram as expressed by Formula 22.

$$W_i = a \cdot \tan(q_i - q_{i\_org}), \quad \text{(Formula 22)}$$

where, in this case, α represents a negative definite value.

Consequently, by performing computational processing using the weighing function φ represented by any of the graphs shown in FIGS. 25 to 29, it is now possible to eliminate forced attitudes and acquire an angle that enables movement within a mobile range for each link member 21a.

In the present embodiment, instead of performing weighting on each link member 21a, it is also possible to perform weighting on the entire manipulator 20 to eliminate forced attitudes and enable movement within a mobile range.

In such a case, for the weighting function φ, a weighting function that uses a singularity of the manipulator attitude is used. In other words, a manipulability indicator M with respect to the Jacobian J may be defined as shown in Formula 23 below, whereby the manipulability indicator M may be replaced with the weighting function φ.

$$M := \sqrt{|J \cdot J^T|} \quad \text{(Formula 23)}$$

Calculating the eigenvalue of $J \cdot J^T$ produces the schema expressed by Formula 24.

(Schema)

$$J + J^T = \boxed{J} \boxed{J^T} \boxed{\phantom{X}} \Rightarrow \boxed{\diagdown} \quad \text{(Formula 24)}$$

In other words, as expressed by Formula 23 and Formula 24, a calculation of the eigenvalue of $J \cdot J^T$ normally results in: order of matrix $J \cdot J^T$=Rank (i). However, a case of a singular attitude results in: order of matrix $J \cdot J^T$<Rank (i), thereby decreasing matrix M. Accordingly, by performing computational processing using the manipulability indicator M instead of the weighting function φ, it is possible to perform weighting on the entire manipulator 20 instead of on each link member 21a so that forced attitudes can be eliminated and movements can be performed within a mobile range. In this case, the respective link members 21a are not uniformly controlled.

While weighting functions for several types of attitude control have been shown, in some cases, weighting functions can be combined so that different weighting combinations are selectively performed for each link interval using shaft switching section to be described later.

In this case, weighting functions shown in FIGS. 25 to 29 or weighting functions using a manipulability indicator M such as those expressed by Formula 23 or Formula 24 can be stored for each table. Subsequently, the controller 5 (more specifically, the CPU 32) selects a weighting function based on any one of a plurality of tables, and performs computational processing of an angle of each link member 21a or each angle of each link member with respect to the entire manipulator.

Next, a first embodiment of a controller 5 that performs attitude driving control of the aforementioned bending portion 14 will be described with reference to FIGS. 30 to 38.

Figure 30:
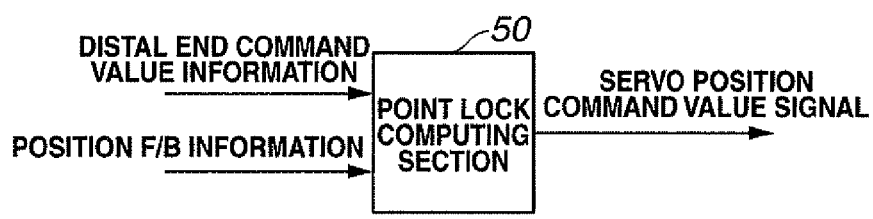
FIG. 30 relates to a first embodiment of the present invention and is a block diagram showing a specific configuration of a controller 5 of an endoscope apparatus 1.
Figure 31:
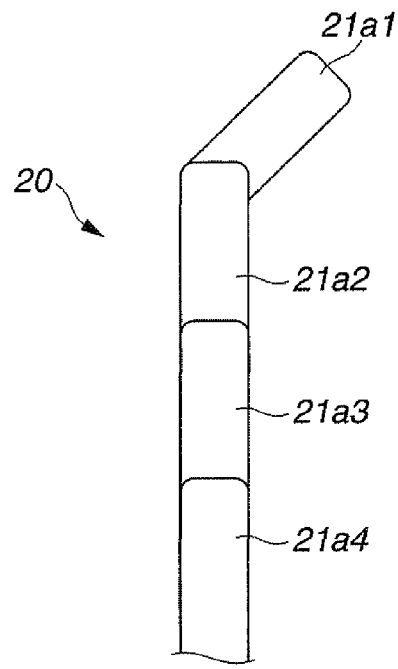
FIG. 31 relates to a first embodiment of the present invention and is an explanatory diagram for explaining attitude control of an insertion portion driving mechanism section and which shows a state in which a distal end-side link member is point-locked.
Figure 32:
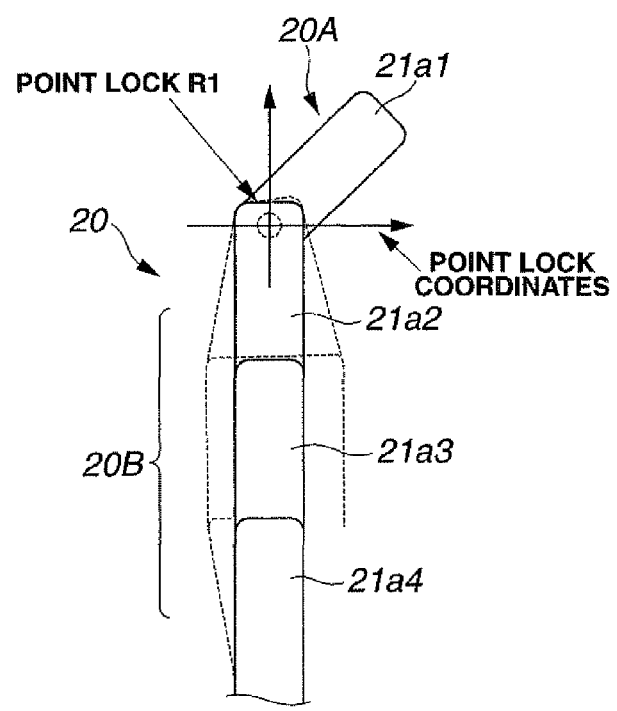
FIG. 32 relates to a first embodiment of the present invention and is an explanatory diagram showing a state in which point-locking the distal end-side link member provides a subsequent-stage link member with redundancy.
Figure 33:
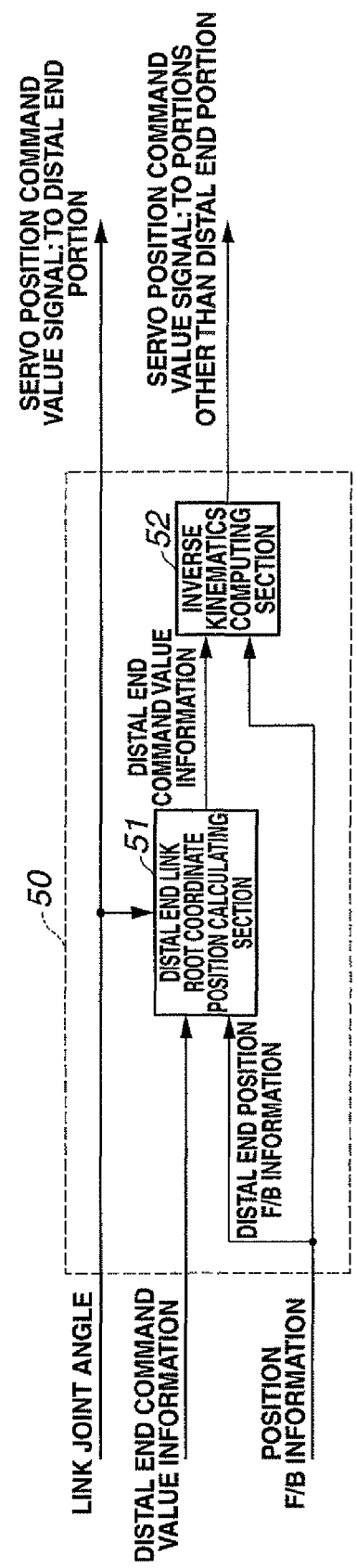
FIG. 33 relates to a first embodiment of the present invention and is a block diagram showing a specific configuration of the point lock computing section shown in FIG. 30.
Figure 34:
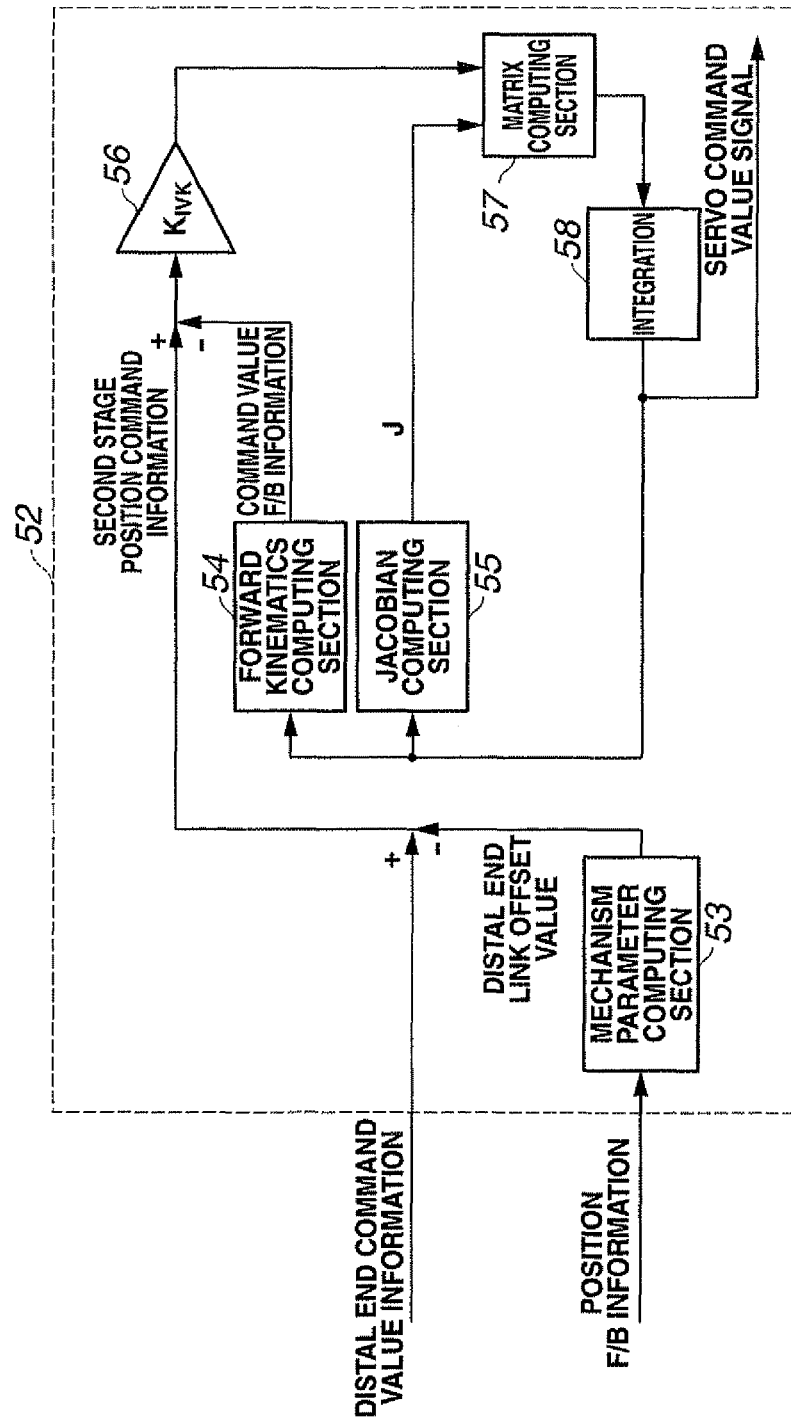
FIG. 34 relates to a first embodiment of the present invention and is a block diagram showing a specific configuration of the inverse kinematics computing section shown in FIG. 33.
Figure 35:
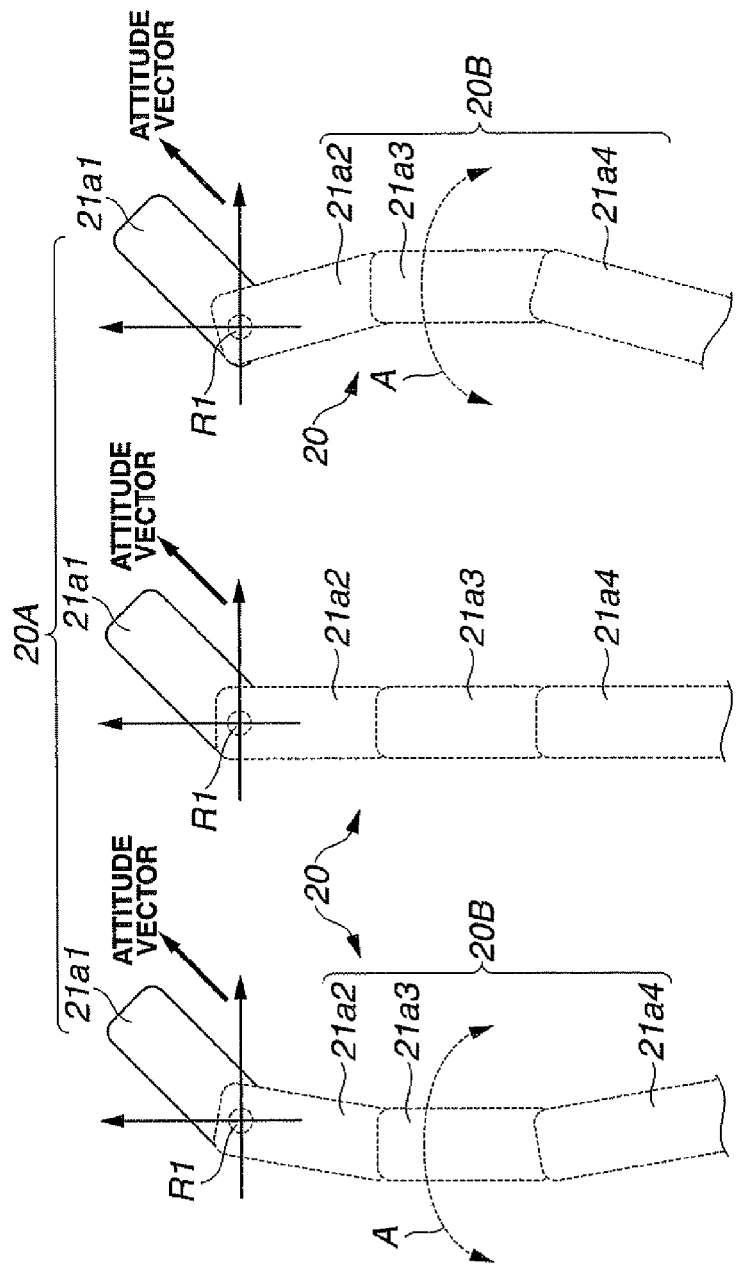
FIG. 35 relates to a first embodiment of the present invention and is a diagram explaining attitude control when only the distal end-side link member is point-locked.
Figure 36:
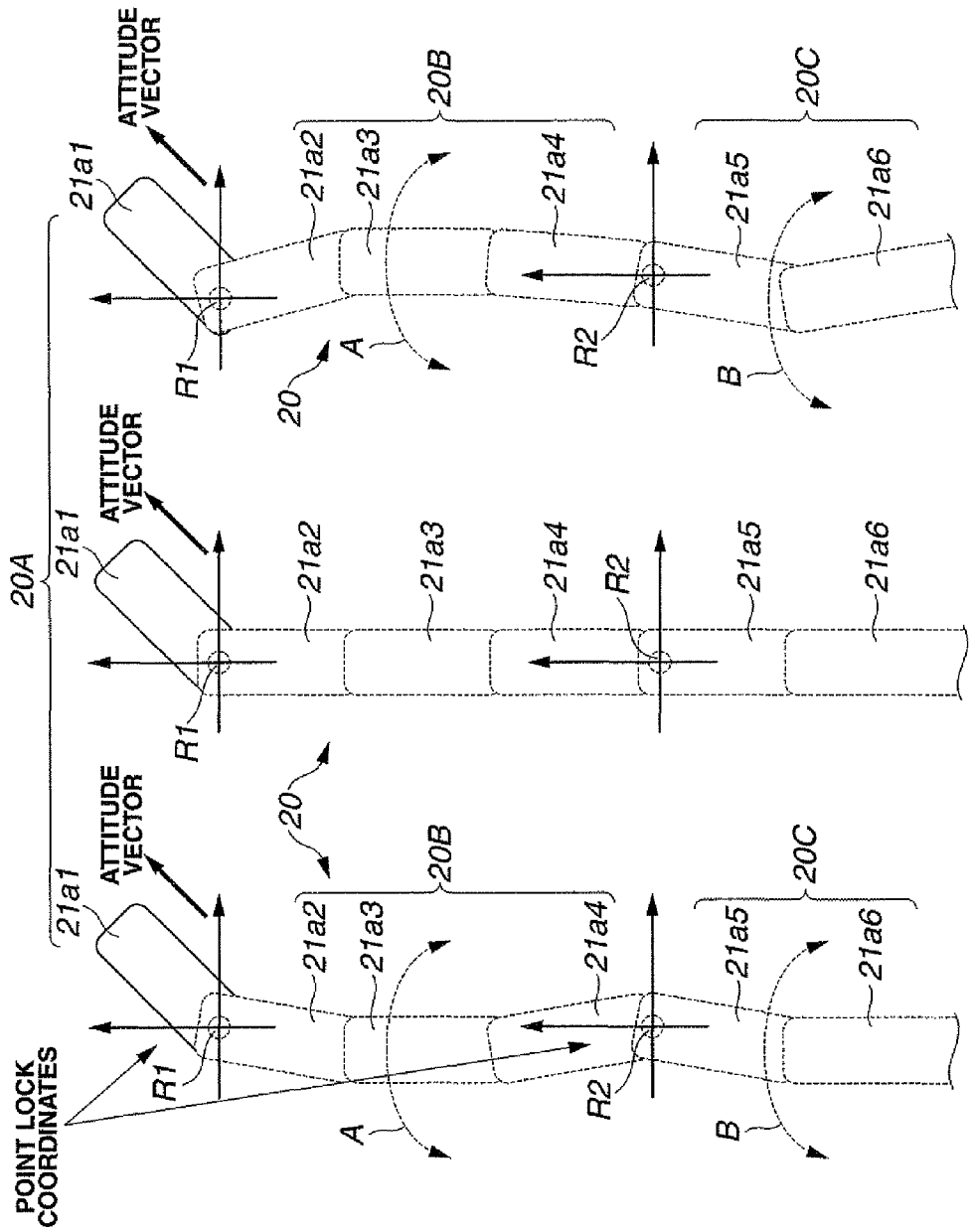
FIG. 36 relates to a first embodiment of the present invention and is an explanatory diagram explaining attitude control when a fourth link member is further point-locked.
Figure 37:
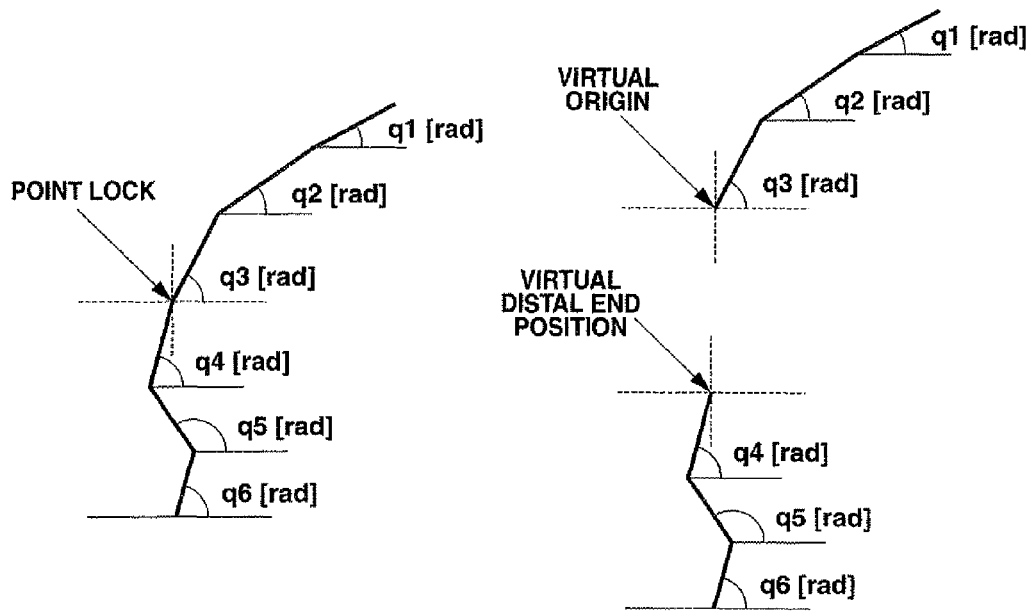
FIG. 37 relates to a first embodiment of the present invention and is an explanatory diagram explaining attitude control in a case where two locations are point-locked.
Figure 38:
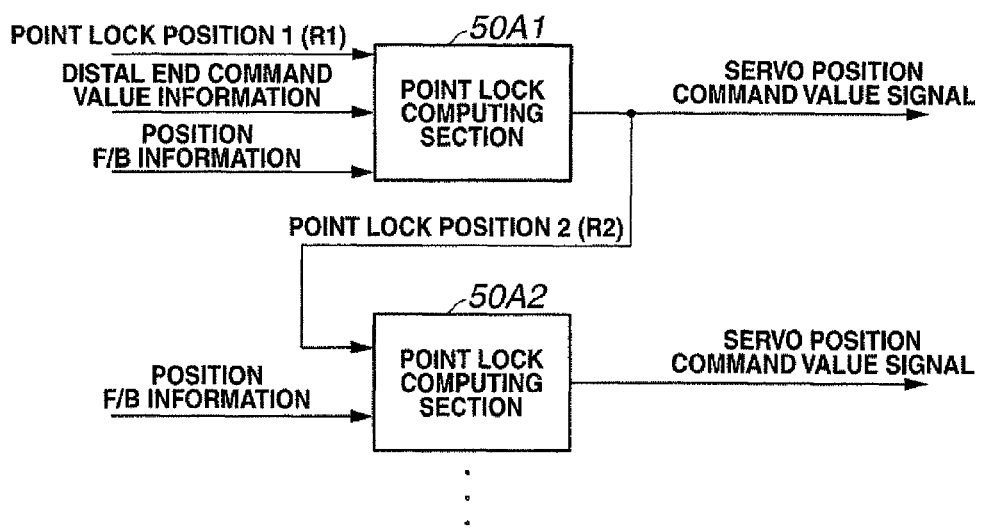
FIG. 38 relates to a first embodiment of the present invention and is a block diagram showing an internal configuration of a controller in which a point lock computing section is provided at each link member 12.

FIGS. 30 to 38 are related to the first embodiment of the present invention. FIG. 30 is a block diagram showing a specific configuration of the controller 5 of the endoscope apparatus 1; and FIGS. 31 and 32 are diagrams describing attitude control of the insertion portion driving mechanism 20 that constitutes the bending portion 14, wherein FIG. 31 shows a state in which a distal end-side link member 21a1 is point-locked, and FIG. 32 shows a state in which point-locking the distal end-side link member 21a1 provides a subsequent-stage link member with redundancy. In addition, FIG. 33 is a block diagram showing a specific configuration of the point lock computing section 50 shown in FIG. 30; FIG. 34 is a block diagram showing a specific configuration of the inverse kinematics computing section 52 shown in FIG. 33; FIG. 35 is a diagram explaining attitude control when only the distal end-side link member 21a1 is point-locked; and FIG. 36 is an explanatory diagram explaining attitude control when a fourth link member 21a4 is further point-locked. Furthermore, FIG. 37 is an explanatory diagram explaining attitude control in a case where two locations are point-locked; and FIG. 38 is a block diagram showing an internal configuration of a controller in which the point lock computing section is provided at each link member 21a.

The controller 5 according to the present embodiment includes the servo controller 36A that performs attitude control of the bending portion 14 as described earlier. The servo controller 36A is provided with a point lock computing section 50 having computational processing functions of the control law computing section 36B.

When movement occurs due to the insertion of the bending portion 14, the servo controller 36 uses the point lock computing section 50 to compute respective angles of the plurality of link members 21a so that a position and a direction designated by the operation command section 7 is maintained when a link member 21a1 designated by the operation command section 7 as well as other link members 22 contiguous to the link member 21a1 pass through the position, and based on the computation results, controls the driving section 10b to rotationally move the plurality of link members 21a.

In the present embodiment, the servo controller 36 is also arranged so that when performing computational processing for determining the respective angles of the plurality of link members 21a using the point lock computing section 50, computational processing is performed by manually or automatically selecting any of respective tables storing weighting functions having characteristics such as those shown in FIGS. 25 to 29 and by using a weighting function based on the table.

A configuration of the point lock computing section 50 that performs such computational processing will now be described with reference to FIGS. 30, 33 and 34.

As shown in FIG. 30, distal end command value information such as a setting command value signal and the like including a servo command value signal at the distal end-side link member 21a1 and position F/B information such as a state quantity detection signal at the distal end-side link member 21a1 are supplied to the point lock computing section 50.

Based on the supplied distal end command value information and position F/B information, the point lock computing section 50 performs computational processing at a distal end link root coordinate position calculating section 51 and an inverse kinematics computing section 52, to be described later, for obtaining a servo position command signal (including a joint torque command value signal) as a driving command value signal corresponding to each link member 21a.

That is, when movement occurs due to the insertion of the bending portion 14, based on the supplied distal end command value information and position F/B information, the point lock computing section 50 computes respective angles of the plurality of link members 21a so that a position and a direction designated by the operation command section 7 is maintained when a link member 21a1 designated by the operation command section 7 as well as other link members 22 contiguous to the link member 21a1 pass through the position, and outputs the computation results as a servo position command value signal to the driving section 10b.

The distal end command value information and position F/B information used in the computational processing by the point lock computing section 40 represents an angle mutually formed by the plurality of link members 21a as well as a variation of the angle that are detected by a sensor 38 that is first detecting section.

Accordingly, as a result of the driving section 10b respectively controlling the rotational movements of link members 21a designated based on the supplied servo position command value signal, the bending portion 14 having the insertion portion driving mechanism 20 will be bent in a shape conforming to the shape of a tube cavity to which the bending portion 14 is inserted.

FIG. 31 shows a state in which only the distal end-side link member 21a1 is point-locked at an instructed predetermined attitude state.

When performing control to such an attitude state, if the joint member 21b1 of the distal end portion-side link member 21a1 is assumed to be point lock R1 as shown in FIG. 32, the point lock computing section 50 performs computational processing of point lock coordinates of the point lock R1 to create a servo position command signal necessary for performing attitude control of the two-dimensional position and direction of the distal end-side link member 21a1.

In addition, as shown in FIG. 32, with an attitude state in which the distal end-side link member 21a1 is point-locked, a link portion 20B constituted by a plurality of link members 21a2, 21a3 and 21a4 subsequent to the point lock R1 acquires redundancy through the above-described attitude control, and can now change to unregulated, arbitrary attitudes as represented by the dashed lines in the diagram.

A specific configuration of the point lock computing section 50 is shown in FIG. 33. As shown in FIG. 33, the point lock computing section 50 includes the distal end link root coordinate position calculating section 51 and the inverse kinematics computing section 52.

Joint angle information of a link member 21a, distal end command value information that is position information of the distal end-side link member 21a1, and position F/B information are inputted to the distal end link root coordinate position calculating section 51. Based on the information, the distal end link root coordinate position calculating section 51 calculates a distal end link root coordinate position of the distal end-side link member 21a1, and outputs the calculation result to the inverse kinematics computing section 52.

Distal end command value information and position F/B information from the distal end link root coordinate position calculating section 51 are inputted to the inverse kinematics computing section 52. Based on the information, the inverse kinematics computing section 52 performs computational processing of root coordinate positions of link members 21a subsequent to the distal end-side link member 21a1, and creates and outputs servo position command value signals for link members other than the distal end-side link member 21a1.

A specific configuration of the inverse kinematics computing section 52 is shown in FIG. 34. As shown in FIG. 34, the inverse kinematics computing section 52 includes: a mechanism parameter computing section 53; a forward kinematics computing section 54; a Jacobian computing section 55; a gain 56; a matrix computing section 57; and an integrating circuit 58. The mechanism parameter computing section 53 performs computational processing based on the position F/B information to create a distal end link offsetting value for adjusting and controlling the distal end-side link member 21a1 to a subtle attitude. A difference between the distal end link offsetting value and the distal end command value information is obtained, and a difference is once again obtained between the difference value and the command value F/B information computationally processed by the forward kinematics computing section 54. Accordingly, the difference value is supplied to the gain 56 as second-stage position command information. The gain 56 amplifies the supplied second-stage position command information and outputs the same to the matrix computing section 57.

Meanwhile, in the same manner as described with respect to FIG. 21, the Jacobian computing section 55 creates a Jacobian J by performing computational processing based on command value information, and outputs the same to the matrix computing section 57.

Based on the supplied second stage position command information, the matrix computing section 57 performs matrix computation processing for determining an attitude (angle) of a link member 21a of the second stage and thereafter corresponding to the attitude state of the link member 21a, and after performing integration processing on the obtained computation result at the integrating circuit 58, outputs the same as a servo command value signal for the second and subsequent stages to the driving section 10b.

The output of the integrating circuit 58 or, in other words, the servo command value signal for the second and subsequent stages is fed back to a deviation value of the distal end command value information and position F/B information via the Jacobian computing section 55 and the forward kinematics computing section 54. This is performed in consideration of minimizing occurrences of singular solutions when solving inverse kinematics.

Normally, solutions are analytically obtained in inverse kinematics. However, there are cases where an occurrence of a singular solution prevents a solution from being found. For this reason, instead of using inverse kinematics, a method is employed in which inverse kinematics are obtained through forward kinematics, and a structure is provided where a convergence rate is set according to a value of the gain 56.

Accordingly, a link member 21*a* of the second and subsequent stages will be controlled so as to assume subtle attitudes in conjunction with attitude control of the distal end-side link member 21*a*1.

FIG. 35 shows a bending state of the bending portion 14 on which attitude control is performed by the point lock computing section 50 according to the first embodiment.

For example, when the operator inputs an instruction to point-lock only the distal end-side link member 21*a*1 using the operation command section 7, by performing computational processing as described above, the point lock computing section 50 creates a servo position command value signal to point-lock the distal end-side link member 21*a*1 at the point lock coordinates (two-dimensional position and direction) of the point lock R1, and provides the servo position command value signal to the driving section 10*b* to control the same.

Consequently, the distal end-side link member 21*a*1 of the bending portion 14 is point-locked at the instructed attitude vector (two-dimensional position and direction) at point lock R1, as shown in FIG. 35.

At this point, as was described with reference to the block diagrams shown in FIGS. 33 and 34, since the link portion 20B constituted by the plurality of link members 21*a*2, 21*a*3 and 21*a*4 subsequent to the point lock R1 is subjected to attitude control having redundancy in conjunction with attitude control of the distal end-side link member 21*a*1 by the point lock computing section 50, an attitude thereof becomes arbitrary with respect to, for example, the direction of the arrow A shown in the diagrams.

That is, when movement occurs due to the insertion of the bending portion 14, the point lock computing section 50 computes respective angles of the plurality of link members 21*a* so that a position and a direction designated by the operation command section 7 is maintained when a link member 21*a*1 designated by the operation command section 7 as well as other link members 21*a* contiguous to the link member 21*a*1 pass through the position, and based on the computation results, controls the driving section 10*b* so as to rotationally move the plurality of link members 21*a*.

When computationally processing the respective angles of the plurality of link members 21*a*, the point lock computing section 50 performs computational processing using a weighting function based on a weighting function table designated by the setting value command section 8. Consequently, forced attitudes of the plurality of link members 21*a* or the manipulator 20 can be eliminated, an angle necessary for enabling movement in a mobile range can be acquired for each of the plurality of link members 21*a*, and based on the computation results, rotational movement of each link member 21*a* is controlled.

With the endoscope apparatus 1 as described above, when inserting the insertion portion 9 into the large intestine, the operator inserts the insertion portion 9 having the bending portion 14 via the anus. Then, when the distal end portion 14 of the insertion portion 9 reaches the sigmoid colon segment, the servo controller 36A point-locks the distal end-side link member 21*a*1 to a two-dimensional position and direction designated by the operation command section 7.

The operator then further inserts the distal end-side link portion 21*a*1 point-locked to the two-dimensional position and direction along the intestinal wall of the sigmoid colon segment.

This causes the distal end-side link member 21*a*1 and other link members 21*a* consecutive thereto to be controlled at angles that enable a position and a direction designated by the operation command section 7 to be maintained when passing the position. In other words, the bending portion 14 is to be inserted while performing bending movements so as to assume shapes conforming to the shape of the sigmoid colon segment. As for the link members 21*a*2 to 21*an* of the second and subsequent stages, attitude control having redundancy will be performed as described above.

Consequently, since insertion can now be performed in a shape conforming to the sigmoid colon segment into which insertion was conventionally difficult, it is now possible to pass through the sigmoid colon segment with ease. Therefore, since insertions into deep portions of the large intestine can be readily performed, insertability can be improved.

With the present embodiment, it is also possible to point-lock an arbitrary link member 21*a* of the second or subsequent stage instead of point-locking only the distal end-side link member 21*a*1.

FIG. 36 is a diagram showing a bending state of the bending portion 14 in a case where attitude control is performed so that there are two point-locked locations; FIG. 37 is an explanatory diagram explaining a computing method used by the point lock computing section 50 for designating two point-locked locations; and FIG. 38 is a block diagram showing a configuration of a controller required for designating and controlling a plurality of point-locked locations.

As shown in FIG. 38, in a configuration for point-locking the distal end-side link member 21*a*1 and arbitrary link members 21*a* of the second and subsequent stages, a plurality of the point lock computing sections 50 (point lock computing sections 50A1 to 50An) is provided in correspondence to the plurality of link members 21*a*, whereby the point lock computing sections 50 are connected so that a servo command value signal for obtaining a subsequent-stage point lock coordinate position is inputtable to the point lock computing section 50 of the subsequent stage.

That is, assuming that the block corresponding to the distal end-side link member 21*a*1 is the point lock computing section 50A1, the point lock computing section 50A2 corresponding to the subsequent-stage link member 21*a*2 acquires a servo position command value signal that is an output of the point lock computing section 50A1 as an input signal for computing a second point lock position.

The servo controller 36A may be configured by, in a similar manner, subsequently providing point lock computing sections 50A3 to 50An in a quantity corresponding to the number of link members 21*a* to be point-locked among the plurality of link members 21*a*.

In the configuration shown in FIG. 38, when two point lock locations are designated, computational processing is respectively performed by the plurality of point lock computing sections 50A1, 50A2, . . . , 50An to 50AN based on the position command value signal of the distal end-side link member 21*a*1.

In this case, when assuming that, in addition to the point lock R1, the second point lock location is the joint member 21*b*3 of the third link member 21*a*3, the point lock location of the joint member 21*b*3 (q3) is assumed to be a virtual distal end position, as shown in FIG. 37. In other words, a link member 21a corresponding to q4 that has q3 as a virtual distal end position becomes the virtual distal end-side link member 21a.

Then, computational processing is performed by the corresponding point lock computing section 50 so as to perform point-lock at an attitude vector (two-dimensional or three-dimensional position and direction) of q4 of the link member 21a, Consequently, it is now possible to perform computational processing necessary for performing point lock at the two locations q1 and q4 of the distal end-side link member 21a1.

Designation of a link member 21a to be point-locked among the plurality of link members 21a is to be performed at the operation command section 7.

FIG. 36 shows a bending state of the bending portion 14 in a case where attitude control is performed so that there are two point-locked locations.

As shown in FIG. 36, for example, when the operator inputs an instruction for point-locking the distal end-side link member 21a1 and the fourth-stage link member 21a4 at a two-dimensional position and direction using the operation command section 7, by performing computational processing such as that described above, the point lock computing sections 50A1 and 50A4 (the point lock computing section corresponding to the fourth-stage link member 21a4, not shown) respectively create a servo position command value signal for point-locking the distal end-side link member 21a1 and the fourth-stage link member 21a4 at point lock coordinate values of point lock R1 and point lock R2, and provide the signals to the driving section 10b to control the same.

Consequently, as shown in FIG. 36, the distal end-side link member 21a1 of the bending portion 14 is point-locked at the instructed attitude vector (two-dimensional position and direction) at point lock R1. At the same time, the fourth-stage link member 21a4 is point-locked at the instructed attitude vector (two-dimensional position and direction) at point lock R1.

At this point, as was described with reference to the block diagrams shown in FIGS. 33 and 34, since the link portion 20B constituted by the plurality of link members 21a2 and 21a3 subsequent to the point lock R1 and a link member 20C constituted by the plurality of link members 21a5 and 21a6 subsequent to the point lock R2 are subjected to attitude control having redundancy in conjunction with attitude control of the distal end-side link member 21a1 by the point lock computing section 50, an attitude thereof becomes arbitrary with respect to, for example, the direction of an arrow A shown in the diagrams.

That is, when movement occurs due to the insertion of the bending portion 14, the point lock computing sections 50A1 and 50A2 compute respective angles of the plurality of link members 21a so that the position and a direction designated by the operation command section 7 are maintained when link members 21a1 and 21a4 designated by the operation command section 7 as well as other link members 21a respectively contiguous to the link members 21a1 and 21a4 pass through the position, and based on the computation results, controls the driving section 10b so as to rotationally move the plurality of link members 21a.

With the endoscope apparatus 1 as described above, when inserting the insertion portion 9 into the large intestine, the operator inserts the insertion portion 9 having the bending portion 14 via the anus. Then, when the distal end portion 14 of the insertion portion 9 reaches the sigmoid colon segment, the servo controller 36A point-locks the distal end-side link member 21a1 to a two-dimensional position and direction designated by the operation command section 7.

The operator then further inserts the distal end-side link portion 21a point-locked to the two-dimensional position and direction along the intestinal wall of the sigmoid colon segment.

This causes the distal end-side link member 21a1 and other link members 21a consecutive thereto to be controlled at angles enabling passage of a position designated by the operation command section 7 while maintaining the position and a direction designated by the operation command section 7.

As insertion of the bending portion 14 proceeds, the servo controller 36A point-locks the designated link member 21a4 to a two-dimensional position and direction obtained by the point lock computing section 50A5.

The operator then further inserts the intermediate link portion 21a4 point-locked to the two-dimensional position and direction along the intestinal wall of the sigmoid colon segment.

This causes the link member 21a4 and other link members 21a consecutive thereto to be controlled in the same manner as the distal end-side link member 21a1 and other link members 21a consecutive thereto at angles enabling passage of a position designated by the operation command section 7 while maintaining the position and a direction designated by the operation command section 7.

In other words, the bending portion 14 is to be inserted while performing bending movements into shapes conforming to the shape of the sigmoid colon segment. As for the link members 21a2 to 21an of the second and subsequent stages, attitude control having redundancy is performed as described above.

Consequently, when inserting the insertion portion 9 into the large intestine, since insertion can be performed in a shape more conforming to the sigmoid colon segment than a state in which the distal end-side link member 21a1 is point-locked, it is now possible to pass through the sigmoid colon segment with greater ease. Therefore, since insertions into deep portions of the large intestine can be more readily performed, insertability can be improved.

For the present embodiment, while point-locking a two-dimensional position and direction of an arbitrary link member 21a among the plurality of link members 21a has been described, the present invention is not limited to this arrangement. Instead, the present invention may be configured so that a three-dimensional position and direction of an arbitrary link member 21a are point-locked.

For the present embodiment, although a description has been given on point-locking an arbitrary link member 21a while performing attitude control of other link members 21a that allows changing into arbitrary redundant attitudes using the servo controller 36A having the point lock computing section 50, when withdrawing the insertion portion 9 from the inside of a tube cavity such as the large intestine into which the insertion portion 9 has been inserted, control may be performed so that, for example, attitude control of the entire bending portion 14 or a part of the link members 21a is released by suspending driving of the driving section 10b so that an unloaded free state (a state that enables free rotational movement) is attained. Consequently, the insertion portion 9 can be readily withdrawn from inside the tube cavity.

Figure 39:
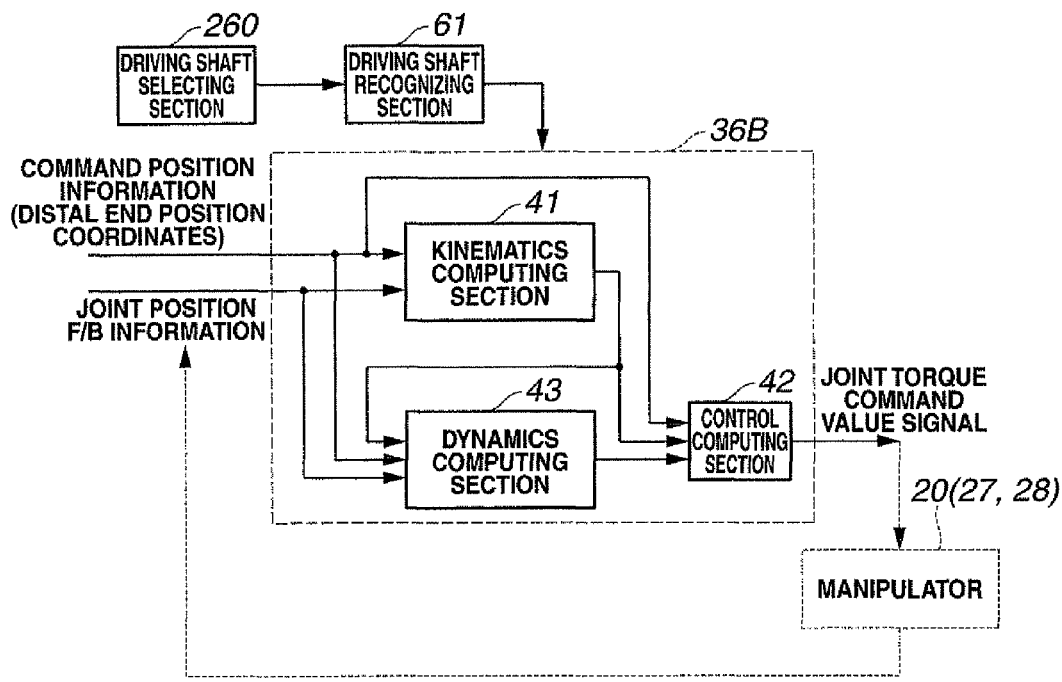
FIG. 39 relates to a first embodiment of the present invention and is a block diagram showing a configuration of a control law computing section provided with driving shaft setting section and driving shaft recognizing section.

In addition, as shown in FIG. 39, the present invention may be configured by providing driving shaft selecting section 260 and driving shaft recognizing section 61 so that a link member 21a for which attitude control is released to change to a free state is designated based on an operation by the operator.

In this case, as shown in FIG. 39, the driving shaft selecting section 260 is used by the operator to select a link member 21*a* to be changed to a free state, and the selected operation signal is supplied to the driving shaft recognizing section 61. Based on the operation signal, the driving shaft recognizing section 61 recognizes position information based on the selected link member 21*a*, and outputs a control signal declaring the intent to release attitude control of the recognized link member 21*a* to the control law computing section 36B (refer to FIG. 16).

Then, in the same manner as described above, the control law computing section 36B performs attitude control of the link member 21*a*, and at the same time, controls the driving section 10*b* so that attitude control is released for link members 21*a* based on the control signal. Consequently, the degree of freedom of the bending attitude of the bending portion 14 increases, and the manipulability of the insertion portion 9 can be farther enhanced.

As described above, according to the present embodiment, since an arbitrary link member 21*a* including the distal end-side link member among a plurality of link members 21*a* constituting the bending portion 14 of the insertion portion 9 can be point-locked, and attitude control can be performed over the other link members so that arbitrary attitudes having redundancy can be taken, it is now possible to insert the bending portion 14 of the insertion portion 9 in a shape conforming to the interior shape of a tube cavity. As a result, advantageous effects such as improvement of insertability of the insertion portion can be achieved.

In the present embodiment, there may be cases where, when the insertion portion 9 is inserted into a tube cavity and attitude control is performed as described above, it is desirable to subtly change the attitude of the point-locked distal end-side link member 21*a*1 or an arbitrary link member 21*a* other than the link member 21*a*1 without changing the attitude state.

Since matrix computation of attitudes having redundancy is being performed, a case may occur in which even a subtle movement may cause a significant change in the attitude. Therefore, this is effective when it is desirable to subtly adjust a desired link while maintaining the attitude.

Figure 40:
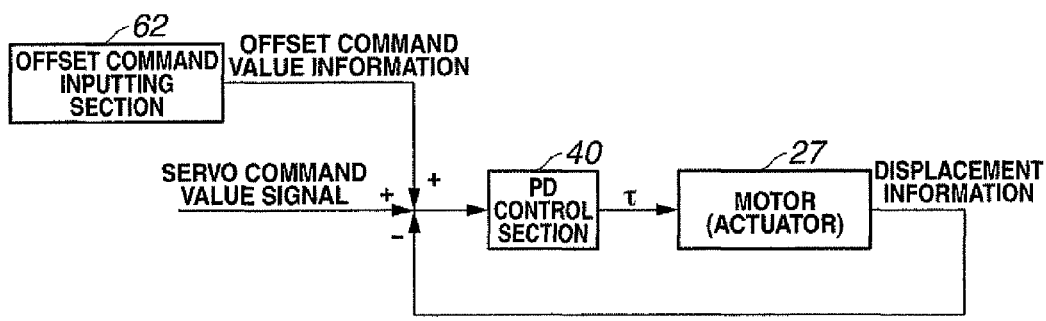
FIG. 40 relates to a first embodiment of the present invention and is a block line diagram of a servo controller including an offset command inputting section.

In order to satisfy such a demand, for example, as shown in FIG. 40, the present embodiment is provided with an offset command inputting section 62 that changes the position or direction of the point-locked distal end-side link member 21*a*1 or an arbitrary link member 21*a* other than the link member 21*a*1 by only a preset quantity. In other words, by using the offset command inputting section 6, it is now possible to adjust the point-locked distal end-side link member 21*a*1 or an arbitrary link member 21*a* other than the link member 21*a*1 by subtly changing (offsetting) the position or the direction thereof.

The offset command inputting section 62 is provided in the servo controller 36A, and creates and outputs offset command value information indicating whether an arbitrary link member 21*a* is to be offset by a preset quantity. In some cases, the setting quantity of the offset command inputting section 62 may be arranged to be variable.

As shown in FIG. 40, the offset command value information is added to a servo command value signal, and then subjected to PD control such as proportional/differential control by the PD control section 40 as was described with reference to FIG. 12 to become an operation command value signal (driving signal) to be provided to the motor 27. Consequently, since the motor 27 is rotationally controlled based on an operation output-side signal to which an offset quantity has been added, the attitude (position or direction) of the designated link member 21*a* will be subtly offset.

As a result, in the case where insertion is impeded due to the point-locked distal end-side link member 21*a*1 or an arbitrary link member 21*a* other than the link member 21*a*1 coming into contact with the intestinal wall of the sigmoid colon segment, the position or the direction of the link member 21*a* is offset. Therefore, insertion can be performed smoothly without inflicting pain on a patient.

In the present embodiment, the servo controller 36A may also be configured by combining the driving shaft selecting section 260 and the driving shaft recognizing section 61 shown in FIG. 39 with the offset command inputting section 62 shown in FIG. 40. Such a configuration is shown in FIG. 41.

Figure 41:
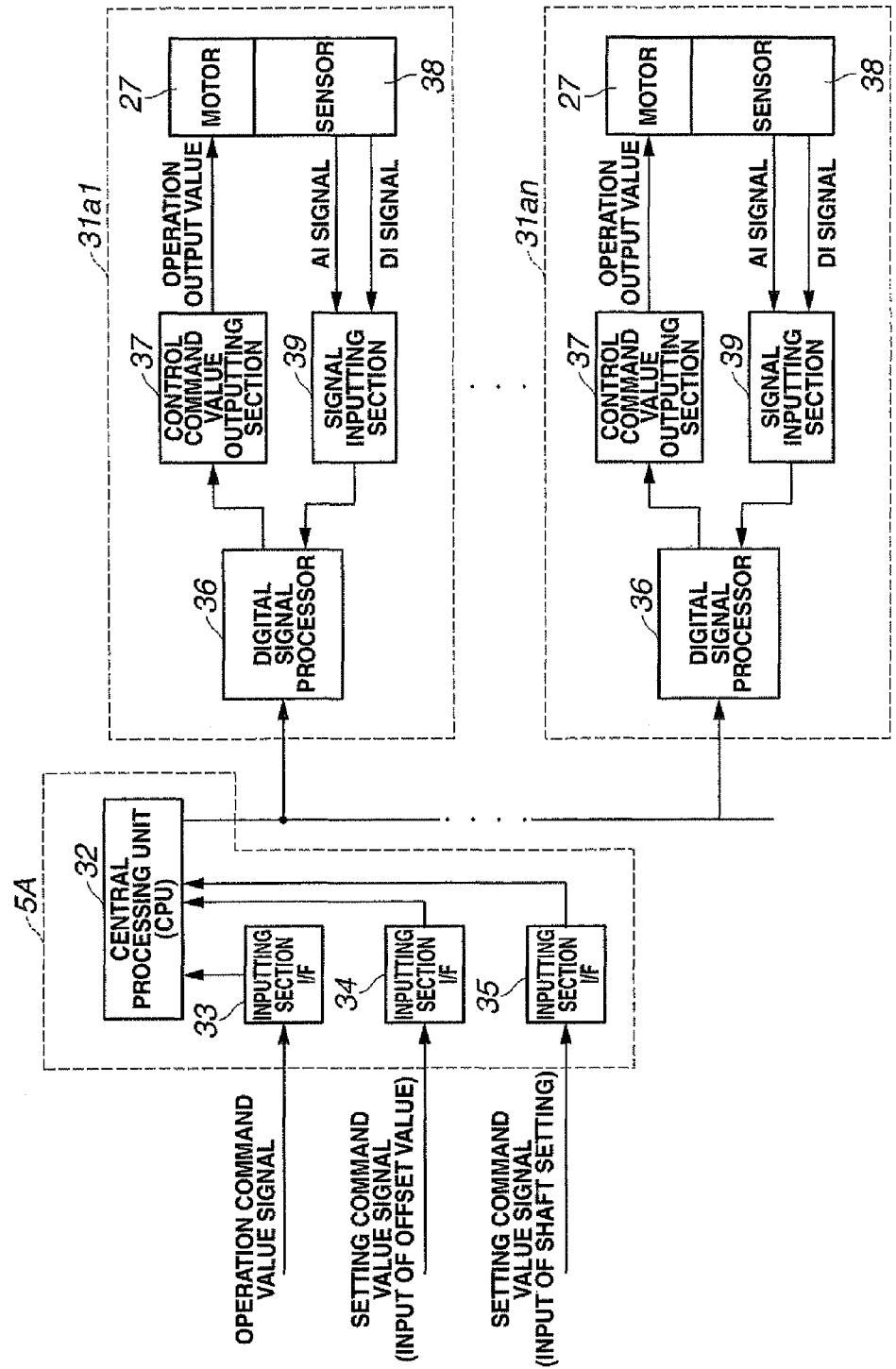
FIG. 41 relates to a first embodiment of the present invention and is a block diagram showing a servo controller in the case where the same is constituted by a combination of the driving shaft setting section and the driving shaft recognizing section shown in FIG. 39 and the offset command inputting section shown in FIG. 40.

More specifically, as shown in FIG. 41, the command control section 5A having the servo controller 36A is arranged so that offset command value information from the offset command inputting section 62 is inputted to the inputting I/F 34 while a control signal such as shaft setting information from the driving shaft recognizing section 61 is inputted to the inputting I/F 35. Based on the information, the CPU 32 is to perform computational processing for controlling the attitude of each link member of the bending portion 14. Other configurations and advantageous effects are the same as those of the configuration shown in FIG. 10.

For the present embodiment, while the bending portion 14 having the insertion portion driving mechanism 20 constituting a manipulator has been described as being provided at the insertion portion 9 of the endoscope 2, the bending portion 14 may be arranged to be provided at an insertion portion of an endoscope insertion aiding device that aids the insertion of the insertion portion 9 into a tube cavity by allowing insertion of the insertion portion 9 of the endoscope 2.

Figure 42:
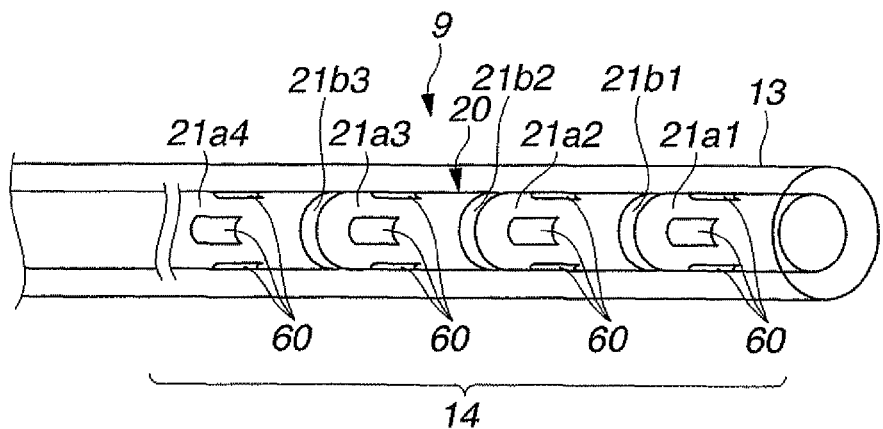
FIG. 42 relates to a second embodiment of the present invention and is a schematic configuration diagram showing a configuration of an insertion portion driving mechanism in which a load detecting section for detecting a load generated by coming into contact with an intestinal wall is provided at each link member.
Figure 43:
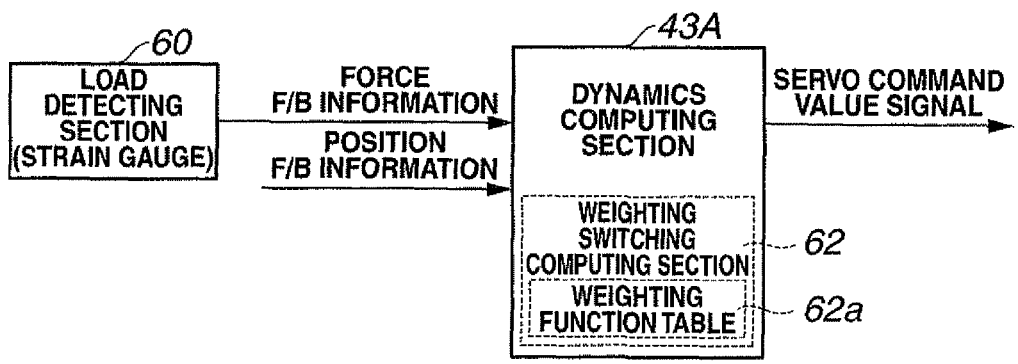
FIG. 43 relates to a second embodiment of the present invention and is a block diagram showing a dynamics computing section included in the load detecting section shown in FIG. 42 and a control law computing section 36B.
Figure 44:
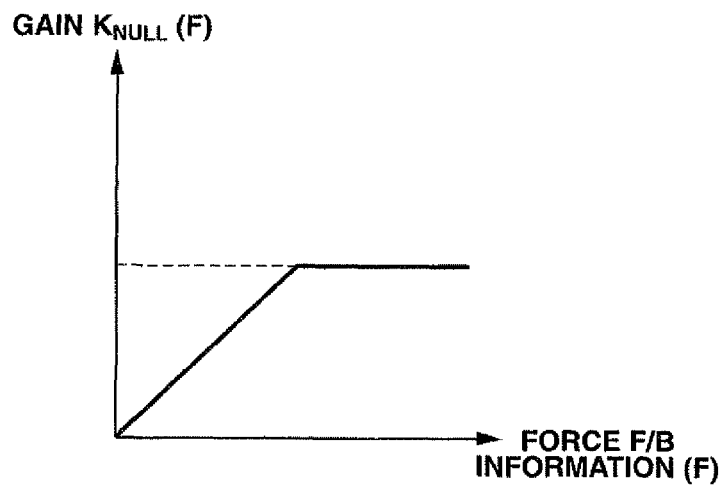
FIG. 44 relates to a second embodiment of the present invention and is a graph showing characteristics of a detection result from the load detecting section and a coefficient that determines a weighting function.
Figure 45:
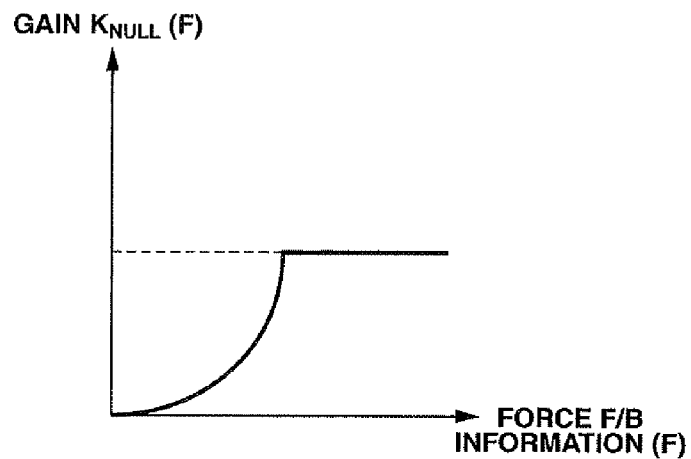
FIG. 45 relates to a second embodiment of the present invention and is a graph showing an example of characteristics that differs from those shown in FIG. 44.
Figure 46:
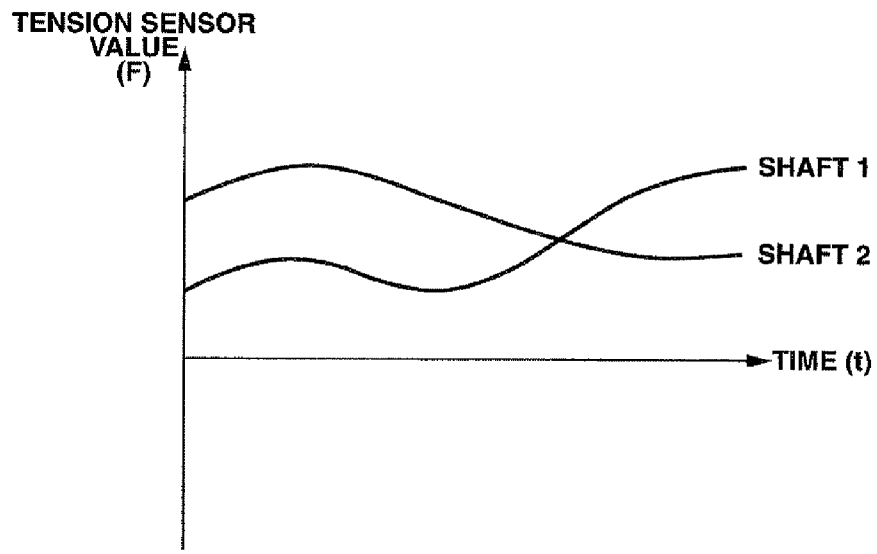
FIG. 46 represents a first variation of the second embodiment and is a graph showing characteristics of a detection result from the load detecting section and time.
Figure 47:
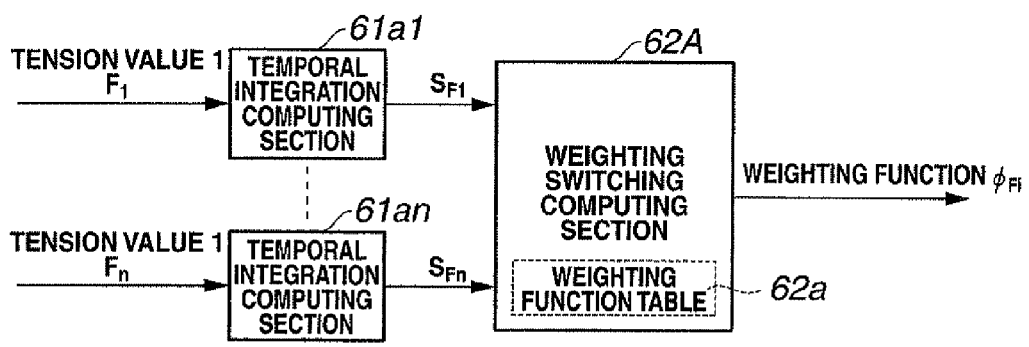
FIG. 47 is a block diagram showing a substantial block configuration for implementing the first variation of the second embodiment.
Figure 48:
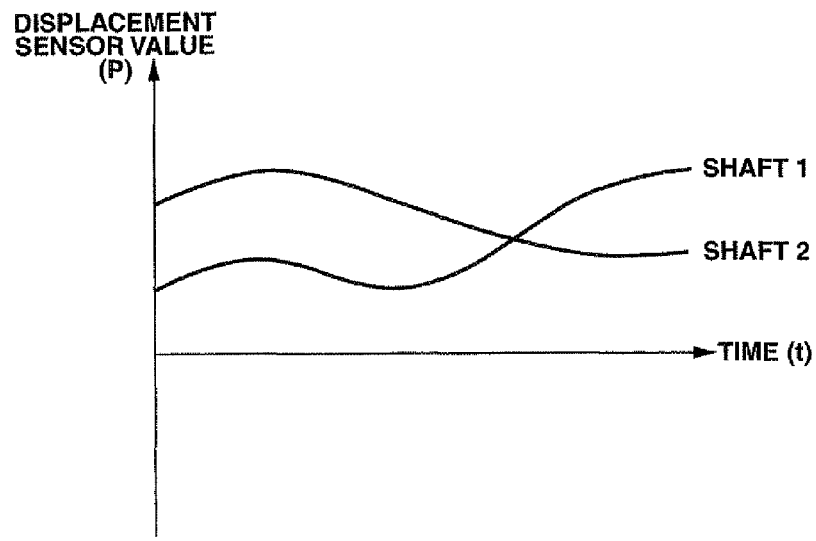
FIG. 48 represents a second variation of the second embodiment and is a graph showing characteristics of a detection result from a displacement sensor used as a load detecting section and time.
Figure 49:
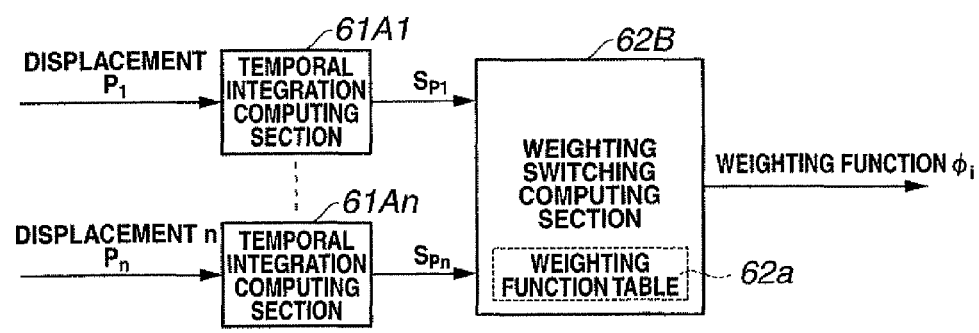
FIG. 49 is a block diagram showing a substantial block configuration for implementing the second variation of the second embodiment.

Next, a second embodiment of the present invention will be described with reference to FIGS. 42 to 49. FIG. 42 is a schematic configuration diagram showing a configuration of an insertion portion driving mechanism in which a load detecting section for detecting a load created by coming into contact with an intestinal wall is provided at each link member; FIG. 43 is a block diagram showing a dynamics computing section included in the load detecting section shown in FIG. 42 and the control law computing section 36B; FIG. 44 is a graph showing characteristics of a detection result from the load detecting section and a coefficient that determines a weighting function; and FIG. 45 is a graph showing an example of characteristics that differs from those shown in FIG. 44, FIGS. 46 and 47 present a first variation of the second embodiment, wherein: FIG. 46 is a graph showing characteristics of a detection result from the load detecting section and time; and FIG. 47 is a block diagram showing a substantial block configuration for implementing the first variation of the second embodiment. FIGS. 48 and 49 present a second variation of the second embodiment, wherein: FIG. 48 is a graph showing characteristics of a detection result from a displacement sensor used as a load detecting section and time; and FIG. 49 is a block diagram showing a substantial block configuration for implementing the second variation of the second embodiment.

The second embodiment describes specific processing for automatically determining a weighting function that is an optimum parameter based on a detection result of a load detecting section 60, to be described later, in the case where, when inserting the bending portion 14 into a tube cavity, computational processing is performed using a weighting function on angles of a plurality of link members 21 constituting the bending portion 14 or on an angle of an arbitrary link member 21 among the plurality of link members 21.

Otherwise, descriptions on points similar to the first embodiment described above will be omitted.

As shown in FIG. 42, the load detecting section 60 is respectively provided as load detecting means (second detecting section) at each link member 21a constituting the bending portion 14 of the insertion portion 9.

The load detecting section 60 is constituted using, for example, a tension sensor such as a strain gauge, and is respectively provided in a covering tube (not shown) covering each link member 21a so as to be disposed at preset locations (for example, four locations when provided every 90 degrees) on the circumferential surface of each link member 21a.

As shown in FIGS. 42 and 43, when the bending portion 14 is being inserted into a tube cavity, the load detecting section 60 detects a force (also referred to as tension) created from coming into contact with the intestinal wall or the like, and outputs the detection result as force F/B information to the dynamics computing section 43A.

The dynamics computing section 43A is provided with a weighting switching computing section 62 as setting section that, based on the detection result from the load detecting section 60, creates a parameter value necessary for performing computational processing for determining a weighting function and performs computational processing of a weighting function in accordance with the parameter value.

The weighting switching computing section 62 has weighting function tables 62a respectively storing, for example, the weighting functions shown in FIGS. 25 to 29 or weighting functions using a manipulability indicator M such as those expressed by Formula 23 or Formula 24. The weighting function table 62a can also be arranged to be provided in the command control section 5A or the like instead of in the weighting switching computing section 62.

The dynamics computing section 43A causes the weighting switching computing section 62 to perform computational processing on angles of the plurality of link members 21a using a weighting function based on position F/B information that is an angular displacement of each link member 21a, and outputs a weighted servo command value signal to the driving section 10b.

In this case, the weighting switching computing section 62 creates a parameter value necessary for performing computational processing for determining a weighting function based on a detection result from the load detecting section 60.

The weighting switching computing section 62 performs computational processing using a weighting function of any of the weighting function tables 62a preset by the operation command section 7 and the created parameter value.

In other words, as expressed by Formula 25 below, $$\phi = \left\{ -K_{NULL}(F) \cdot \left(\frac{\partial q}{\partial t}\right) + \left(\frac{\partial (I - J^{\#} \cdot J)}{\partial t}\right)\left(\frac{\partial q}{\partial t}\right) \right\} \quad \text{(Formula 25)}$$

the weighting switching computing section 62 determines $K_{NULL}$ that is a parameter value from a change in (F) that is a detection result from the load detecting section 60 expressed in Formula 25.

An example of characteristics of the parameter value is depicted in the graph shown in FIG. 44.

As shown in FIG. 44, $K_{NULL}$ that is the parameter value increases until the value of the force F/B information reaches a presetting value, and consistently takes a constant value after the setting value. In other words, $K_{NULL}$ gain changes linearly in accordance with the force F/B information, and becomes a parameter value that saturates at a preset arbitrary threshold. The setting value of the threshold of the parameter value $K_{NULL}$ can also be inputted via the setting value command section 8.

As seen, in the vicinity of the bending portion 14, a weighting function value $\phi$ is attained that realizes an attitude not subjected to the action of disturbance with respect to disturbances such as coming into contact with the intestinal wall.

While there are cases where, besides the linear weighting function parameter described above, it is desirable to cancel out non-linear components that occur due to sensor characteristics, sensor implementation or the like, or to intentionally arrange attitudes of movement to be non-linear. As an example thereof the weighting function parameter value $K_{NULL}$ may take the form of non-linear functions expressed by Formula 26 and Formula 27 below.

If a gain maximum value of $K_{NULL}$ that is a parameter value may be represented by $K_{NULLMAX}$ and the force F/B information by (F), $$K_{NULL}(F)=\tan(F) \ (0 \leq <F \leq \beta) \quad \text{(Formula 26)}$$

$$K_{NULL}(F)=K_{NULLMAX}(\beta>F) \quad \text{(Formula 27)}$$

are derived, where $\beta>0$.

In this case, resulting characteristics of the parameter value are as depicted by the graph shown in FIG. 45.

Besides the graph characteristics shown in FIG. 45, high-dimensional functions such as expressed by Formula 28 and Formula 29 may also be used. Such Formulas 28 and 29 are provided below.

$$K_{NULL}(F)=a \cdot F^3 \ (0 \leq <F \leq \beta) \quad \text{(Formula 28)}$$

$$K_{NULL}(F)=K_{NULLMAX}(\beta>F) \quad \text{(Formula 29)}$$

are derived, where, $\beta$, $\alpha>0$ (arbitrary value).

Therefore, as described above, the weighting switching computing section 62 is capable of obtaining an optimum weighting function through computational processing performed by changing parameter values when weighting an angle of each link member 21a and performing computational processing based on force F/B information from the load detecting section 60. In other words, a servo command value signal weighted in accordance with force F/B information from the load detecting section 60 can be obtained by the dynamics computing section 43A, thereby eliminating forced attitudes of an arbitrary link member 21a or the entire manipulator 20 and enabling movements within a mobile range.

As seen, while movements at optimum attitudes are enabled using load information from the load detecting section 60, depending on the mounting arrangement of the load detecting section 60, load due to attitude change and disturbance load may be overlapped on each other. In consideration thereof, it is also possible to arrange characteristics of load that occurs due to attitude change to be stored as a parameter and known sensor characteristics in the controller 5, and acquire information on a detected disturbance by subtracting the part of the known sensor characteristics by the weighting switching computing section 62.

As for the known sensor characteristics, precise dynamics control may be implemented using force information feedback information on the state quantity detection signal by arranging as a load sensor for operating the bending portion 14.

When inserting the insertion portion 9 into a tube cavity, the endoscope apparatus 1 according to the present embodiment is capable of performing insertion in a safer manner even when the bending portion 14 of the insertion portion 9 comes into contact with the intestinal wall or the like inside the tube cavity and the contact state continues.

In other words, the present embodiment is arranged so that, when performing computational processing of weighting on angles of the plurality of link members 21a based on a detection result of the load detecting section 60, a weighting function for the entire manipulator 20 which takes time into consideration and also causes a link member 21a that is in contact with the intestinal wall or the like to avoid contact is obtained. Such variations are shown in FIGS. 46 to 49.

FIGS. 46 and 47 describe a first variation of the second embodiment, wherein: FIG. 46 is a graph showing characteristics of a detection result from the load detecting section and time; and FIG. 47 is a block diagram showing a configuration of a substantial part including the weighting switching computing section in the dynamics computing section. The ordinate shown in FIG. 46 represents a tension sensor value (force F/B information) obtained from a tension sensor (strain gauge) that is the load detecting section; the abscissa represents time (t); and axes 1 and 2 respectively indicate first and second link members 21a.

As shown in FIG. 46, during insertion of the insertion portion 9 of the endoscope apparatus 1 into a tube cavity, for example, the tension sensor value of the second link member 21a2 from the load detecting section 60 decreases as time advances, while the tension sensor value of the first (distal end-side) link member 21a1 from the load detecting section 60 increases after reaching a given predetermined point in time.

In other words, this indicates that the first link member 21a1 came into contact with the intestinal wall of the large intestine or the like at a given predetermined point in time, thereby causing the tension sensor value to increase with time, and, subsequently, continuation of the contact state of the link member 21a1 with the intestinal wall has caused a further increase in the tension sensor value.

In consideration thereof, the present embodiment is arranged to perform computational processing to determine a weighting function capable of avoiding such a contact state based on the tension sensor value detected at that point even when a contact state of an arbitrary link member 21a with the intestinal wall continues. In other words, it is arranged so that, when determining angles of the plurality of link members 21a, a weighting function that weights the entirety of the plurality of link members 21a or, in other words, the entire manipulator 20 is created instead of a weighting function for each of the link members 21a as was used in the second embodiment.

More specifically, as shown in FIG. 47, temporal integration computing sections 61a1, 61a2, . . . , 61an respectively provided at each of the plurality of link members 21a are arranged to be connected to the weighting function switching computing section 62A in the dynamics computing section 43.

Tension sensor values F1, F2, . . . , Fn from the load detecting section 60 provided at the respective link members 21a are respectively supplied to each of the temporal integration computing sections 61a1, 61a2, . . . , 61an.

The temporal integration computing section 61a1 performs temporal integration computation processing for obtaining an evaluation function using the supplied tension sensor value F1, and an obtained evaluation function SF1 is outputted to the weighting function switching computing section 62A.

Temporal integration computation processing is performed in the same manner by the temporal integration computing sections 61a2, . . . , 61an to respectively determine evaluation functions SF2, . . . , SFn to be respectively outputted to the weighting function switching computing section 62A.

A formula based on computational processing performed by each of the temporal integration computing sections 61a1, 61a2, . . . , 61an is presented below.

$$\text{Evaluation function } S_{Fk} = \int_{t1}^{t2} F_k \, dt \quad \text{(Formula 30)}$$

The weighting function switching computing section 62 performs averaging according to the following formula (Formula 31) using the respectively supplied evaluation functions $S_{FK}$ to determine an evaluation function $S_{SUM}$, and further, using the evaluation function $S_{SUM}$, obtains a weighting function $\phi$ for the entire manipulator 20 by performing computational processing based on Formula 32. Formulas 31 and 32 are provided below.

$$\text{Evaluation function } S_{SUM} = \sum_{k=1}^{n} S_{FK} \quad \text{(Formula 31)}$$

$$\text{Weighting funtion } \phi_{Fi} = (1/S_{Fi})/S_{SUM} \quad \text{(Formula 32)}$$

The weighting function tables 62a used in the above second embodiment may be provided in the weighting switching computing section 62A, whereby a weighting function in at least one of the weighting function tables and a weighting function $\phi_{Fi}$ obtained by the computational processing may be switchably used as needed. As a result, a wide range of bending control can be performed depending on the insertion state of the insertion portion 9.

Therefore, according to the first variation, as described above, since a weighting function $\phi_{Fi}$ that enables a contact state with the intestinal wall or the like to be avoided is obtained with respect to the entire manipulator 20 and angles of the plurality of link members 21a are controlled, bending movement is performed on the entire manipulator 20 at angles enabling the entire manipulator 20 to avoid the intestinal wall even in the case where, upon insertion of the insertion portion 9 into a tube cavity, the bending portion 14 of the insertion portion 9 comes into contact with the intestinal wall or the like in the tube cavity and the contact state continues. As a result, insertion can be performed more safely and in a smooth manner.

While a configuration using a detection result of the load detecting section 60 has been described with respect to the first variation, the present embodiment is not limited to such a configuration. Instead, it is also possible to obtain a weighting function for the entire manipulator 20 regardless of the availability of the tension sensor that is the load detecting section 60. Such a second variation will be presented below.

FIGS. 48 and 49 are for describing a second variation of the second embodiment, wherein: FIG. 48 is a graph showing characteristics of a detection result from an actuator control block and time; and FIG. 49 is a block diagram showing a configuration of a substantial part including the weighting switching computing section in the dynamics computing section. The ordinate shown in FIG. 48 represents a displacement (P) of an angle by which each link member 21a moves obtained from a sensor; the abscissa represents time (t); and axes 1 and 2 respectively indicate first and second link members 21a.

As shown in FIG. 48, in the same manner as in the first variation, during insertion of the insertion portion 9 of the endoscope apparatus 1 into a tube cavity, for example, the displacement value (P) of the second link member 21a2 from the sensor 38 (refer to FIGS. 10 and 11) decreases as time advances, while the displacement value (P) of the first (distal end-side) link member 21a1 from the sensor 38 increases after reaching a given predetermined point in time.

In other words, this indicates that the first link member 21a1 came into contact with the intestinal wall of the large intestine or the like at the given predetermined point in time, thereby causing the displacement value to increase with time, and, subsequently, since the contact state of the link member 21a1 with the intestinal wall has continued, rotational movement of the distal end-side link member 21a1 has caused an further increase in the displacement value of the angle by which the link member 21a1 moves.

In consideration thereof, the present embodiment is arranged to perform computational processing to determine a weighting function capable of avoiding such a contact state based on the displacement value detected at that point even when a contact state of an arbitrary link member 21a with the intestinal wall continues. In other words, it is arranged so that, when determining angles of the plurality of link members 21a, a weighting function that weights the entirety of the plurality of link members 21a or, in other words, the entire manipulator 20 is created instead of a weighting function for each of the link members 21a as was used in the second embodiment.

More specifically, as shown in FIG. 49, temporal integration computing sections 61A1, 61A2, ..., 61An respectively provided at each of the plurality of link members 21a are arranged to be connected to the weighting function switching computing section 62B in the dynamics computing section 43.

Displacement values P1, P2, ..., Pn from the sensor 38 in the actuator control block 31 provided in the respective link members 21a are respectively supplied to each of the temporal integration computing sections 61A1, 61A2, ..., 61An.

The temporal integration computing section 61A1 performs temporal integration computation processing for obtaining an evaluation function using the supplied displacement value P1, and outputs an obtained evaluation function SP1 to the weighting function switching computing section 62B.

Temporal integration computation processing is performed in the same manner by the temporal integration computing sections 61A2, ..., 61An to respectively determine evaluation functions SP2, ..., SPn to be outputted to the weighting function switching computing section 62B.

A formula based on computational processing performed by each of the temporal integration computing sections 61A1, 61A2, ..., 61An is presented below.

$$\text{Evaluation function } S_{Pk} \int_{t1}^{t2} P_k \, dt \quad \text{(Formula 33)}$$

The weighting function switching computing section 62B performs averaging according to Formula 34 below using the respectively supplied evaluation functions $S_{PK}$ to determine an evaluation function $S_{SUM}$, and further, using the evaluation function $S_{SUM}$, obtains a weighting function $\phi_i$ for the entire manipulator 20 by performing computational processing based on Formula 35. Formulas 34 and 35 are provided below.

$$\text{Evaluation function } S_{SUM} = \sum_{k=1}^{n} S_{PK} \quad \text{(Formula 34)}$$

$$\text{Weighting function } \phi_{Pi} = (1/S_{Pi})/S_{SUM} \quad \text{(Formula 35)}$$

The weighting function tables 62a used in the above second embodiment may be provided in the weighting function switching computing sections 62A and 62B, whereby a weighting function in at least one of the weighting function tables and a weighting function $\phi_i$ obtained by the above-mentioned computational processing may be switchably used as needed. As a result, a wide range of bending control can be performed depending on the insertion state of the insertion portion 9.

Therefore, as described above, it is now possible to obtain a weighting function $\phi_i$ with respect to the entire manipulator 20 that enables a contact state with the intestinal wall or the like to be avoided without a tension sensor that is the load detecting section 60 provided. By controlling the angles of the plurality of link members 21a using the weighting function $\phi_i$, since bending movements are performed by the entire manipulator 20 in the same manner as in the first variation at angles enabling the entire manipulator 20 to avoid the intestinal wall even in the case where, upon insertion of the insertion portion 9 into a tube cavity, the bending portion 14 of the insertion portion 9 comes into contact with the intestinal wall or the like in the tube cavity and the contact state continues, insertion can be performed more safely and in a smoother manner.

As described above, according to the present second embodiment, since the distal end-side link member 21a1 among the plurality of link members 21a constituting the bending portion 14 of the insertion portion 9 can be point-locked, and attitude control can be performed over the other link members 21a so that arbitrary attitudes having redundancy can be assumed, it is now possible to insert the bending portion 14 of the insertion portion 9 in a shape conforming to the interior shape of a tube cavity. As a result, advantageous effects such as improvement of insertability of the insertion portion can be achieved.

In addition, the endoscope apparatus 1 according to the present second embodiment enables automatic determination of an optimum weighting function based on a detection result of a load detecting section 60 in the case where, when inserting the bending portion 14 into a tube cavity, computational processing is performed using a weighting function on angles of a plurality of link members 21a constituting the bending portion 14 or on an angle of an arbitrary link member 21a among the plurality of link members 21a. Consequently, since forced attitudes of the plurality of link members 21a or the manipulator 20 can be eliminated and an angle necessary for enabling movement in a mobile range can be acquired for each of the plurality of link members 21a, it is now possible to perform insertion into a tube cavity in a smooth manner.

For the present embodiment, while point-locking a two-dimensional position and direction of the distal end-side link member 21a1 among the plurality of link members 21a has been described, the present invention is not limited to this example. Instead, the present invention may be configured so that a three-dimensional position and direction are point-locked.

For the present embodiment, while the bending portion 14 having the insertion portion driving mechanism 20 constituting a manipulator has been described as being provided at the insertion portion 9 of the endoscope 2, the bending portion 14 may be arranged to be provided at an insertion portion of an endoscope insertion aiding device that aids the insertion of the insertion portion 9 into a tube cavity by allowing insertion of the insertion portion 9 of the endoscope 2.

Next, a third embodiment of the present invention will be described with reference to FIGS. 50 to 57. The present third embodiment primarily differs from the above first embodiment in that bending movement of the bending portion 14 is performed by respectively rotationally moving the plurality of link members 21a by respectively pulling or relaxing a plurality of bending operation wires 130A (130A1, 130A2, ..., 130An). Otherwise, descriptions on points similar to the first embodiment described above will be omitted.

Figure 50:
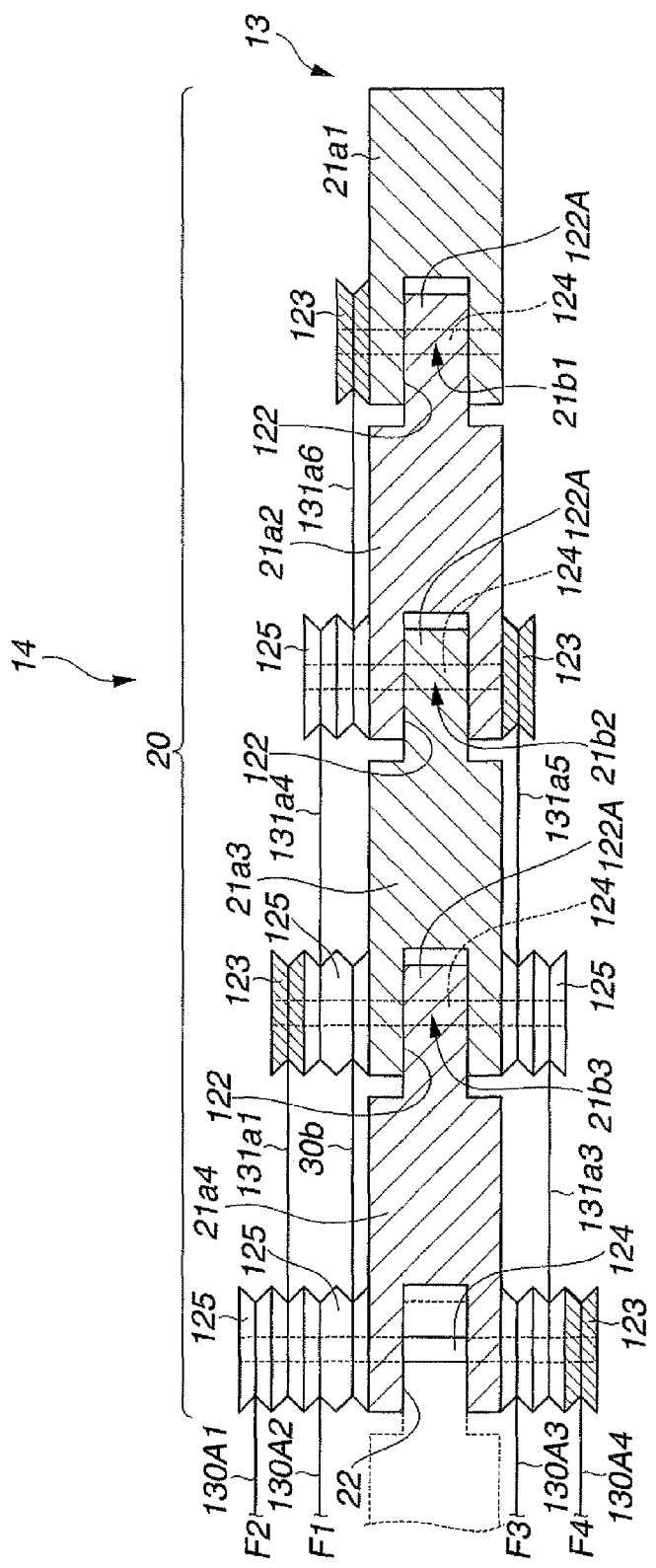
FIG. 50 relates to a third embodiment of the present invention and is a top view showing a configuration of a bending portion whose driving mechanism is constituted by a bending operation wire, a driving pulley and a free pulley.
Figure 51:
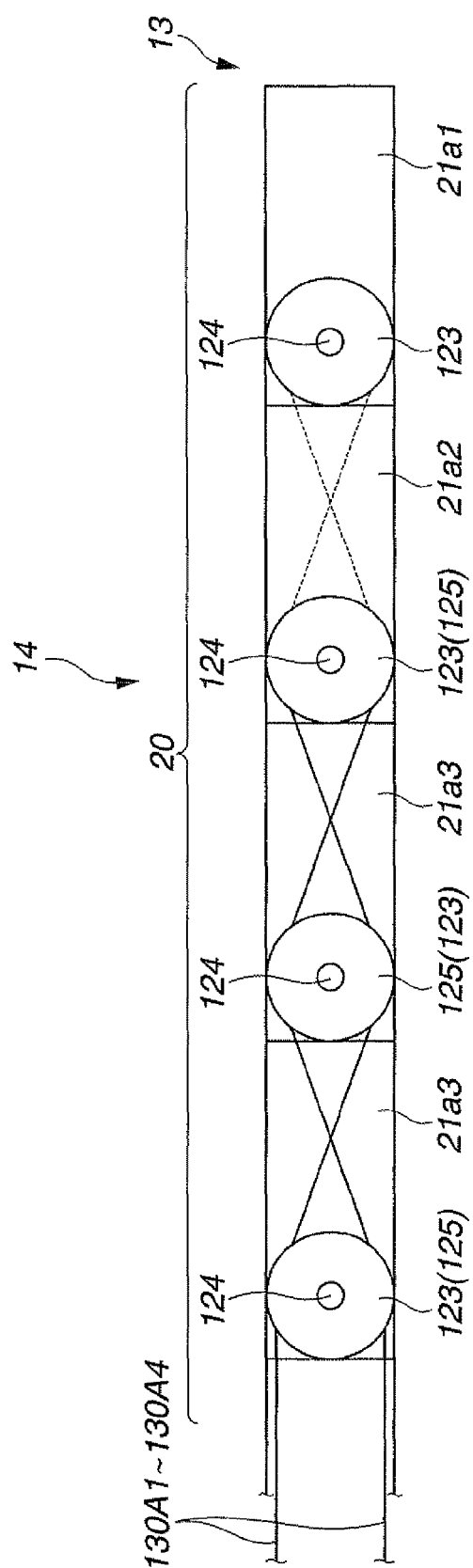
FIG. 51 relates to the third embodiment of the present invention and is a side view showing a suspended state of a bending operation wire provided between respective link members of the bending portion shown in FIG. 50.
Figure 52:
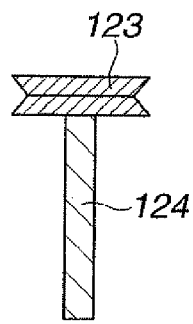
FIG. 52 relates to the third embodiment of the present invention and is a configuration diagram showing a configuration of a driving pulley provided with the driving shaft shown in FIG. 50.
Figure 53:
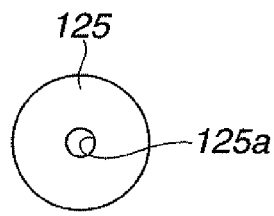
FIG. 53 relates to the third embodiment of the present invention and is a top view showing a configuration of the free pulley shown in FIG. 50.

FIG. 50 is a top view showing a configuration of a bending portion whose driving mechanism is constituted by a bending operation wire, a driving pulley and a free pulley; FIG. 51 is a side view showing a suspended state of a bending operation wire provided between respective link members of the bending portion shown in FIG. 50; FIG. 52 is a configuration diagram showing a configuration of a driving pulley provided with the driving shaft shown in FIG. 50; and FIG. 53 is a top view showing a configuration of the free pulley shown in FIG. 50.

The present third embodiment is arranged so that the driving section 10b is disposed inside the operation section 10, and a plurality of motors 27 of the driving section 10b is connected through the inside of the insertion portion 9 to the respective bending operation wires 130A.

The driving section 10b (respective motors 27) respectively rotationally moves the plurality of link members 21a1, 21a2, ..., 21an by pulling or relaxing the plurality of bending operation wires 130A1, 130A2, ..., 130An.

The bending operation wires 130A1 to 130An are arranged to be connected to driving shafts of the motors 27 via gears and sprockets, not shown. The bending operation wires 130A1 to 130An are extended in the insertion portion 9, and proximal end portions thereof are suspended by a driving pulley 123 and a free pulley 125 of a rearmost end-side link member 21an among the plurality of link members 21a1, 21a2, ..., 21an. As will be described later, the respective intervals between the link member 21an and the other link members 21a1, ..., 21a(n−1) are arranged to be suspended by other bending operation wires 131a1, 131a2, ..., 131am (where m is a natural number).

Consequently, the rotational forces of the respective motors 27 are arranged to be transmitted to the plurality of link members 21a via the bending operation wires 130A1 to 130An, the driving pulley 123, the free pulley 125 and the bending operation wires 131a1 to 131am.

The numbers of the link members 21a and the joint members 21b are not limited to the configuration examples shown in the drawings, and configurations are also possible wherein the numbers thereof are increased or decreased in accordance with the intended use of the endoscope 2. The link member 21a1 is disposed on a most distal end-side of the distal end portion 13, and is arranged so that link members 21a2, 21a3, ..., 21an are sequentially connected to a rear end-side thereof. As a result, the joint members 21b1, 21b2, 21b3, ..., 21bn are also respectively disposed between the link members 21a in sequence from the distal end portion 13 side.

A specific configuration of the bending portion 14 is shown in FIG. 50. The example shown in FIG. 50 is a case where n=4, and where the insertion portion driving mechanism 20 is constituted using four link members 21a1 to 21a4.

As shown in FIG. 50, by pulling or relaxing the bending operation wires 130A1 to 130A4 and 131a1 to 131a6, the plurality of link members 21a1, 21a2, 21a3 and 21a4 are respectively consecutively connected so as to be rotationally movable by the insertion portion driving mechanism 20 of the bending portion 14.

The plurality of link members 21a1 to 21a4 are respectively connected so as to be rotationally movable by a driving shaft 124 that is the joint members 21b1 to 21b4. The driving shaft 124 is a shaft member integrally configured with the driving pulley 123, to be described later. A potentiometer, not shown, is mounted as first detecting section on the driving shaft 124.

The potentiometer is arranged to detect a rotational quantity of the driving shaft 124 and output the same as a state quantity detection signal of the link member 21a to the controller 5 via a signal wire, not shown. The potentiometer as first detecting section may be configured so as to be provided on, for example, a sprocket (not shown) for transmitting the rotational force of a motor 27 provided on the driving section 10b side to a bending operation wire.

Connecting grooves 122 for pivotally supporting so as to be rotationally movable and housing a connecting protruding portion 122A formed on a link member 21a of a subsequent stage are respectively provided on the plurality of link members 21a1 to 21a4. The driving shaft 124 is fitted and fixed into a hole provided on the connecting protruding portion 122A in a state where the connecting protruding portion 122A is mounted on the connecting groove 122 of the subsequent-stage link member 21a to enable the link member 21a to be connected so as to be rotationally movable.

A driving shaft 124 that pivotally supports the connecting groove 124 and the connecting protruding portion 122A of the second link member 21a2 is fitted and fixed to the proximal end-side of the most distal end-side link member 21a1. A driving pulley 123 is integrally formed on the proximal end portion on one side of the driving shaft 124. The driving pulley 123 is arranged to be fixed to a lateral face of the distal end-side link member 21a1.

As shown in FIG. 52, the driving pulley 123 having the driving shaft 124 is arranged to create rotational force when the bending operation wire 131a6 is suspended and, at the same time, either pulled or relaxed, and the driving shaft 124 is integrally provided to the lower side of the center of the driving pulley 123.

The length of the driving shaft 124 of the driving pulley 123 is formed to be elongated in consideration of a required thickness when stacking the free pulleys 125, to be described later, in sequence from the distal end-side link member 21a1, the second-stage link member 21a2, the third-stage link member 21a3, and the fourth-stage link member 21a4.

The bending operation wire 131a6 is suspended by a driving pulley 123 fixed to the distal end-side link member 21a1. The other side of the bending operation wire 131a6 is suspended by a free pulley 125 disposed on the same side of the second-stage link member 21a2 and which is pivotally supported so as to be rotationally movable by the driving shaft 124.

As for the free pulley 125, two pulleys are annexed as shown in FIGS. 50 and 53, and is configured with a hole 125a into which the driving shaft 124 is inserted. The free pulley 125 is pivotally supported so as to be rotationally movable by the driving shaft 124 of the driving pulley 123 fixed to the other side of the second-stage link member 21a2. The two pulleys of the free pulley 125 respectively support the bending operation wires 131a6 and 131a4 from both the driving pulley 123 of the distal end-side link member 21a1 and the free pulley 125 provided at the third-stage link member 21a3.

A driving pulley 123 is fixed to the opposite side of the free pulley 125 of the second-stage link member 21a2. The bending operation wire 131a5 is suspended by the driving pulley 123. The other side of the bending operation wire 131a5 is suspended by a free pulley 125 disposed on the same side of the third-stage link member 21a3 and which is pivotally supported so as to be rotationally movable by the driving shaft 124.

The bending operation wire 131a3 is suspended by the other pulley of the free pulley 125. The other side of the bending operation wire 131a3 is suspended by a free pulley 125 disposed on the same side of the fourth-stage link member 21a4 and which is pivotally supported so as to be rotationally movable by the driving shaft 124.

A driving pulley 123 is fixed via the free pulley 125 to the opposite side of the free pulley 125 of the third-stage link member 21a3. The bending operation wire 131a1 is suspended by the driving pulley 123. The other side of the bending operation wire 131a1 is suspended by a free pulley 125 disposed on the same side of the fourth-stage link member 21a4 and which is pivotally supported so as to be rotationally movable by the driving shaft 124. The bending operation wire 131a2 is suspended by the other pulley of the free pulley pivotally supported so as to be rotationally movable by the driving pulley 123. The other side of the bending operation wire 131a2 is suspended by a free pulley 125 disposed on the same side of the fourth-stage link member 21a4 and which is pivotally supported so as to be rotationally movable by the driving shaft 124.

Two free pulleys 125 respectively suspending the bending operation wires 131a1 and 131a4 to one of the pulleys are pivotally supported by the driving shaft 124 on one side of the fourth-stage link member 21a4. Bending operation wires 130A1 and 130A2 extended via the inside of the insertion portion 9 are arranged to be suspended by the two free pulleys 125.

A free pulley 125 suspending the bending operation wire 130A3 to one of the pulleys is pivotally supported by the driving shaft 124 on the opposite side of the fourth-stage link member 21a4. A driving pulley 123 integrally configured with the driving shaft 125 is disposed on the outer side of the free pulley 125. The driving pulley 123 is fixed to the fourth-stage link member 21a4 via the free pulley 125. A bending operation wire 130A3 extended via the inside of the insertion portion 9 is arranged to be suspended by the free pulley 125. A bending operation wire 130A4 extended in the same manner via the inside of the insertion portion 9 is arranged to be suspended by the driving pulley 123.

As shown in FIG. 51, the bending operation wires 131a1 to 131a6 are arranged to be suspended in respective crossed states by the driving pulley 123 or the free pulley 125 between each corresponding link member 21a.

To describe bending movements of the bending portion 14 attributable to the pulling of the bending operation wires 130A1 to 130A4, for example, when the bending operation wire 130A4 shown in FIG. 50 is pulled by a rotational force F4, since the driving pulley 123 supporting the bending operation wire 130A4 is fixed to the fourth-stage link member 21a4, the fourth-stage link member 21a4 is to be rotationally moved.

When an opposite-side bending operation wire 130A1 is pulled by a rotational force F2 in a state where the bending operation wire 130A4 is immobilized, the rotation of the free pulley 125 that is suspended by the bending operation wire 130A1 causes the bending operation wire 131a1 suspended by the free pulley 125 to be pulled. The rotational force is transmitted to the driving pulley 123 of the third-stage link member 21a3 by which the bending operation wire 131a1 is suspended to cause rotational movement of the third-stage link member 21a4.

When the bending operation wire 130A3 is pulled by a rotational force F3 in a state where the bending operation wires 130A4 and 130A1 are immobilized, the rotation of the free pulley 125 that is suspended by the bending operation wire 130A3 causes the bending operation wire 131a3 suspended by the free pulley 125 to be pulled. The rotational force is transmitted to the free pulley 125 of the third-stage link member 21a3 by which the bending operation wire 131a3 is suspended. Rotation of the free pulley 125 causes the bending operation wire 131a5 that is suspended by the free pulley 125 to be pulled. The rotational force is transmitted to the driving pulley 123 of the second-stage link member 21a2 by which the bending operation wire 131a5 is suspended to cause rotational movement of the second-stage link member 21a2.

Further, when the bending operation wire 130A2 is pulled by a rotational force F1 in a state where the bending operation wires 130A4, 130A1 and 130A3 are immobilized, the rotation of the free pulley 125 that is suspended by the bending operation wire 130A2 causes the bending operation wire 131a2 suspended by the free pulley 125 to be pulled. In the same manner as described above, the rotational force is transmitted to the driving pulley 123 of the distal end-side link member 21a1 via the free pulley 125 of the third-stage link member 21a3 by which the bending operation wire 131a2 is suspended, the bending operation wire 131a4, the free pulley 125 of the second-stage link member 21a2, and the bending operation wire 131a6. Consequently, the rotation of the driving pulley 123 cases rotational movement of the distal end-side link member 21a4.

As seen, by performing appropriate rotational control of the rotational forces F1 to F4 of the respective motors 27 in the driving section 10b so as to pull or relax the bending operation wires 130A1 to 130A4, it is possible to rotationally move a plurality of link members or only a designated link member 21a.

Since an endoscope apparatus having a multi-joint link structure is arranged to bend the bending portion 14 by controlling pulling or relaxing of bending operation wires, there may be cases where bending movement is affected by interference from a bending operation wire between link members 21a. Such a problem will be described with reference to FIGS. 50, 54 and 55.

Figure 54:
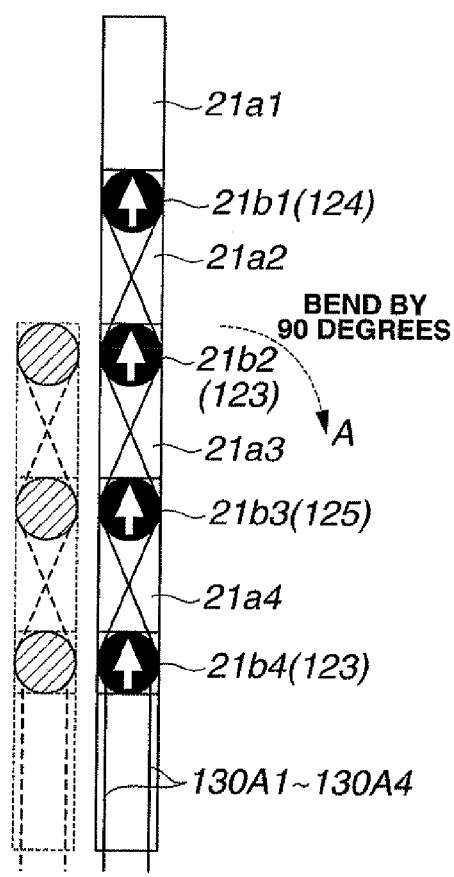
FIG. 54 relates to the third embodiment of the present invention and is an explanatory diagram for explaining problem areas of a case where bending movements of a link member is performed by pulling or relaxing the bending operation wire, and shows a state when a plurality of link members is not performing bending movements.
Figure 55:
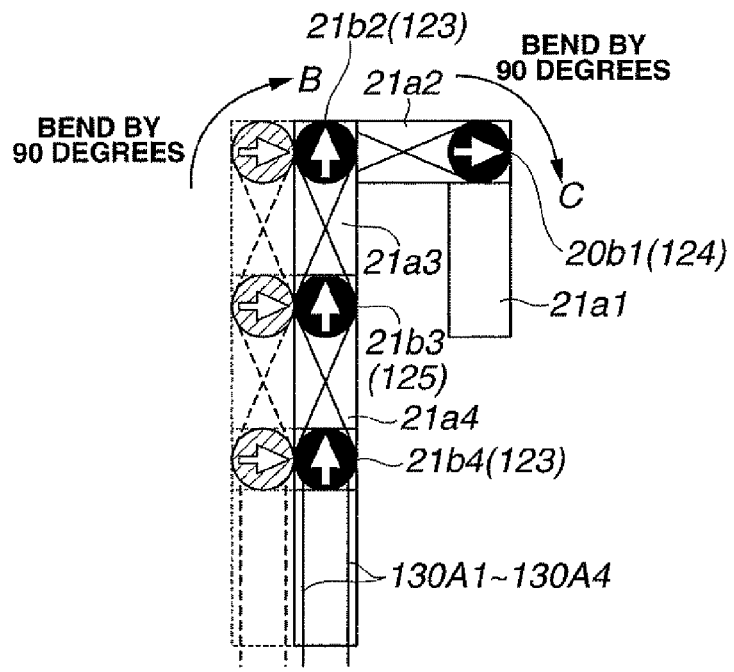
FIG. 55 relates to the third embodiment of the present invention and is a diagram showing a state in which the distal end-side link member inadvertently bends due to interference when a second-stage link member is bent by 90 degrees.
Figure 56:
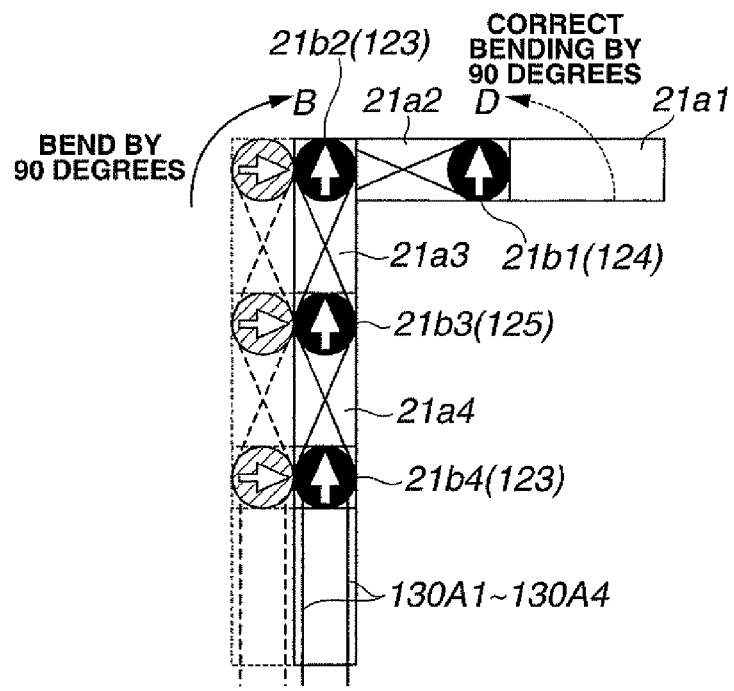
FIG. 56 relates to the third embodiment of the present invention and is a graph showing characteristics of a detection result from the load detecting section and a coefficient that determines a weighting function.
Figure 57:
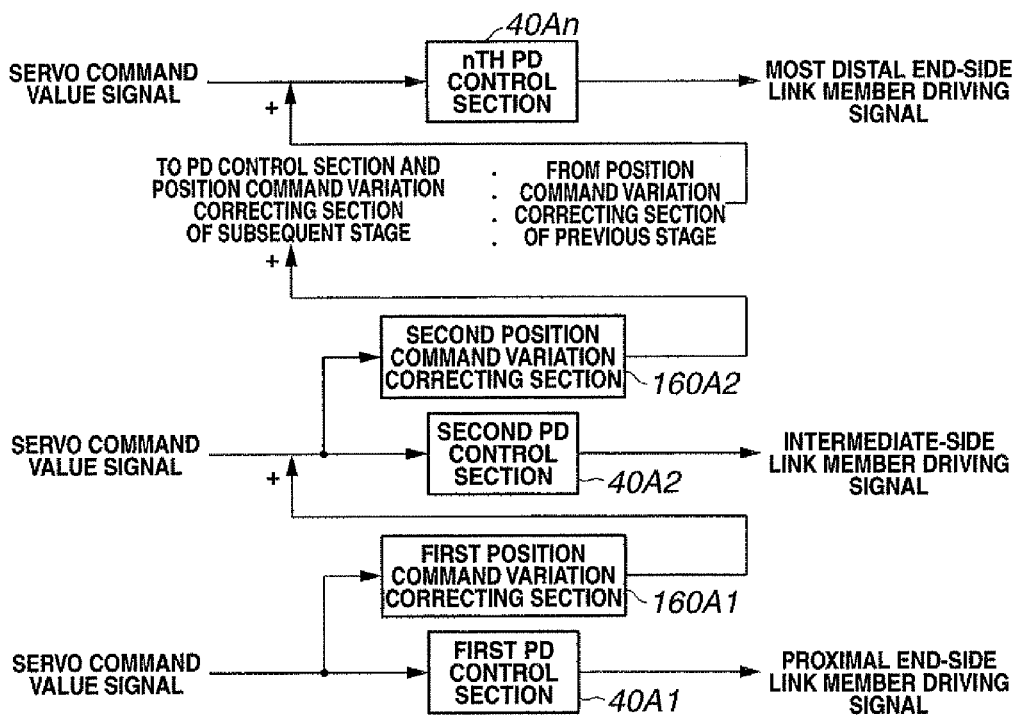
FIG. 57 relates to the third embodiment of the present invention and is a diagram showing a state in which a controller according to the present embodiment performs correction control so as to bend the distal end-side link member by 90 degrees in an opposite direction from the state shown in FIG. 55.

FIGS. 54 to 56 are explanatory diagrams for explaining problem areas of a case where bending movements of a multi-link member 21a is performed by pulling or relaxing bending operation wires, wherein: FIG. 54 shows a state when a plurality of link members is not performing bending movements; FIG. 55 shows a state in which the distal end-side link member inadvertently bends due to interference when a second-stage link member is bent by 90 degrees; and FIG. 56 shows a state in which correction processing by 90 degrees in the opposite direction is performed by the controller according to the present invention from the state shown in FIG. 55. FIG. 57 is a block line diagram showing a configuration of a servo controller in each actuator control block according to the present embodiment.

The arrows indicating the positions of the driving pulley 123 and the free pulley 125 in FIGS. 54 and 55 are for explanatory purposes and indicate a direction of rotational movement of each link member. The shaded area on the left hand side of the diagrams indicate opposite side portions of each link member of the bending portion 14.

For example, as shown in FIG. 54, let us assume that, from a state where the bending portion 14 of the insertion portion 9 is not bent and each of the link members 21a1 to 21a4 is also not bent, the operator performs bending operation of the second-stage link member 21a2 so as to bend the same 90 degrees in the direction of arrow A as shown in the diagram.

In this case, as shown in FIG. 50, by pulling the bending operation wire 130A3 by the rotational force F3 in a state where the bending operation wires 130A4 and 130A1 are immobilized, rotational force is transmitted to the driving pulley 123 fixed to the second-stage link member 21a2 via the bending operation wires 130A3, 131a3, the free pulley 125 and the bending operation wire 131a5, and, for example, the second-stage link member 21a2 bends 90 degrees in the direction of arrow A as shown in the diagram.

However, at this point, since the bending operation wires 130A1, 130A2, 131a1, 131a2, 131a4 and 131a6 (refer to FIG. 50) are respectively in immobilized states, the bending movement of the second-stage link member 21a1 creates a force at the driving pulley 123 and the free pulley 125 respectively suspending the bending operation wires 130A1, 130A2, 131a1, 131a2, 131a4 and 131a6 which attempts to bend the driving pulley 123 and the free pulley 125 in the direction of the arrows shown in the shaded area on the left hand side of the diagram.

As shown in FIG. 50, since the distal end-side link member 21a1 is connected to the free pulley 125 of the second-stage link member 21a2 via the bending operation wire 131a6 suspended by the driving pulley 123, the force created at the free pulley 125 by the bending movement of the second-stage link member 21a2 interferes with the bending operation wire 131a6. As a result, as shown in FIG. 55, the distal end-side link member 21a1 will be inadvertently bent in the direction of the arrow C shown in the diagram with respect to the second-stage link member 21a2.

However, in the case where the distal end-side link member 21a1 is bent as a result of a bending movement of an intermediate link member 21a as described above, as shown in FIG. 56, the endoscope apparatus 1 according to the present embodiment is capable of performing correction control so as to cause a bending movement of the distal end-side link member 21a1 in the opposite direction (the direction of an arrow D shown in the diagram) by an angle corresponding to the bent angle (90 degrees). A schematic internal configuration of an actuator control block capable of such bending correction control is shown in FIG. 57.

As described with reference to FIGS. 9 to 12 for the above first embodiment, the endoscope apparatus 1 according to the present third embodiment includes actuator control blocks 31a1 to 31an corresponding to the respective link members 21a. A servo controller 36A is respectively provided at the actuator control blocks 31a1 to 31an.

As described with reference to FIG. 12 for the above first embodiment, the servo controller 36A includes a PD control section 40. As shown in FIG. 57, the present embodiment is further provided with a position command variation correcting section 160 that acquires a servo command value signal (including displacement information from the motor 27) supplied to the PD control section 40, calculates an opposite-direction position command variation correction quantity from the servo command value signal, and adds the opposite-direction position command variation correction quantity with the servo command value signal and supplies the sum to a PD control section 40 of a subsequent stage.

In FIG. 57, PD control sections 40 of the respective stages are indicated by reference characters 40A1 to 40An assigned thereto, and position command variation correcting sections 160 of the respective stages are indicated by reference characters 160A1 to 160An assigned thereto. More specifically, in the present embodiment, as shown in FIG. 57, assuming that the PD control section 40 corresponding to the distal end-side link member 21a1 (nearest end-side link member) is first PD control section 40A1, the PD control section 40 corresponding to the subsequent-stage (second-stage) link member 21a2 (intermediate-side link member) is second PD control section 40A2, . . . , and the PD control section 40 corresponding to the furthest end-side link member 21an is Nth PD control section 40AN, position command variation correcting sections 160A1, 160A2, . . . , 160A(N−1) are respectively provided between the respective PD control sections 40A1, 40A2, . . . , 40AN.

For example, the first position command variation correcting section 160A1 calculates a position command variation that is opposite in direction to the distal end-side link member 21a1 from the supplied servo command value signal and the displacement information of the motor 27, and outputs the same to the input side of the subsequent-stage second PD control section 40A2.

Then, a servo command value signal to which is added the position command variation from the first position command variation correcting section 160A1 is supplied to the second PD control section 40A2, which in turn creates an operation output value signal (that is a driving signal, and which is indicated in the diagram as an intermediate-side link member driving signal) through PD control such as proportional/differential control based on the servo command value signal, and provides the same to a corresponding motor 27.

The second position command variation correcting section 160A2 calculates a position command variation that is opposite in direction to the second-stage link member 21a2 from the servo command value signal supplied to the second PD control section 40A2, and outputs the same to the input side of, for example, the third PD control section 40A3 of the subsequent stage.

Then, a servo command value signal to which is added the position command variation from the second position command variation correcting section 160A2 is supplied to the third PD control section 40A3, which in turn creates an operation output value signal (that is a driving signal, and which is indicated in the diagram as a farthest end-side link member driving signal) through PD control such as proportional/differential control based on the servo command value signal, and provides the same to a corresponding motor 27.

As shown, in the present embodiment, a position command variation that is opposite in direction to the link member 21a is sequentially added to the servo command value signal of the subsequent-stage link member from the nearest end-side link member via intermediate-side link members towards the furthest end-side link member, whereby rotational control of the motor 27 is performed based on obtained driving signals.

In other words, in the case where the distal end-side link member 12a1 is inadvertently bent by 90 degrees as a result of a bending movement of an intermediate link member 21a as shown in FIG. 55, the servo controller 36A according to the present embodiment performs correction control so as to cause bending movement of the subsequent-stage link member 21a2 in the opposite direction by an angle (90 degrees) corresponding to the angle by which the distal end-side link member 21a1 was bent. Then, in the same manner, the servo controller 36A performs correction control so as to cause bending movement of the subsequent-stage link member 21a3 and thereafter in the opposite direction by an angle corresponding to the angle by which the previous-stage link member 21a was bent.

Consequently, during bending operation of an arbitrary link member 21a, even when a distal end-side link member 21a is bent due to interference of a bending operation wire between the respective link members 21a, correction can be performed so as to reliably return the distal end-side link member 21a1 to its original position. Therefore, it is now possible to maintain a position of the distal end portion 13 based on an operation signal.

The controller 5 is capable of further enhancing the insertability of the insertion portion 9 by performing stiffness control so as to vary the stiffness of the entire insertion portion 9 including the bending portion 14. Such a fourth embodiment is shown in FIGS. 58 to 60.

Figure 58:
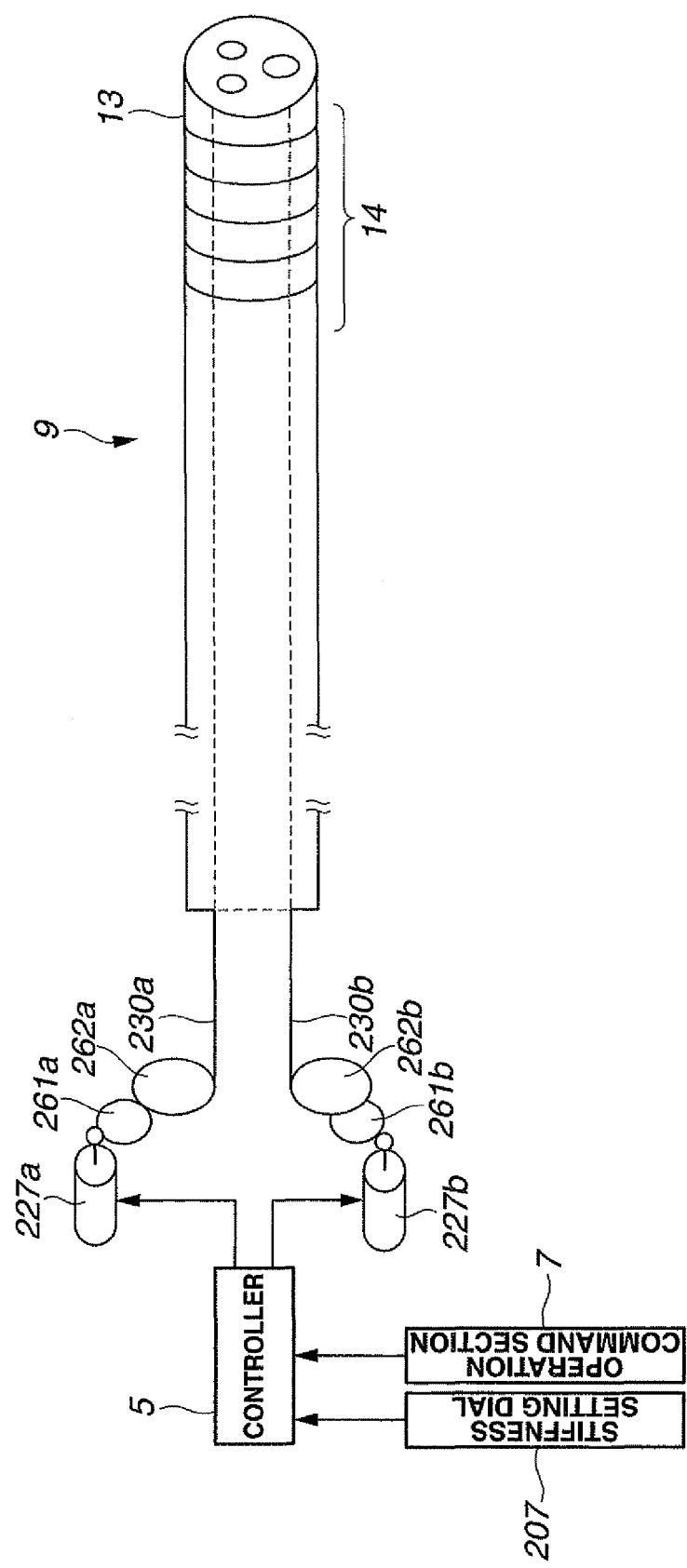
FIG. 58 relates to a fourth embodiment of the present invention and is a configuration diagram showing a configuration of an entire endoscope apparatus.
Figure 59:
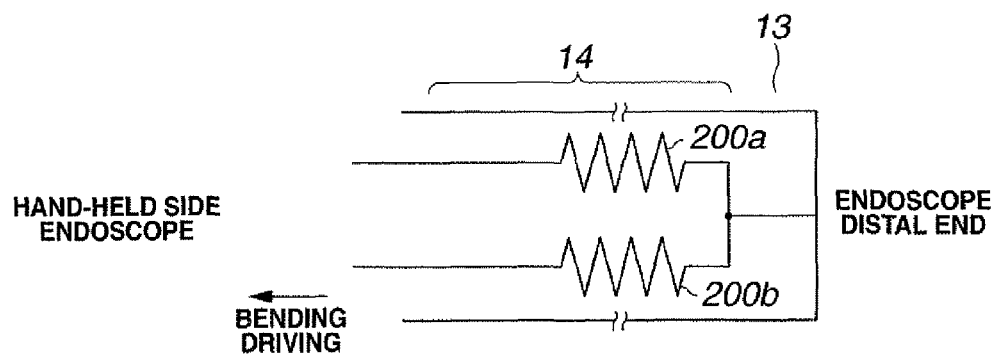
FIG. 59 relates to the fourth embodiment of the present invention and is an explanatory diagram explaining characteristics of a bending portion when bending driving is performed thereon by a controller.
Figure 60:
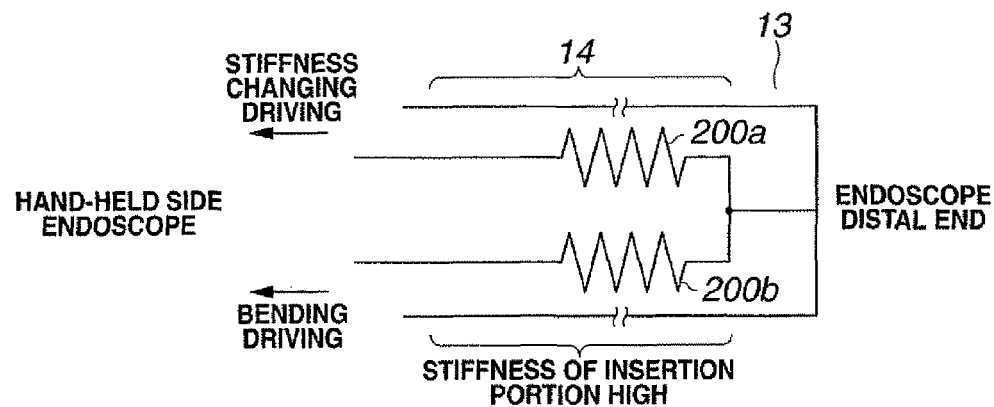
FIG. 60 is an explanatory diagram explaining characteristics of a bending portion when stiffness control is performed thereon by a controller according to the fourth embodiment.

FIGS. 58 to 60 are related to the fourth embodiment, wherein: FIG. 58 is a configuration diagram showing a configuration of an entire endoscope apparatus according to the fourth embodiment; FIG. 59 is an explanatory diagram explaining characteristics of a bending portion when bending driving is performed thereon by a controller; and FIG. 60 is an explanatory diagram explaining characteristics of a bending portion when stiffness control is performed thereon by a controller according to the second embodiment. For the present fourth embodiment, a description will be given on the assumption that an endoscope 2 is provided which is capable of bending the bending portion 14 in two directions, namely, upward and downward.

As shown in FIG. 58, an endoscope apparatus 1 includes a controller 5 similar to that of the third embodiment, an operation command section 7, a stiffness setting dial 207, and the endoscope 2.

The endoscope 2 includes: two motors 227a and 227b that are the driving section 10b; two gears 261a and 261b for transmitting the rotational force of each of the motors 227a and 227b; sprockets 262a and 262b that meshes with the two gears 261a and 261b and rotates so as to respectively pull or relax bending operation wires 230a and 230b; a bending portion 14 in which the bending operation wires 230a and 230b are extended in an insertion portion 9 and which is bendable in two directions, namely, upward and downward, by the pulling or relaxing of the bending operation wires 230a and 230b; and a distal end portion 13.

Although not shown, potentiometers that detect a rotational quantity of each motor 227a, 227b are provided at the sprockets 262a and 262b. Detection results from the potentiometers are arranged to be fed back to the controller 5.

The stiffness setting dial 207 is operation section for setting a stiffness level of the bending portion 14 or the entire insertion portion 9 including the bending portion 14, and outputs a stiffness setting level signal based on an operation of the operator to the controller 5.

While the configuration of the controller 5 is approximately the same as that of the third embodiment, when the stiffness setting dial 207 is operated during bending control of the bending portion 14 based on an operation command value signal by the operation command section 7, stiffness of the bending portion 14 or the entire insertion portion 9 including the bending portion 14 performing a bending movement is controlled based on the stiffness setting level signal.

Stiffness control of the bending portion 14 or the entire insertion portion 9 will now be described with reference to FIGS. 59 and 60.

FIG. 59 shows a state where downward bending driving is performed on the bending portion 14 by the controller 5 as a dynamic simplified model. In FIG. 59, for simplicity, the states of the bending operation wires (pulling wires) 230a and 230b are handled as spring models in which respective end points thereof are fixed to the distal end portion of the endoscope. In other words, as shown in FIG. 59, load quantities applied to the bending operation wires 230a and 230b are simulated by the springs 200a and 200b. In the diagram, when only the motor 227b is being driven, a force pulling the spring 200b on the bending operation wire 230b side exceeds a force pulling the spring 200a on the bending operation wire 230a side. As a result, the bending portion 14 bends downward.

In the present embodiment, after causing movement of the bending portion 14 into a predetermined bent shape, for example, as shown in FIG. 60, by rotationally controlling the opposite-side motor 227a in the same manner as the motor 227b, the motor 227a is rotationally controlled so that the force pulling the spring 200a of the bending operation wire 230a side becomes equal to the force pulling the spring 200b on the bending operation wire 230b side.

Consequently, since both pulling wires 230a and 230b have end points fixed to the distal end portion of the endoscope according to the present embodiment, a compression force will be applied to the entire insertion portion of the endoscope as a result of the force pulling the spring 200a of the bending operation wire 230a side and the force pulling the spring 200b on the bending operation wire 230b side. At this point, even when the force is applied to both parts, the force will be applied while maintaining positions of the wires by adopting position control as the method of wire pulling control.

It should be noted that, since the springs depicted in FIGS. 59 and 60 are dynamic model expressions of pulling wires, characteristics will reflect those of the wires themselves.

Therefore, the bending portion 14 assumes a stiffness state in which the bending shape thereof is retained. In addition, since the bending operation wires 230a and 230b are disposed inside the insertion portion 9, the entire insertion portion 9 will also attain stiffness.

The stiffness setting dial 207 is arranged so that levels of forces respectively pulling the springs 200a and 200b on the sides of the bending operation wires 230a and 230b are switchable and settable in phases. Therefore, during bending driving, the controller 5 is able to perform control so that the stiffness level of the bending portion 14 or the entire insertion portion 9 including the bending portion 14 is appropriately varied.

Consequently, according to the fourth embodiment, since the stiffness of the bending portion 14 or the entire insertion portion 9 including the bending portion 14 can be controlled, insertability of the insertion portion 9 can be improved by performing stiffness control of the bending portion 14 or the entire insertion portion 9 during insertion.

Figure 61:
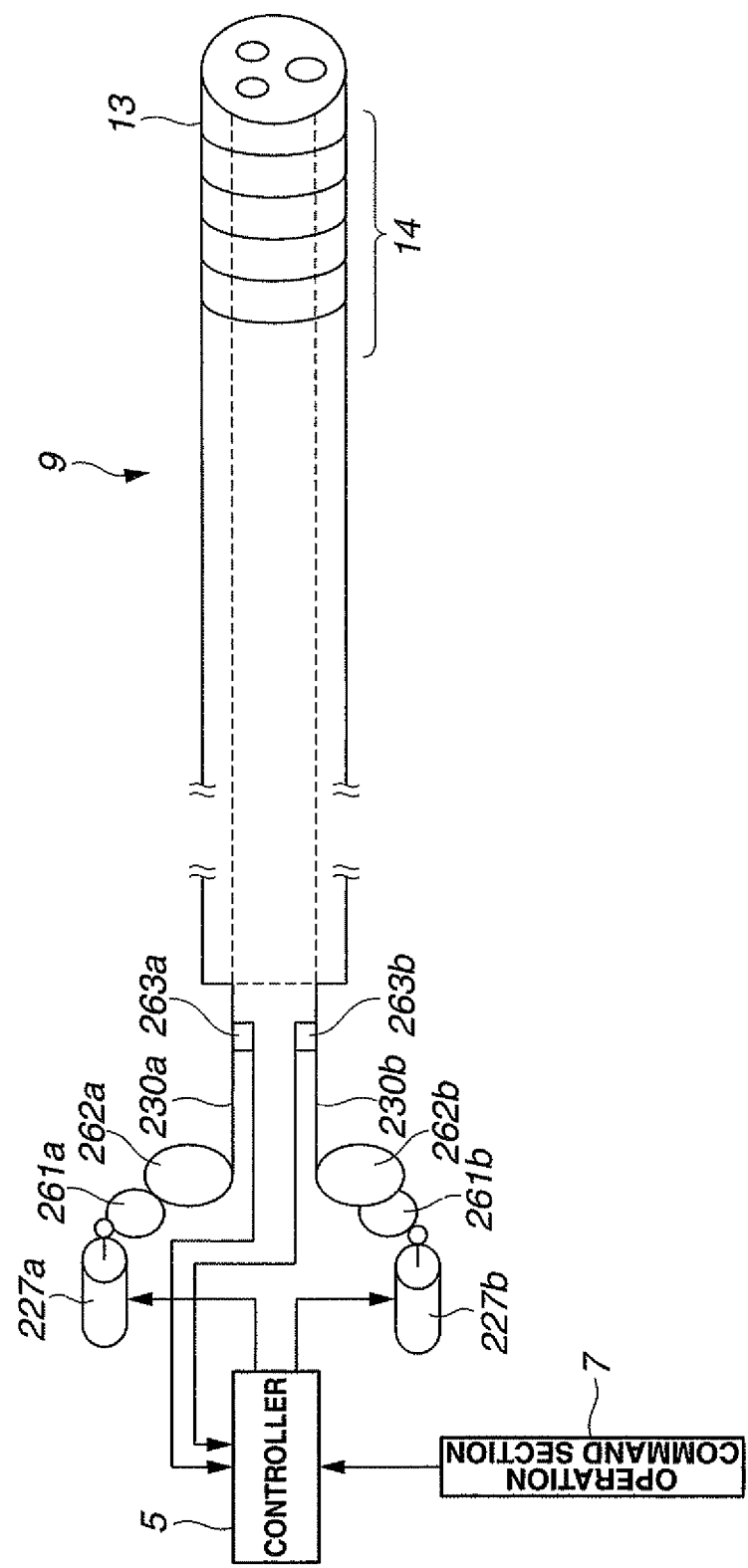
FIG. 61 relates to a first variation of the fourth embodiment and is a configuration diagram showing a configuration of an entire endoscope apparatus.
Figure 62:
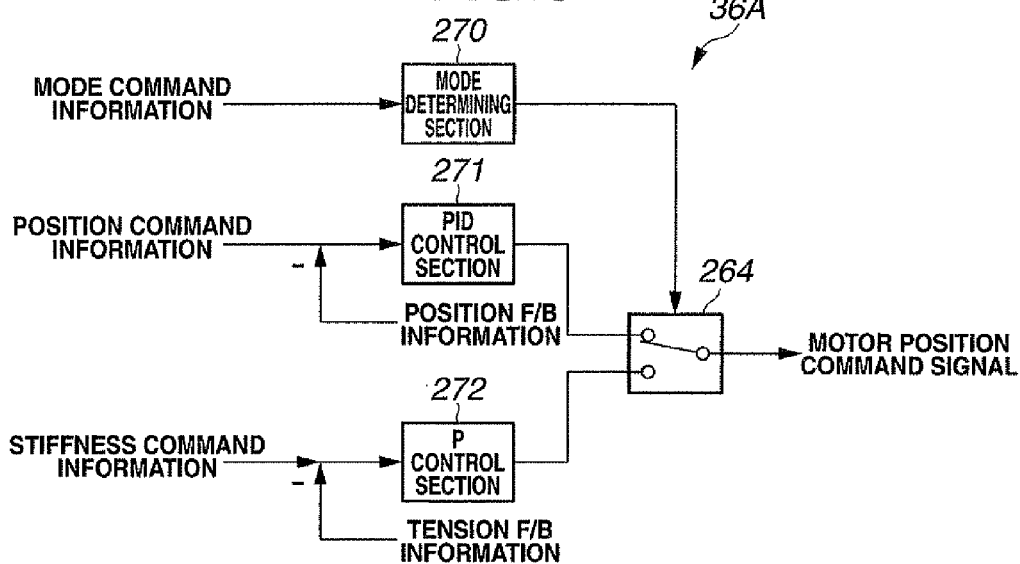
FIG. 62 relates to the first variation of the fourth embodiment and is a block diagram showing a specific internal configuration of a servo controller.
Figure 63:
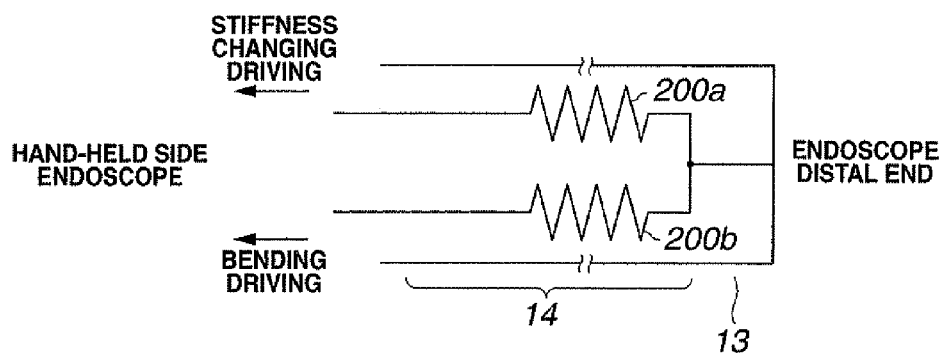
FIG. 63 relates to the first variation of the fourth embodiment and is an explanatory diagram explaining characteristics of a bending portion when stiffness control is performed thereon by a controller.
Figure 64:
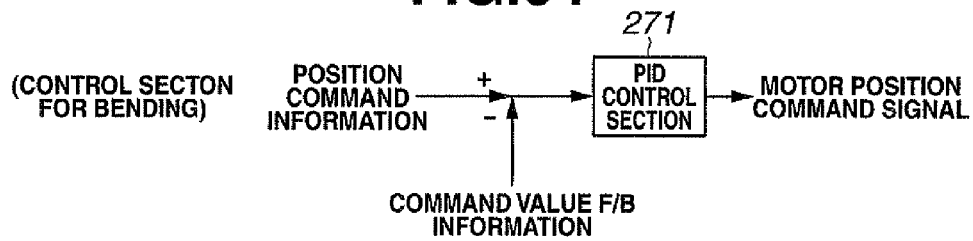
FIG. 64 relates to the first variation of the fourth embodiment and is a block line diagram showing the bending control section shown in FIG. 62.
Figure 65:
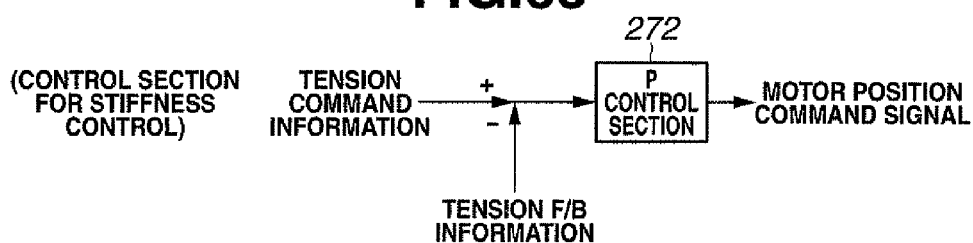
FIG. 65 relates to the first variation of the fourth embodiment and is a block line diagram showing the control section for stiffness control shown in FIG. 62.

FIGS. 61 to 65 are for explaining a first variation of the fourth embodiment, wherein: FIG. 61 is a configuration diagram showing a configuration of an entire endoscope apparatus according to a fourth variation; FIG. 62 is a block diagram showing a specific internal configuration of a servo controller; FIG. 63 is an explanatory diagram explaining characteristics of a bending portion when stiffness control is performed thereon by a controller according to the fourth embodiment; FIG. 64 is a block line diagram showing a bending control section shown in FIG. 62; and FIG. 65 is a block line diagram showing a control section for stiffness control shown in FIG. 62.

As shown in FIG. 61, with the endoscope apparatus 1 according to the first variation, the stiffness setting dial 207 used in the above fourth embodiment has been deleted while tension sensors 263a and 263b are respectively provided which detect respective tension states of the bending operation wires 230a and 230b and output the same to the controller 5.

In other words, by respectively providing the tension sensors 263a and 263b, it is now possible to detect a stiffness state of the bending portion 14 or the entire insertion portion 9 including the bending portion 14 when stiffness control is being performed.

The controller 5 acquires detection results by the tension sensors 263a and 263b or, in other words, tension F/B information, and when stiffness control is being performed, controls rotational driving of each of the motors 227a and 227b based on stiffness command information instructed by the operation command section 7 and the tension F/B information to perform stiffness control of the bending portion 14 or the entire insertion portion 9.

The controller 5 is also capable of performing position command control of the bending portion 14 in the same manner as in the fourth embodiment, and, as a result, is capable of executing either one of the modes of position command control and stiffness command control.

More specifically, the operation command section 7 is provided with mode designating section (not shown) that designates a mode representing bending position command control and a mode representing stiffness command control and outputs designated mode command information. Mode command information from the mode designating section is to be outputted to the servo controller 36A in the controller 5.

FIG. 62 shows a specific internal configuration of the servo controller 36A respectively provided at each motor 227a and 227b.

As shown in FIG. 62, the servo controller 36A according to the first variation includes: a mode discriminating section 270 that discriminates whether the current mode is the bending position command control mode or the stiffness command control mode based on mode command information from the mode designating section of the operation command section 7; a PID control section 271 (refer to FIG. 64) that is a bending control section that creates and outputs an operation output value signal (that is a driving signal and which is also referred to as a motor position command signal) for bending position command control which is necessary for executing the bending position command control mode based on position command information (servo command value signal) and position F/B information; a P control section 272 (refer to FIG. 65) that is a control section for stiffness control that creates and outputs an operation output value signal (that is a driving signal and also referred to as a motor position command signal) for stiffness command control which is necessary for executing the stiffness command control mode based on stiffness command information and tension F/B information; and a switching section 264 that selectively outputs either one of an output of the PID control section 271 or an output of the P control section 272 based on the discrimination result of the mode discriminating section 270 and outputs the same to a relevant motor 227a, 227b.

Accordingly, when the discrimination result of the mode discriminating section 270 is the bending position command control mode, the switching section 264 outputs a driving signal (motor position command signal) from the PID control section 271 that is a bending control section to the designated motor 227a or 227b.

In this case, as shown in FIG. 64, the PID control section 271 that is the bending control section creates and outputs a driving signal (also referred to as a motor position command signal) for bending position command control through PD control such as proportional/differential control based on position command information (servo command value signal) and position F/B information. Consequently, bending movement of the bending portion 14 based on position command information is caused when the driving signal for bending position command control is supplied to the designated motor 227a or 227b via the switching section 264 and driving of the motor 227a or 227b is controlled.

On the other hand, when the discrimination result of the mode discriminating section 270 is the stiffness command control mode, the switching section 264 outputs a driving signal (motor position command signal) from the P control section 272 that is a control section for stiffness control to the designated motor 227a or 227b.

In this case, as shown in FIG. 65, the P control section 272 that is the control section for stiffness control creates and outputs a driving signal (also referred to as a motor position command signal) for stiffness command control through P control such as proportional control based on stiffness command information supplied from the operation command section 7 and tension F/B information. Consequently, stiffness of the bending portion 14 is controlled in a state where the attitude (bending direction) thereof during bending driving is maintained as described with respect to the fourth embodiment when a driving signal for stiffness command control is supplied to the designated motor 227a or 227b via the switching section 264 to control driving and, at the same time, a driving signal for bending position command control is supplied to the other motor 227b or 227a.

As described with respect to the fourth embodiment, during execution of the stiffness command control mode, for example, when a driving signal for stiffness command control is supplied to the motor 227a to drive the same, a driving signal for bending position command control is invariably supplied to the other motor 227b to drive the same.

In other words, as shown in FIG. 63, by equalizing the pulling force of the spring 200b on the side of the bending operation wire 230b connected to the motor 227b during bending driving and the pulling force of the spring 200a on the side of the bending operation wire 230a connected to the motor 227a during stiffness changing driving, the bending portion 14 attains a state where stiffness is acquired while retaining the bending shape thereof in the same manner as in the fourth embodiment.

Therefore, according to the present variation, it is now possible to perform stiffness command control in a state where bending position command control of the bending portion 14 is performed, thereby enabling insertability of the insertion portion 9 to be even more enhanced than in the second embodiment.

Figure 66:
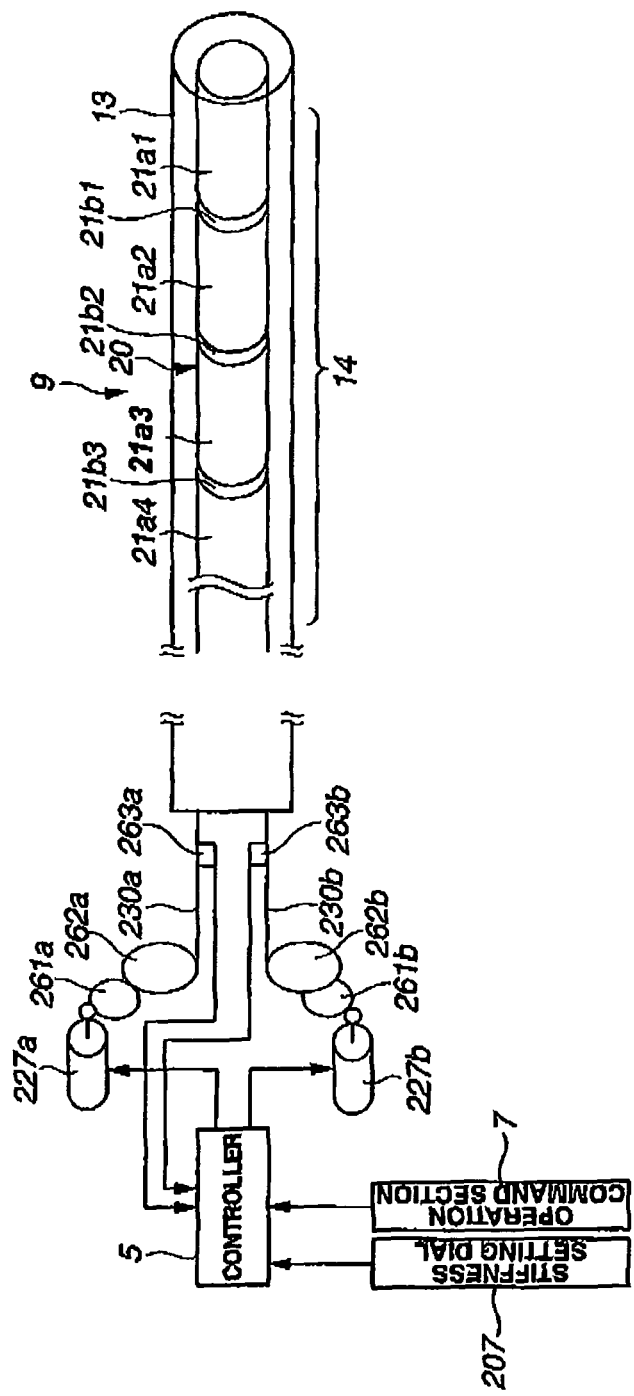
FIG. 66 relates to a second variation of the fourth embodiment and is a configuration diagram showing a configuration of an entire endoscope apparatus according to the second variation.
Figure 67:
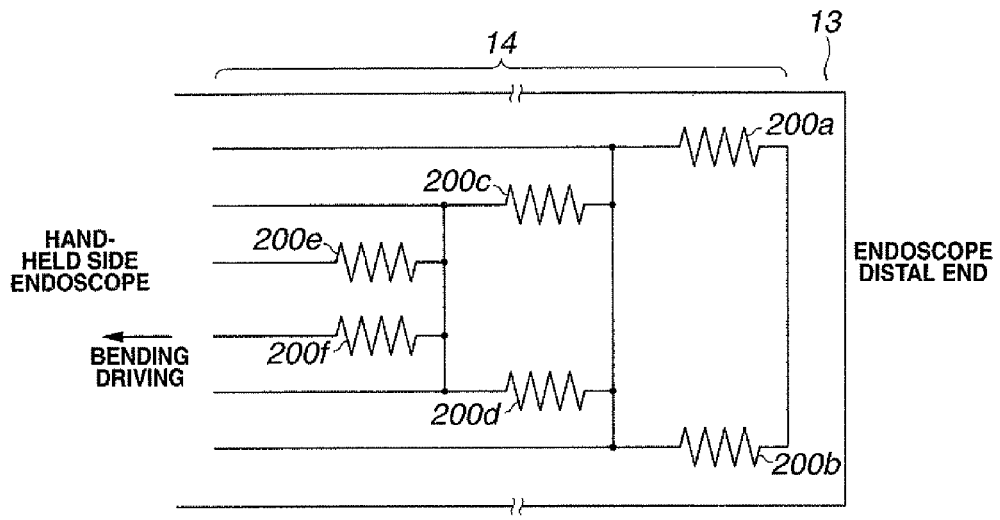
FIG. 67 relates to the second variation of the fourth embodiment and is an explanatory diagram explaining characteristics of a bending portion when stiffness control is performed thereon by a controller.

FIGS. 66 and 67 are diagrams explaining a second variation of the fourth embodiment, wherein; FIG. 66 is a configuration diagram showing a configuration of an entire endoscope apparatus according to the fourth variation; and FIG. 67 is an explanatory diagram explaining characteristics of a bending portion when stiffness control is performed thereon by a controller according to the second variation. For FIGS. 66 and 67, like components to the third and fourth embodiments and the first variation of the fourth embodiment are assigned like reference characters, and descriptions thereof will be omitted. Thus, only different parts will be described.

As shown in FIG. 66, the endoscope apparatus 1 according to the second variation combines the configurations of the second embodiment and the first variation, and is configured using a bending portion 14 having a multi-joint link structure approximately similar to that of the third embodiment.

In other words, the endoscope apparatus 1 according to the second variation includes the stiffness setting dial 207 and the tension sensors 263a, 263b in the same manner as the fourth embodiment, and further includes a bending portion 14 configured so as to include a plurality of link members 21a1 to 21an (where, for example, n=4) respectively bendable in two directions, namely, upward and downward.

In the same manner as the first variation, the controller 5 according to the second variation performs bending position command control and stiffness command control so that the bending portion 14 attains a stiffness state while retaining the bending direction (bending state) of the bending portion 14 during bending driving. However, the controller 5 is also capable of performing bending position command control and stiffness command control on an arbitrary designated link member 21a among a plurality of link members 21a.

Characteristics of the bending portion 14 having a plurality of link members 21a of this case is shown in FIG. 67. In other words, as shown in FIG. 67, the bending portion 14 acquires characteristics represented by: two springs 200a and 200b indicating load quantities applied to two bending operation wires of the distal end-side link member 21a1; two springs 200c and 200d indicating load quantities applied to two bending operation wires of the second-stage link member 21a2; two springs 200e and 200f indicating load quantities applied to two bending operation wires of the third-stage link member 21c; and two springs 200n and 200n indicating load quantities applied to two bending operation wires of a subsequent member 21an.

For example, when stiffness command control is performed during bending driving of the second-stage link member 21a2 and the third-stage link member 21a3, forces respectively pulling the springs 200c and 200d of the link member 21a2 are equalized, and, at the same time, forces respectively pulling the springs 200e and 200f of the link member 21a3 are equalized.

However, since the configuration shown in FIG. 67 is a physical model in which a plurality of springs counter each other, when actually attempting to perform stiffness command control of an arbitrary designated link member 21a among a plurality of link members 21a using the controller 5, interference from a bending operation wire, a driving pulley and a free pulley disposed between the link member 21a and a link member 21a consecutively connected to the link member 21a occurs, thereby causing bending of the distal end-side link member 21a1.

For this reason, a correction computing section, not shown, that performs computational processing for correcting bending movement of the distal end-side link member 21a1 when stiffness command control is performed on an arbitrary link member 21a is provided at the servo controller 36A of the controller 5.

Figure 68A:
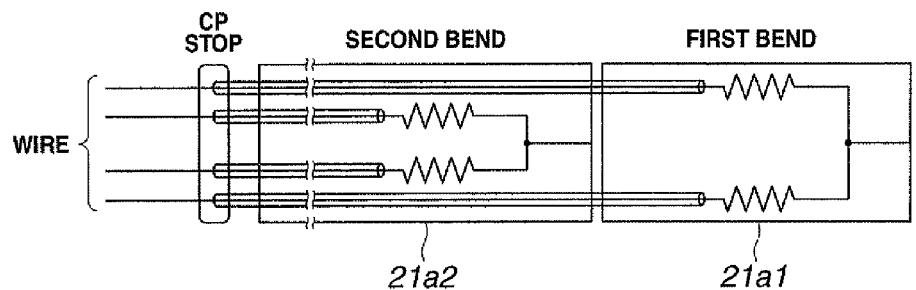
FIG. 68A relates to the second variation of the fourth embodiment and is a principle diagram of a bending portion for explaining effects.
Figure 68B:
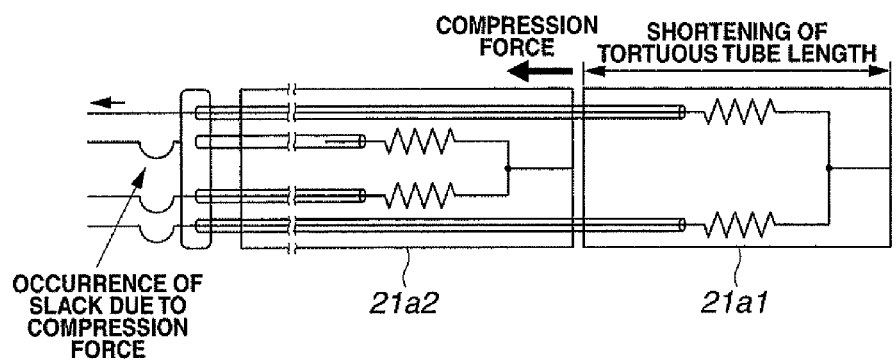
FIG. 68B relates to the second variation of the fourth embodiment and is an explanatory diagram showing a state in which slack has occurred at a wire due to the shortening of tortuous tube length as a result of the pulling of a wire at a first bending portion.
Figure 68C:
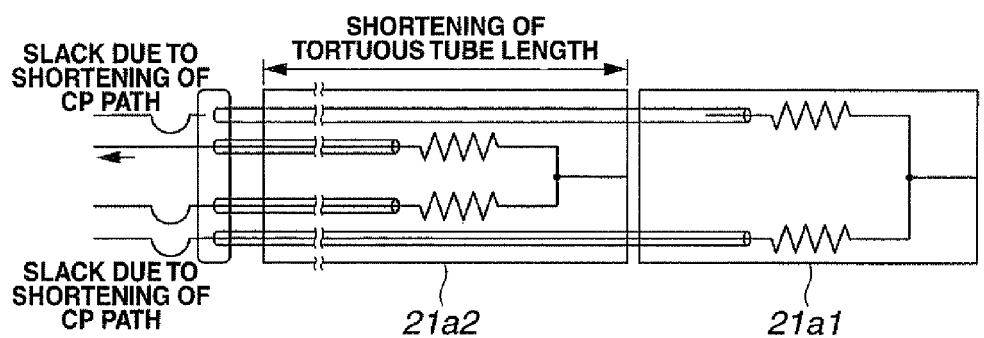
FIG. 68C relates to the second variation of the fourth embodiment and is an explanatory diagram showing a state in which slack has occurred at a wire due to the shortening of tortuous tube length of a second bending portion as a result of the pulling of a wire at the second bending portion.

FIG. 67 shows a principle model diagram, while FIGS. 68A to 68C show effect principle diagrams. More specifically: FIG. 68A is a principle diagram of a bending portion for explaining effects; FIG. 68B shows a state in which slack has occurred at a wire due to the shortening of tortuous tube length as a result of the pulling of a wire at a first bending portion; and FIG. 68C shows a state in which slack has occurred at a wire due to the shortening of tortuous tube length of a second bending portion as a result of the pulling of a wire at the second bending portion.

In FIG. 68A, let us assume that, for example, the pulling wire 200a (refer to FIG. 67) is pulled in order to drive the first bending portion. At this point, as shown in FIG. 68B, tortuous tube length is shortened due to wire pulling of the pulling wire 200a and, at the same time, a compression force is applied to the second bending portion side. As a result, the wire pathways of the pulling wires 200b and 200c are shortened and a wire slack occurs.

In addition, when the pulling wire 200b is pulled in the state shown in FIG. 68A in order to drive the second bending portion, compression of the tortuous tube length of the second bending portion causes a similar slack on the pulling wire 200a.

Consequently, driving affects bending portions other than the bending portion of which driving is desired. In other words, when there are a plurality of bending portions, correction is to be performed on bending portions other than the desired bending portion.

Next, a configuration and advantageous effects of the correction computing section will be described.

As for the correction method, as is described in the above fourth embodiment, wire load detecting section 263 is respectively disposed for each bending operation wire, and prior to the driving of a desired stiffness setting bending portion, a setting value storing section 274 (refer to FIG. 69) that is means for storing a stiffness setting value other than the desired stiffness setting bending portion is incorporated.

Figure 69:
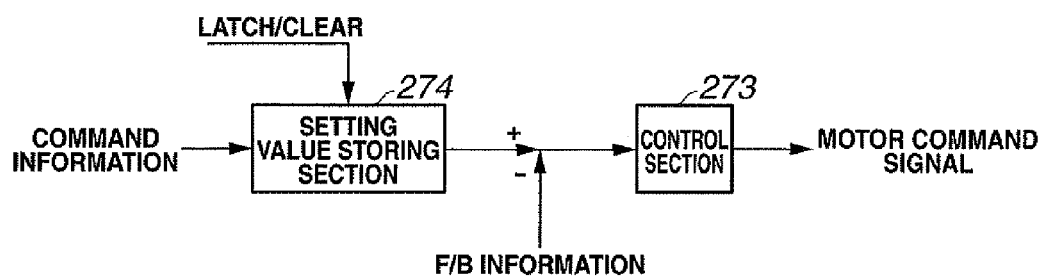
FIG. 69 relates to the second variation of the fourth embodiment and is a block line diagram showing a control section.

As shown in FIG. 69, correction is performed by providing the setting value storing section 274 that stores data in addition to the respective inputting sections of position commands, stiffness commands and tension commands shown in the block line diagrams (FIGS. 62, 64 and 65) described above.

At the setting value storing section 274, stiffness setting of a desired bending portion is performed, and at the same time, a latch signal is activated at a driving section other than the desired bending portion to retain a value of a state prior to the stiffness setting. During stiffness setting at the desired bending portion, the setting value storing section 274 functions to pass command information to the control section 273 in real time.

This enables correction to be performed even when interference occurs at each bending portion.

In addition to performing bending correction of the distal end-side link member 21a1 during execution of stiffness command control, the correction computing section will also be able to perform computational processing for correcting bending movements of other link members 21a which are anticipated due to the execution of stiffness command control.

In the second variation, the controller 5 is arranged so that, when performing stiffness command control of the bending portion 14 having a plurality of link members 21a, stiffness command control is performed so as to satisfy the following stiffness condition.

For example, assuming that the bending portion 14 is constituted by four link members 21a1 to 21a4, a relationship among the respective stiffness levels of each link member 21a may be expressed as:

Fourth-stage link member 21a4>third-stage link member 21a3>second-stage link member 21a2>distal end-side link member 21a1.

Therefore, as described above, with the endoscope apparatus according to the second variation, even if the bending portion 14 is configured so as to have a multi-joint link structure, it is now possible to perform stiffness command control on an arbitrarily designated link member 21a among the plurality of link members 21a in a state where bending position command control is performed on the bending portion 14 in the same manner as in the above third and fourth embodiments and the first variation of the fourth embodiment.

While two bending directions of upward and downward of the bending portion 14 have been described in the first variation, the present invention is not limited to this arrangement. Instead, the bending portion 14 may be configured so that bending movement is enabled in four bending directions of upward, downward, leftward and rightward, and at the same time, a motor that is the driving section 10b and a bending operation wire are provided.

For the third embodiment according to the present invention, while point-locking a two-dimensional position and direction of the distal end-side link member 21a1 among the plurality of link members 21a has been described, the present invention is not limited to this example. Instead, the present invention may be configured so that a three-dimensional position and direction are point-locked.

For the third embodiment according to the present invention, while the bending portion 14 having the insertion portion driving mechanism constituting a manipulator has been described as being provided at the insertion portion 9 of the endoscope 2, the bending portion 14 may be arranged to be provided at an insertion portion of an endoscope insertion aiding device that aids the insertion of the insertion portion 9 into a tube cavity by allowing insertion of the insertion portion 9 of the endoscope 2.

Figure 70:
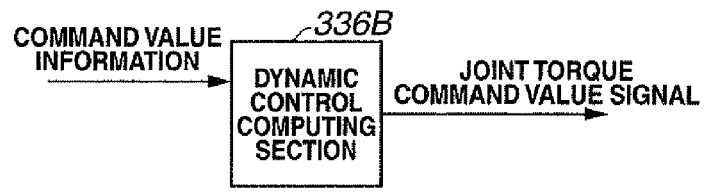
FIG. 70 relates to a fifth embodiment of the present invention and is a block diagram showing a kinematics computing section included in a servo controller.
Figure 71:
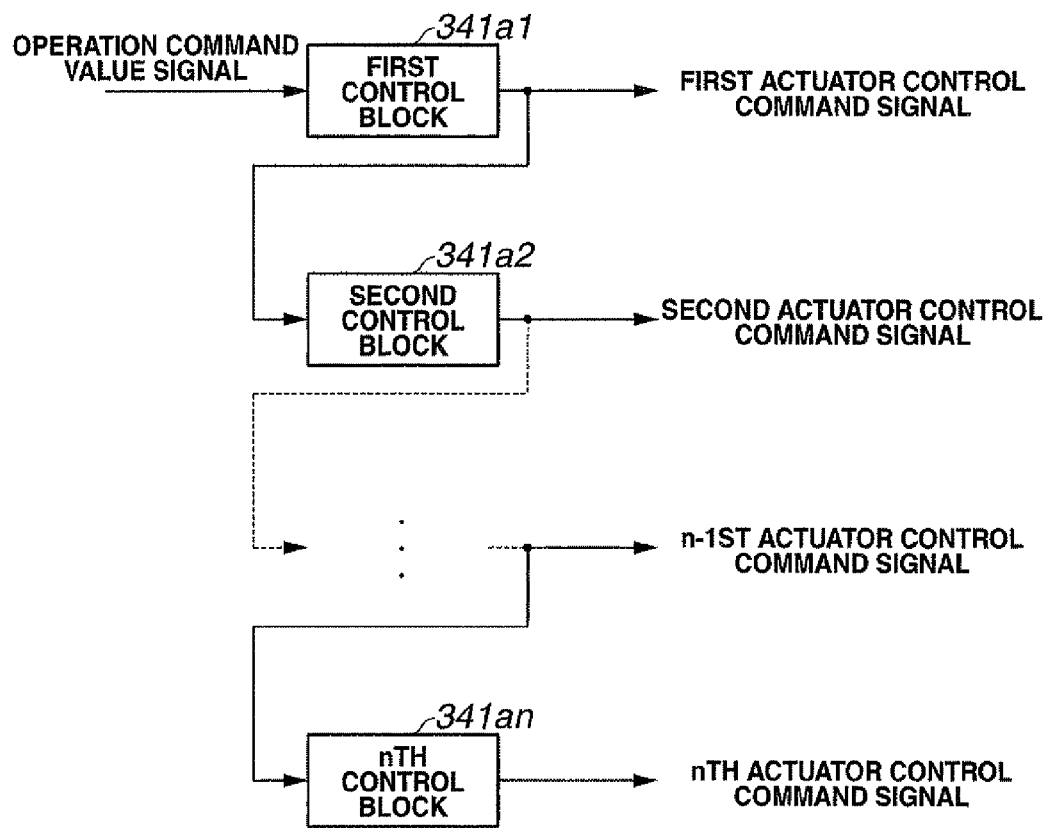
FIG. 71 relates to the fifth embodiment of the present invention and is a block diagram showing an overall configuration of a servo controller provided at each actuator control block, according to the fifth embodiment of the present invention.
Figure 72:
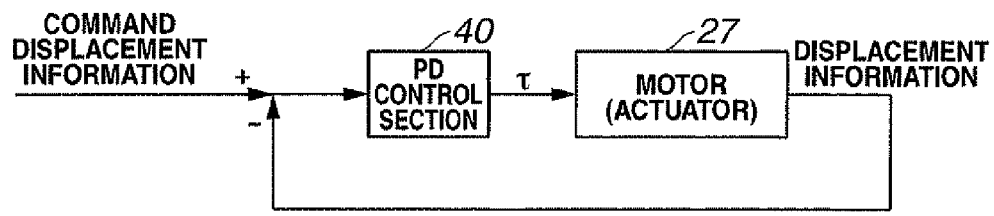
FIG. 72 relates to the fifth embodiment of the present invention and is a block line diagram of the control block shown in FIG. 71.
Figure 73:
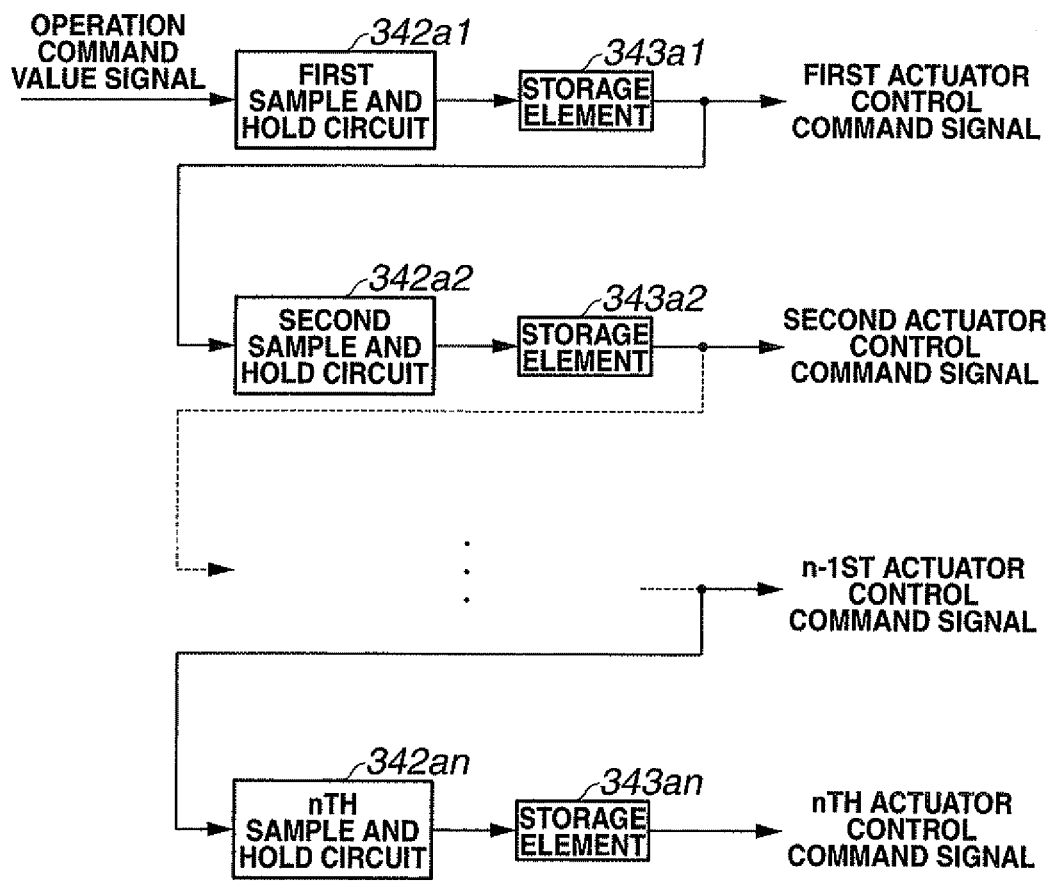
FIG. 73 relates to the fifth embodiment of the present invention and is a block diagram showing a specific configuration of the control block shown in FIG. 71.

Next, a fifth embodiment of the present invention will be described with reference to FIGS. 70 to 73. FIGS. 70 to 73 are diagrams explaining specific configurations and control operations of a servo controller according to the fifth embodiment of the present invention, wherein: FIG. 70 is a block diagram showing a kinematics computing section included in a servo controller; FIG. 71 is a block diagram showing an overall configuration of a servo controller provided at each actuator control block; FIG. 72 is a block line diagram of the control block shown in FIG. 71; and FIG. 73 is a block diagram showing a specific configuration of the control block shown in FIG. 71.

The present fifth embodiment primarily differs from the above first embodiment in that, with an endoscope 2 provided with a bending portion 14 having a multi-joint link structure, insertability of an insertion portion 9 is enhanced by controlling driving of the bending portion 14 so that an angle of a distal end-side link member 21a1 of the bending portion 14 sequentially shifts along proximal end-side link members 21a1 to 21an. Otherwise, descriptions on points similar to the first embodiment described above will be omitted.

A servo controller 36A connected to a command control section 5A according to the present fifth embodiment is arranged so that, when respectively controlling the rotational movement of each of the plurality of link members 21a1 to 21an that constitute the bending portion 14, computational processing based on a dynamic control computing section, to be described later is performed.

More specifically, as shown in FIG. 70, a dynamic control computing section 336B is provided at the servo controller 36A. By performing signal processing (filtering) of a temporal/frequency domain based on a supplied operation command value signal (command value information), the dynamic control computing section 336B creates an operation output value signal (driving signal) necessary for controlling the driving section 10b provided at the actuator control block 31.

Next, a specific configuration and a shift control method of the servo controller 36A for performing computational processing based on signal processing of the temporal/frequency domain will be described with reference to FIGS. 71 to 73.

As shown in FIG. 71, the servo controller 36A includes a control block 341 (first to nth control blocks 41a1 to 41an).

An operation command value signal including a servo command value signal at the distal end-side link member 21a1 is supplied to the control block 341.

Based on the supplied command value signal and a position F/B signal, the control block 341 performs computational processing for obtaining an actuator control command signal that is a joint torque command value signal corresponding to a link member 21a by the dynamic control computing section 336B, and outputs the signal to a corresponding driving section 10b and a subsequent-stage control block 341.

First to nth actuator control command signals outputted from the control block 341 is arranged to be connected to command displacement information shown in FIG. 72. Based on the supplied command value signal and a position F/B signal that is displacement information of the motor 27 obtained from the sensor 38, the PD control section 40 is used to perform PD control such as known proportional/differential control to create the actuator control command signal (driving signal), which is then supplied to the motor 27 to rotationally control the same.

In the present embodiment, the number of provided servo controllers 36A corresponds to the number of the first to nth actuator control blocks 31a1 to 31an. Therefore, the controller 5 includes a plurality of control blocks 341a to 341an whose number corresponds to the number of the first to nth actuator control blocks 31a1 to 31an.

Accordingly, as shown in FIG. 71, the first control block 341a corresponding to the distal end-side link member 21a1 is connected to the command control section 5A (refer to FIG. 9).

A second control block 341a2 corresponding to the second-stage link member 21a2 and to which is inputted an output signal (first actuator control command signal) of the first control block 341a1 is connected to the first control block 341a1.

A third control block 341a3 (not shown) corresponding to the third-stage link member 21a3 and to which is inputted an output signal (second actuator control command signal) of the second control block 341a2 is connected to the second control block 341a2.

Henceforth, by performing connections in the same manner, an n−1st control block 341a(n−1) corresponding to the n−1st-stage link member 21a(n−1) is connected so as to acquire an output signal of a previous-stage control block 341, and a nth control block 341an corresponding to the nth-stage link member 21an is connected so as to acquire an output signal of the previous-stage n−1st control block 341a(n−1).

The operation command value signal is for instructing a joint angle (angle) formed by the distal end-side link member 21a1 and a link member 21a2 contiguous to the link member 21a. Similarly, the first to nth actuator control command signals are for instructing joint angles (angles) formed by a corresponding link member 21a and a link member 21a consecutive thereto.

Through such a configuration, an operation command value signal (mainly of an angle) that drives the distal end-side link member 21a1 can be transmitted sequentially along a time series to link members 21a on the subsequent stage side.

Contents of the dynamic control computing section 336B will be described below.

FIG. 73 shows a specific block configuration of the plurality of first to nth control blocks 341.

As shown in FIG. 73, the control block 341 is configured to include a sample and hold circuit 342 and a storage element 343.

The sample and hold circuit 342 samples the supplied operation command value signal, and holds the sampled operation command value signal for a presetting time before outputting the same to the storage element 343.

The storage element 343 is storage section that temporarily stores the supplied operation command value signal, and when an operation command value signal is newly supplied, outputs the stored operation command value signal as an actuator control command signal.

Therefore, as described above, since the number of provided control blocks 341 constituted by the sample and hold circuit 342 and the storage element 343 correspond to the number of the first to nth actuator control blocks 31a1 to 31an, a plurality of first to nth sample and hold circuits 342a1 to 342an is connected to a plurality of storage elements 343a1 to 343an as shown in FIG. 73.

In other words, an operation command value signal of the distal end-side link member 21a1 is first sampled by the first sample and hold circuit 341a1, whereby the sampled operation command value signal is held for a presetting time and outputted to the storage element 343a1.

When the operation command value signal is supplied to the storage element 343a1, the operation command value signal is temporarily stored in the storage element 343a1. An operation command value signal already stored is supplied as a first actuator control command value signal to the motor 27 corresponding to the distal end-side link member 21a1 of the driving section 10b and to the second sample and hold circuit 342a2 of the second-stage that is the subsequent stage.

Consequently, rotational control of the motor 27 based on the first actuator control command value signal causes the distal end-side link member 21a1 to rotationally move by an angle based on the operation command value signal.

Then, the first actuator control command value signal is sampled by the second sample and hold circuit 342a2, whereby the sampled operation command value signal is held for a presetting time and outputted to the storage element 343a2.

When the operation command value signal is supplied to the storage element 343a2, the operation command value signal is temporarily stored in the storage element 343a2. An operation command value signal already stored is supplied as a second actuator control command value signal to the motor 27 corresponding to the second-stage link member 21a2 of the driving section 10b and to the third sample and hold circuit 342a3 (not shown) of the third-stage (not shown) that is the subsequent stage.

Consequently, rotational control of the motor 27 based on the second actuator control command value signal causes the second-stage link member 21a2 to rotationally move after the lapse of the time preset by the second sample and hold circuit 342a2 by an angle based on the operation command value signal or, in other words, the same angle as the distal end-side link member 21a1.

In this manner, an actuator control command signal of the previous stage is similarly sampled by the third-stage link member 21a2, . . . , the n–1st-stage link member 21a(n-1), and the nth t-stage link member 21an, whereby, after a lapse of a presetting time, the actuator control command signal is supplied to a corresponding motor 27 via the storage element 343. As a result, the respective link members 21a rotationally move in sequence by the same angle as the distal end-side link member 21a1 at each presetting time along a time series.

In other words, the bending portion 14 performs a bending movement such that the angle of the distal end-side link member 21a1 sequentially shifts along the plurality of proximal end-side link members 21a2 to 21an consecutive thereto in a time series for each sample and hold time (presetting time).

With the endoscope apparatus 1 as described above, when inserting the insertion portion 9 into the large intestine, the operator inserts the insertion portion 9 via the anus. Then, when the distal end portion 13 of the insertion portion 9 reaches the sigmoid colon segment, the servo controller 36A performs bending movement of the distal end-side link member 21 also that a spatial direction (angle) designated by the operation command section 7 is assumed.

Consequently, since the distal end-side link member 21a1 is bent by the designated angle, further insertion along the intestinal wall of the sigmoid colon segment is enabled.

After the lapse of a preset setting time (hold time), the second-stage link member 21a2 contiguous to the distal end-side link member 21a1 performs a bending movement in the same direction (angle) as the distal end-side link member 21a1.

Henceforth, the third-stage link member 21a3 and the plurality of link members subsequent thereto similarly perform bending movement so as to sequentially shift in the same direction (angle) as the distal end-side link member along a time series at each setting time.

Accordingly, the bending portion 14 will be inserted while performing bending movements such that, in association to an insertion operation, the angle of the distal end-side link member 21a1 sequentially shifts from the distal end-side to the proximal end-side so as to conform to the shape of the sigmoid colon segment.

Consequently, it is now possible to pass through the sigmoid colon segment, which conventionally presented difficulties for insertion, in an easy manner. Therefore, since insertions into deep portions of the large intestine can be more readily performed, insertability can be improved.

In the endoscope apparatus 1 according to the fifth embodiment, the plurality of link members 21a constituting the bending portion 14 performs bending movements so that the angle of the distal end-side link member 21a1 sequentially shifts at each setting time towards the proximal end-side link members 21a to 21an. However, instead of using the angle of the distal end-side link member 21a1, it also is possible to designate an arbitrary link member 21a (also referred to as an object axis) whose angle is to be shifted. The setting time (hold time) can also be set arbitrarily. Such a first variation of the fifth embodiment is shown in FIG. 74.

Figure 74:
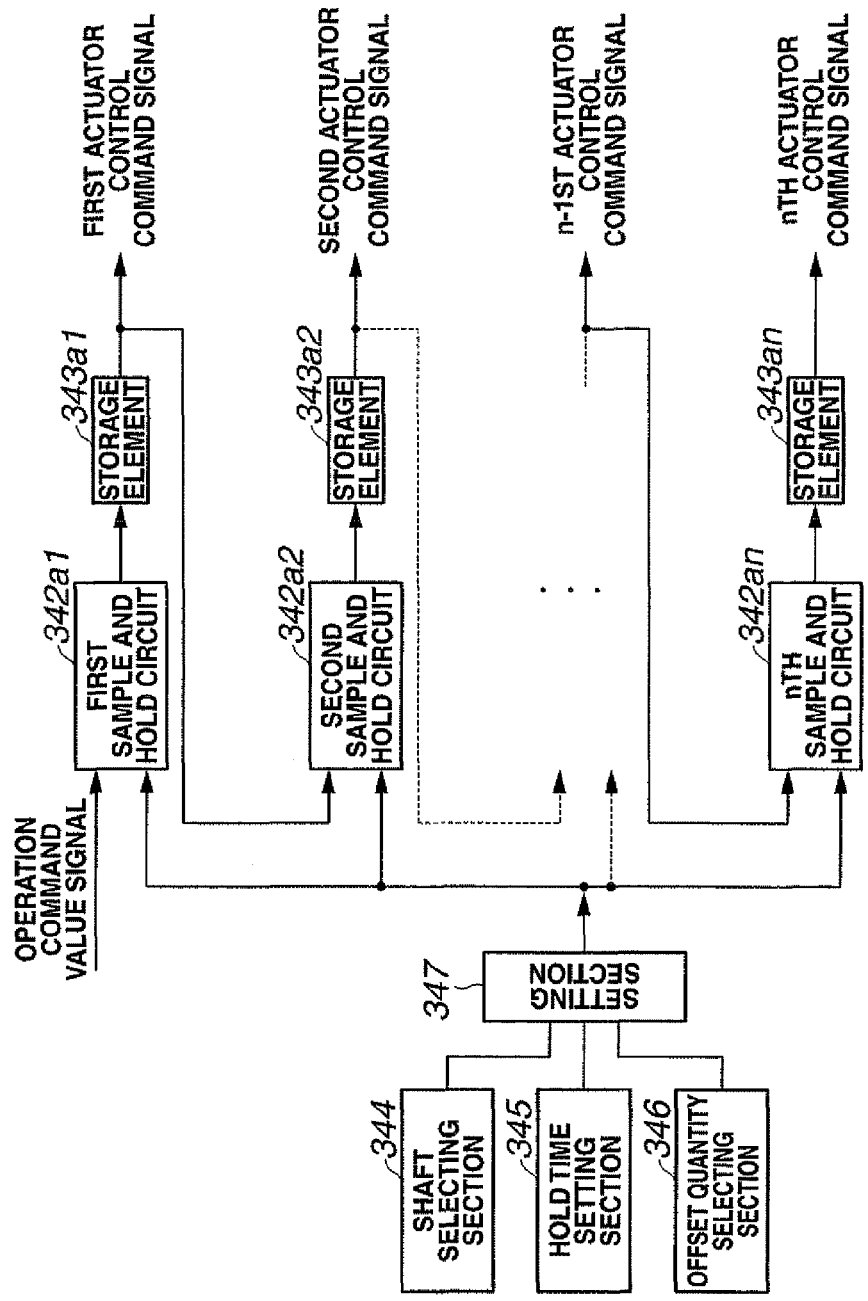
FIG. 74 is a block diagram showing a first variation of the fifth embodiment.

FIG. 74 is a block diagram showing the first variation of the fifth embodiment.

As shown in FIG. 74, a controller 5 according to the first variation is provided with: a shaft selecting section 344 as selecting section; a hold time setting section 345 as time changing section; an offset quantity selecting section 346; and a setting section 347.

The shaft selecting section 344 designates a shaft or, in other words, an arbitrary link member 21a whose angle is to be subjected to shift control and outputs a designation signal to the setting section 347. In other words, by providing the shaft selecting section 344, a shaft whose angle is to be shifted is no longer limited to that of the distal end-side link member 21a1, and the angle of another arbitrary shaft (link member 21a) can be shifted.

The hold time setting section 345 is capable of arbitrarily setting sample and hold times (setting times) of the first to nth sample and hold circuits 342a1 to 342an, and outputs a setting time that has been set to the setting section 347. In other words, by providing the hold time setting section 345, it is now possible to freely set a movement travel time among the respective link members 21a in which shifting is sequentially performed in a time series from the distal end-side to the proximal end-side.

For example, when performing insertion while shift control of the bending portion 14 of the insertion portion 9 is performed in a slow manner, the hold time (setting time) may be set long by the hold time setting section 345. Conversely, when performing insertion while shift control of the bending portion 14 of the insertion portion 9 is performed in a speedy manner, the hold time (setting time) may be set short by the hold time setting section 345.

The offset quantity selecting section 346 selects a quantity in which the direction of the link member 21a selected by the shaft selecting section 344 or the link member 21a that is preset by the operation command section 7 is to be changed, and outputs an offset command value signal to the setting section 347. In other words, by providing the offset quantity selecting section 346, when changing the direction of the designated link member 21a, it is now possible to perform adjustment by subtly changing (offsetting) the direction of the designated link member 21a by only the quantity based on the offset command value signal.

Consequently, a designation signal from the shaft selecting section 344, a setting signal from the hold time setting section 345 and an offset command value signal from the offset quantity selecting section 346 are supplied to the setting section 347 which then performs setting based on the control signals.

In other words, when a designation signal is supplied from the shaft selecting section 344, the setting section 347 sets a link member 21a based on the designation signal as a link member 21a from which shift control is to be started. When a setting signal is supplied from the hold time setting section 345, the setting section 347 sets a hold time of a relevant sample and hold circuit 342 so as to match a hold time based on the setting section. Further, when an offset command value signal is supplied from the offset quantity selecting section 346, the setting section 347 performs setting so that the direction of the designated link member is changed by only the quantity based on the offset command value signal.

Consequently, according to the first variation, in addition to achieving the same advantageous effects as the fifth embodiment, it is now possible to arbitrarily set a movement time of the respective link members 21a in which the angle of the distal end-side link member 21a1 is sequentially shift-controlled towards proximal end-side link members 21a2 to 21an. It is also possible to arbitrarily set a link member 21a from which shift control is to be started, and to arbitrarily set an offset quantity of the designated link member 21a. Consequently, it is now possible to perform optimum shift control in accordance with an insertion state, thereby further enhancing insertability.

When inserting the bending portion 14 of the insertion portion 9 into a tube cavity such as the large intestine while performing shift control of the bending portion 14, insertability can be further enhanced by taking the insertion quantity or, in other words, the operation quantity of the insertion portion 9 into consideration. Such a second variation of the fifth embodiment is shown in FIG. 75.

Figure 75:
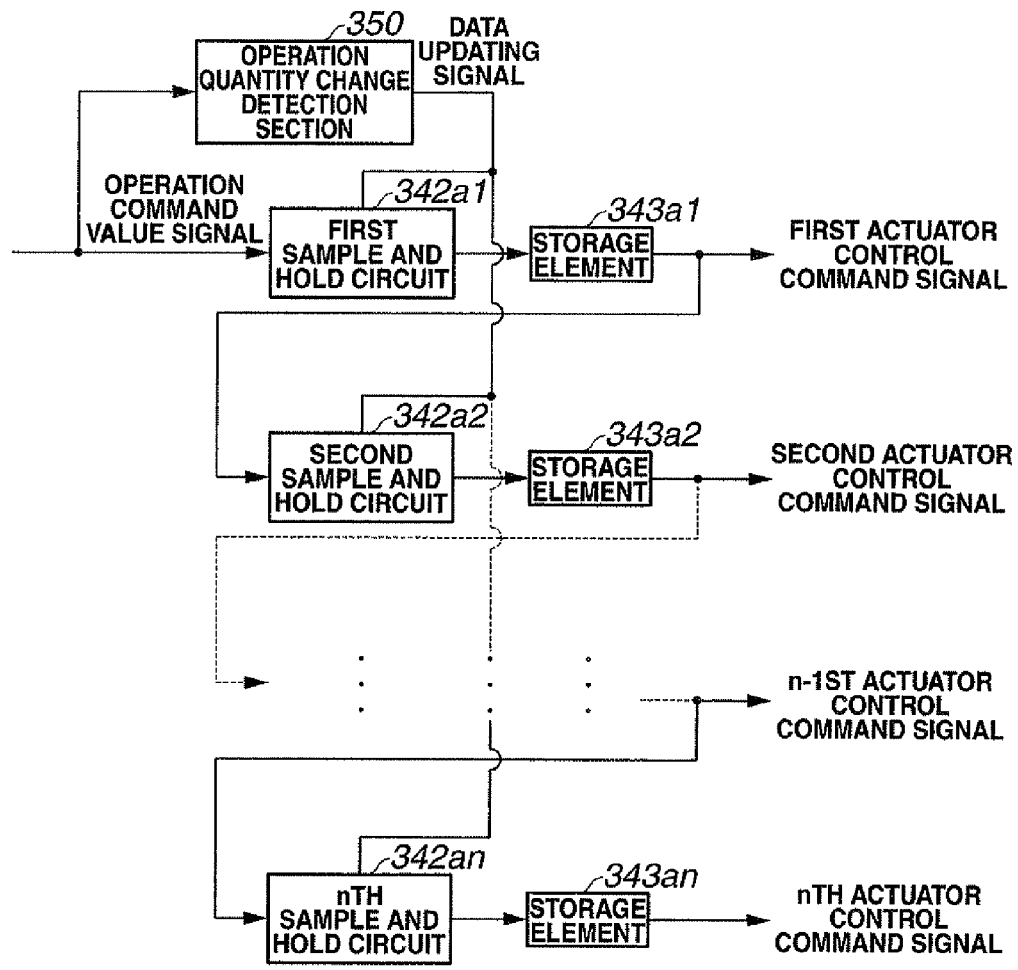
FIG. 75 is a block diagram showing a second variation of the fifth embodiment.

FIG. 75 is a block diagram showing the second variation of the fifth embodiment.

As shown in FIG. 75, an operation quantity change detecting section 50 is provided at the controller 5 according to the second variation.

The operation quantity change detecting section 350 receives an operation command value signal with respect to the distal end-side link member 21a1 as an input from the command control section 5A, detects an operation quantity of the distal end-side link member 21a1 from the operation command value signal, and outputs a detection result as a data updating signal for updating data of the sample and hold circuit 342 to the first to nth sample and hold circuits 342a1 to 342an.

When the data updating signal is supplied, the first to nth sample and hold circuits 342a1 to 342an simultaneously update their respective data. Therefore, when the operation quantity of the distal end-side link member 21a1 changes, the first to nth sample and hold circuits 342a1 to 342an update data at a speed in accordance to the operation quantity. In other words, the present second variation is arranged so that, when the operation quantity of the distal end-side link member 21a1 changes, shift control is sequentially performed on the plurality of link members 21a contiguous to the distal end-side link member 21a1 in accordance to the variation in operation quantity.

Consequently, since there is no temporal dependency and since shift control can be performed in accordance to the variation in operation quantity of the distal end-side link member 21a1, the insertability of the insertion portion 9 can be enhanced.

Figure 76:
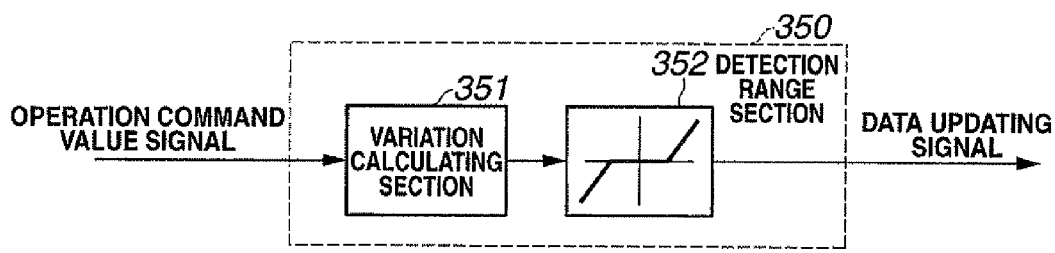
FIG. 76 relates to the second variation of the fifth embodiment of the present invention and is a block diagram showing a specific configuration of the operation quantity change detecting section shown in FIG. 75.
Figure 77:
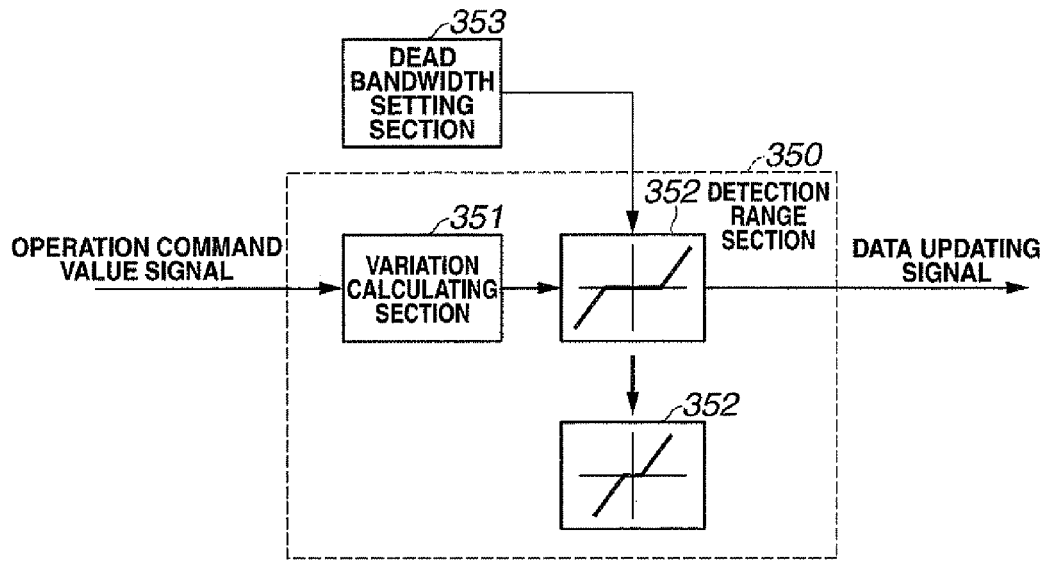
FIG. 77 relates to the second variation of the fifth embodiment of the present invention and is a block diagram showing a configuration in which a blind bandwidth setting section is provided at the operation quantity change detecting section shown in FIG. 75.

With the second variation, in order to prevent unintentional shift control of the bending portion 14 due to a hypersensitive detection of a variation in operation quantity by the operation quantity change detecting section 350, means such as those shown in FIG. 76 or 77 may be provided.

FIG. 76 is a block diagram showing a specific configuration of the operation quantity change detecting section shown in FIG. 75, while FIG. 77 is a block diagram showing a configuration in which a blind bandwidth setting section is provided at the operation quantity change detecting section shown in FIG. 75.

As shown in FIG. 76, the operation quantity change detecting section 350 includes: a variation calculating section 351 that calculates an operation variation of the distal end-side link member 21a1 from an operation command value signal; and a detecting range section 352 that outputs a data updating signal by performing detection from a calculation result of the variation calculating section 351 at a preset detecting level. The detecting range section 352 is capable of arbitrarily setting a detecting level.

Such a configuration enables a detecting level of an operation variation of the distal end-side link member 21a1 by the detecting range section 352 to be arbitrarily set. Therefore, it is now possible to prevent shift control from being intentionally performed on the bending portion 14, thereby enhancing safety.

In addition, with the second variation, as shown in FIG. 77, a dead bandwidth setting section 353 capable of arbitrarily setting a dead bandwidth of a detecting range of the detecting range section 352 shown in FIG. 76 may be provided.

For example, when it is desirable to narrow down the dead bandwidth of a detecting range of the detecting range section 352, the operator operates the dead bandwidth setting section 353 to perform setting so that the dead bandwidth is narrowed down as is the case of the detecting range section 352 indicated in the direction of the arrow shown in the diagram. Obviously, it is also possible to conversely widen the dead bandwidth of the detecting range section 352.

Consequently, detection of an operation variation of the distal end-side link member 21a1 can now be performed over a wide range, thereby contributing towards the improvement of safety.

While a configuration in which the operation quantity change detecting section 350 is provided in the servo controller 36A has been described, the present invention is not limited to this arrangement, and the operation quantity change detecting section 350 may instead be provided in the operation command section 7.

Figure 78:
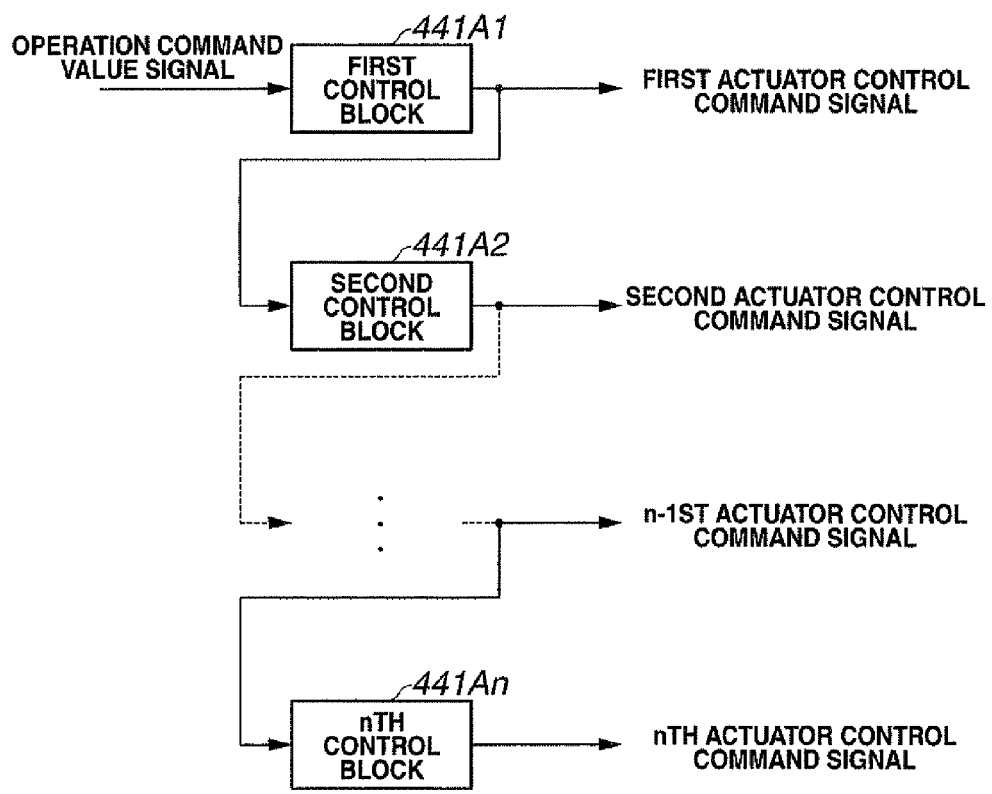
FIG. 78 relates to a sixth embodiment of the present invention and is a block diagram showing an overall configuration of a servo controller provided at each actuator control block.
Figure 79:
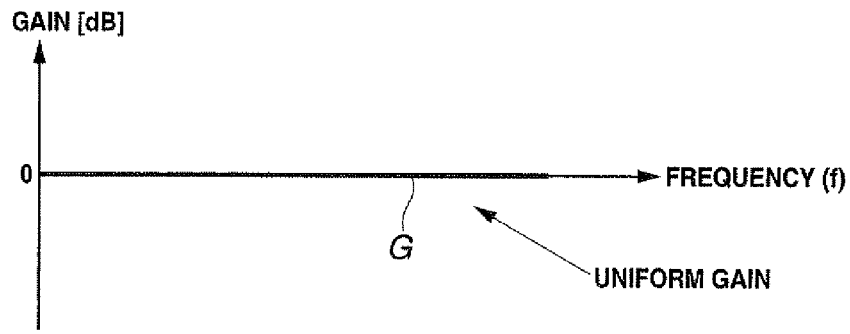
FIG. 79 relates to the sixth embodiment of the present invention and is a graph showing characteristics of gain and frequency of an input/output signal of the control block shown in FIG. 78.
Figure 80:
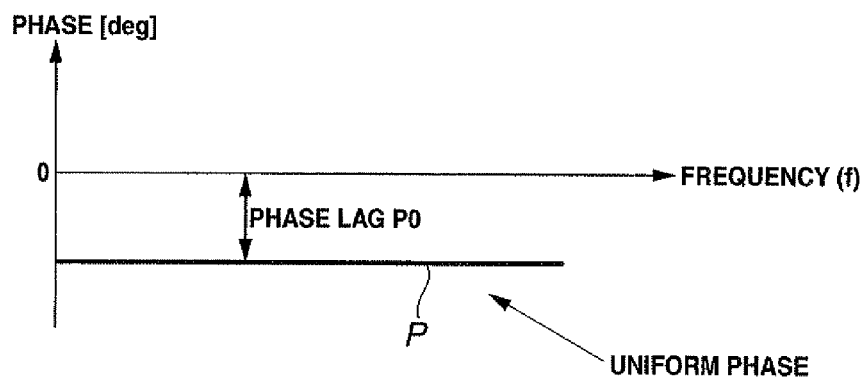
FIG. 80 relates to the sixth embodiment of the present invention and is a graph showing characteristics of phase and frequency of an input/output signal of the control block shown in FIG. 78.
Figure 81:
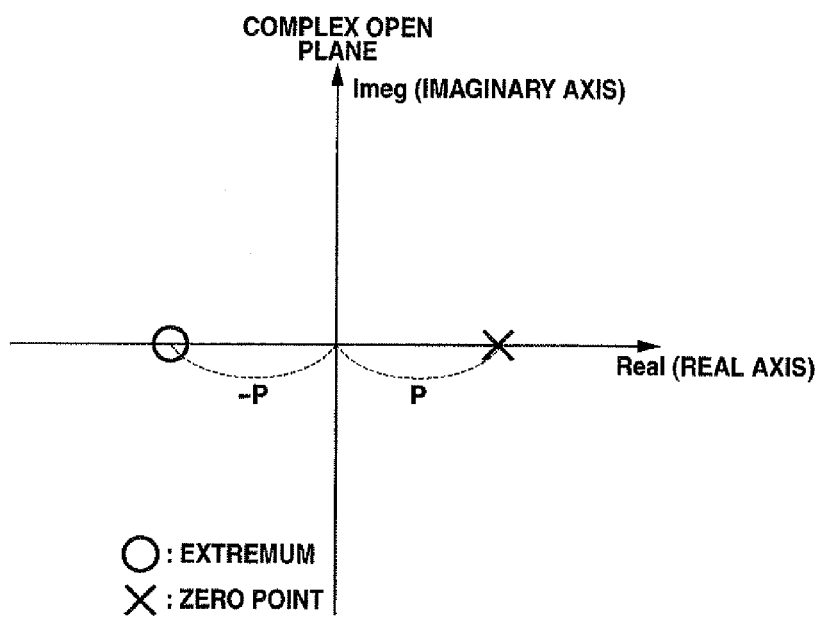
FIG. 81 relates to the sixth embodiment of the present invention and is a diagram showing a state in which an extremum and a zero point on a real axis of a complex open plane are set to be symmetrical with respect to an imaginary axis.
Figure 82:
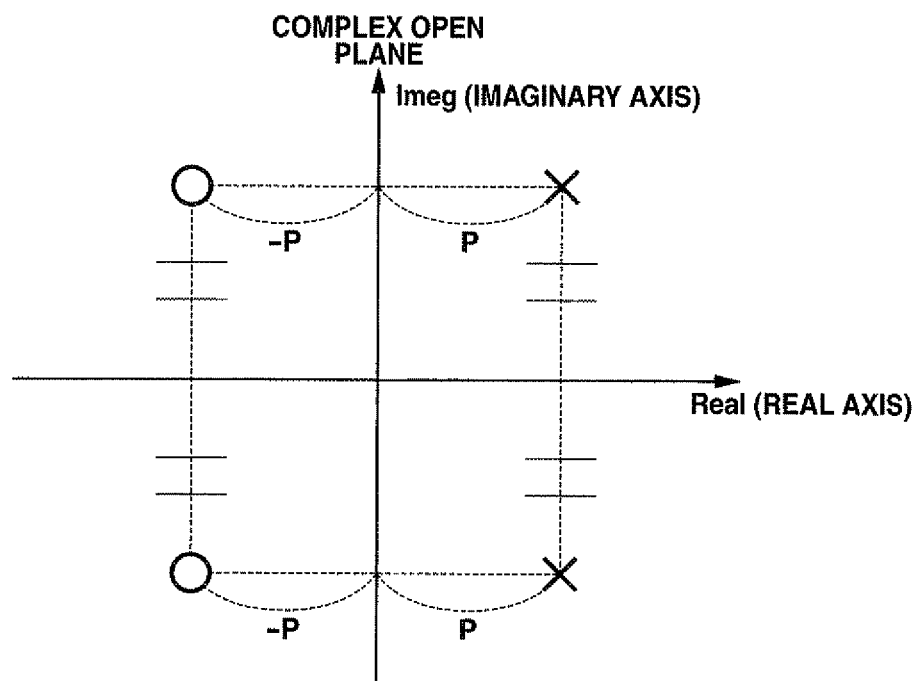
FIG. 82 relates to the sixth embodiment of the present invention and is a diagram showing a state in which extrema and zero points on positive and negative real axes of a complex open plane are set to be symmetrical with respect to an imaginary axis.
Figure 83:
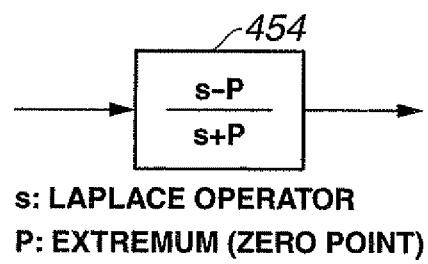
FIG. 83 relates to the sixth embodiment of the present invention and is a block diagram showing a filter section included in the first control block shown in FIG. 78.

Next, FIGS. 78 to 83 are related to a sixth embodiment. FIG. 78 is a block diagram showing an overall configuration of a servo controller provided at each actuator control block. FIG. 79 is a graph showing characteristics of gain and frequency of an input/output signal of the control block shown in FIG. 78. FIG. 80 is a graph showing characteristics of phase and frequency of an input/output signal of the control block shown in FIG. 78. FIGS. 81 and 82 are explanatory diagrams for obtaining the frequency characteristics shown in FIGS. 79 and 80, wherein: FIG. 81 is a diagram showing a state in which an extremum and a zero point on a real axis of a complex open plane are set to be symmetrical with respect to an imaginary axis; and FIG. 82 is a diagram showing a state in which positive and negative extrema and zero points on a real axis of a complex open plane are set to be symmetrical with respect to an imaginary axis. FIG. 83 is a block diagram showing a filter section included in the first control block shown in FIG. 78.

With the present embodiment, when performing shift control of the bending portion 14 from the distal end-side link members 21a to the proximal end-side link members 21a, instead of management by time, it is possible to control shift operations to be performed faster or slower depending on the frequency of the operation command value signal. In other words, a phase in a frequency range of the operation command value signal sequentially transmitted from the distal end-side to the proximal end-side is realized through shifting.

As shown in FIG. 78, a controller 5 according to the present embodiment includes a command control section 5A and first to nth actuator control blocks 31a1 to 31an in the same manner as in the fifth embodiment. In the same manner as the connection mode shown in FIG. 71, a plurality of first to nth control blocks 441A1 to 441An (hereinafter also collectively referred to as control block 441) are provided at the first to nth actuator control blocks 31a1 to 31an.

The first to nth control blocks 441A1 to 441An respectively include a filter section 454 (refer to FIG. 83) for shifting the phase of an inputted actuator control command signal.

The filter section 454 has filter characteristics in that gain of input/output signals is constant and output is provided having a preset phase lag. More specifically, as shown in FIG. 83, by performing computational processing using a rational function (S−P/S+P, where S represents a Laplace operator and P represents an extremum (zero point)) of a complex open plane on an input signal, the filter section 454 obtains an output signal whose gain is constant and which has a preset phase lag.

In other words, as shown in FIG. 79, a gain G of an input/output signal of each control block 441 is not dependent on a frequency f of the signal and is uniform. When each input/output signal has a phase lag, the phase lag P0 of the input/output signals is, as shown in FIG. 80, not dependent on a frequency f of the signal and is uniform.

Therefore, as shown in FIG. 81, by setting an extremum ○ and a zero point X on the real axis (real) to be symmetrical with respect to the imaginary axis (imag) on a complex open plane, or, as shown in FIG. 82, by setting an extremum ○ and a zero point X on positive/negative (+−) real axes (real) to be symmetrical with respect to the imaginary axis (imag) on a complex open plane, frequency characteristics such as those shown in FIGS. 79 and 80 may be obtained.

Therefore, by using such frequency characteristics, the filter section 454 will acquire filter characteristics in that gain of input/output signals is constant and output is provided having a preset phase lag.

Consequently, with the controller 5 shown in FIG. 78, by using a phase lag of an input/output signal from the filter section 454 of each of the first to nth control blocks 441A1 to 441An instead of using a sample and hold time used in the fifth embodiment, shift control of a plurality of link members 21a can be performed in the same manner as in the fifth embodiment.

Figure 84:
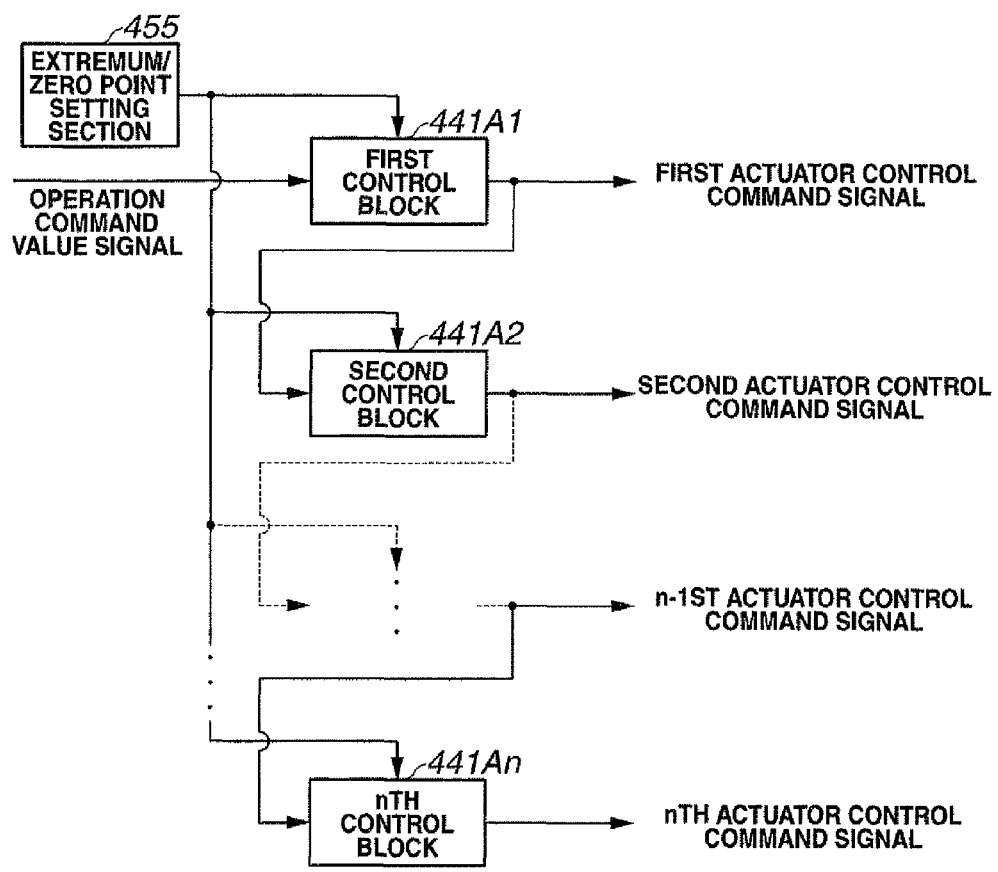
FIG. 84 is a block diagram showing a first variation of the sixth embodiment.

As illustrated by the first variation shown in FIG. 84, the sixth embodiment may be configured so that an extremum/zero point setting section 455 is provided as a phase changing section capable of adjusting and setting a phase lag quantity of an input/output signal from the filter section 454 of each of the first to nth control blocks 441A1 to 441An.

In this case, as shown in FIGS. 81 and 82, the extremum/zero point setting section 455 varies the phase lag quantity of output signals of the first to nth control blocks 441A1 to 441An by changing and setting an extremum and a zero point that determine filter characteristics of the filter section 454.

Consequently, when performing shift control of the bending portion 14 from the distal end-side towards the proximal end-side link members 21a using the phase lag, it is possible to perform control so as to extend or delay the shift travel time by varying the phase lag quantity.

With the endoscope apparatus 1 according to the sixth embodiment, while the plurality of link members 21a constituting the bending portion 14 performs bending movements so that an angle of the distal end-side link member 21a1 sequentially shifts to the proximal end-side link members 21a2 to 21an each preset phase lag quantity, the phase lag quantity can be changed arbitrarily. In addition, an arbitrary link member 21a (also referred to as an object axis) that changes the phase lag quantity can also be designated. Such a second variation of the sixth embodiment is shown in FIG. 85.

Figure 85:
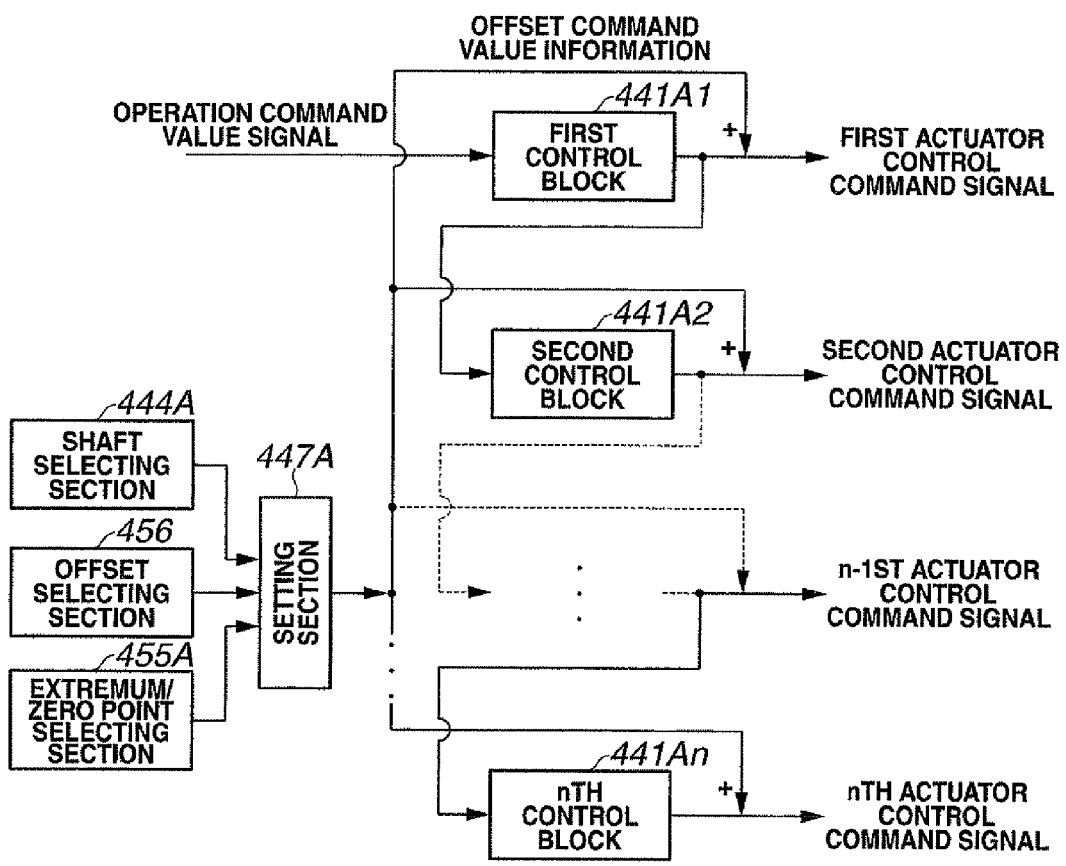
FIG. 85 is a block diagram showing a second variation of the sixth embodiment.

FIG. 85 is a block diagram showing the second variation of the sixth embodiment.

As shown in FIG. 85, a controller 5 according to the sixth variation is provided with a shaft selecting section 444A, an offset selecting section 456, and an extremum/zero point selecting section 455A.

The shaft selecting section 444A designates a shaft or, in other words, an arbitrary link member 21a whose phase lag quantity is to be changed, and outputs a designation signal to a setting section 447A. In other words, providing the shaft selecting section 444A enables selection of an arbitrary shaft (link member 21a) whose phase lag quantity is to be changed.

The offset selecting section 456 selects a quantity in which the direction of the link member 21a selected by the shaft selecting section 444A or the link member 21a that is preset by the operation command section 7 is to be changed, and outputs an offset command value signal to the setting section 447A. In other words, by providing the offset selecting section 456, when changing the direction of the designated link member 21a, it is now possible to perform adjustment by subtly changing (offsetting) the direction of the designated link member 21a by only the quantity based on the offset command value signal.

The extremum/zero point selecting section 455A is capable of arbitrarily setting a phase lag quantity of output signals of the first to nth control blocks 441A1 to 441An by changing and setting an extremum and a zero point that determine filter characteristics of the filter section 454, and outputs a set setting signal to the setting section 447A. In other words, by providing the extremum/zero point selecting section 455A, it is now possible to freely set a movement travel time among the respective link members 21*a* in which shifting is performed based on the phase lag of the input/output signal from the distal end-side to the proximal end-side.

For example, when performing insertion while shift control of the bending portion 14 of the insertion portion 9 is performed in a slow manner, the phase lag quantity from the filter section 454 should be set to increase by the extremum/zero point selecting section 455A. Conversely, when performing insertion while shift control of the bending portion 14 of the insertion portion 9 is performed in a speedy manner, the phase lag quantity from the filter section 454 should be set to decrease. Such settings may be made on a filter section 454 corresponding to a link member 21*a* selected by the shaft selecting section 444A. This enables shift control to be performed over a wide range.

Consequently, a designation signal from the shaft selecting section 444A, an offset command value signal from the offset selecting section 456 and a setting signal from the extremum/zero point selecting section 455A is supplied to the setting section 447A which then performs setting based on the control signals.

In other words, when a designation signal is supplied from the shaft selecting section 444A, the setting section 447A sets a link member 21*a* based on the designation signal as a link member 21*a* whose phase lag quantity is to be changed. Further, when an offset command value signal is supplied from the offset selecting section 456, the setting section 447A performs setting so that the direction of the designated link member 21*a* is changed by only the quantity based on the offset command value signal. When a setting signal from the extremum/zero point selecting section 455A is supplied, a phase lag quantity of a relevant filter section 454 is set so as to match a phase lag quantity based on the setting signal.

Consequently, according to the second variation, in addition to achieving the same advantageous effects as the sixth embodiment, it is now possible to arbitrarily set a time of movement due to a phase lag quantity of the respective link members 21*a* in which the angle of the distal end-side link member 21*a*1 is sequentially shift-controlled towards proximal end-side link members 21*a*2 to 21*an*. It is also possible to arbitrarily set a phase lag quantity and to arbitrarily set an offset quantity of the designated link member 21*a*. Consequently, it is now possible to perform optimum shift control in accordance with an insertion state, and insertability can be further enhanced.

In the second embodiment 2, in addition to designating a link member 21*a* whose phase lag quantity is to be changed, the shaft selecting section 444A may be arranged to also designate a link member 21*a* (also referred to as an object axis) from which shifting of an angle is commenced using a phase lag quantity.

Figure 86:
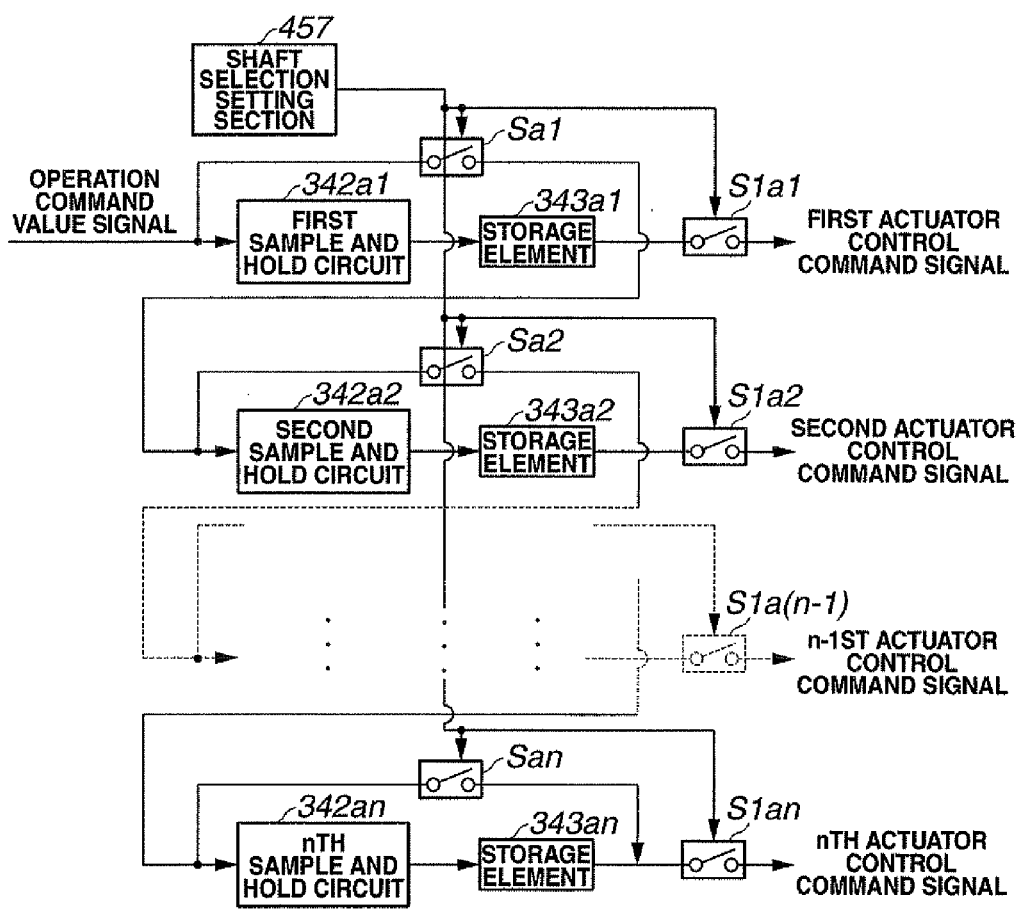
FIG. 86 relates to a seventh embodiment of the present invention and is a block diagram showing an overall configuration of a servo controller provided at each actuator control block.
Figure 87:
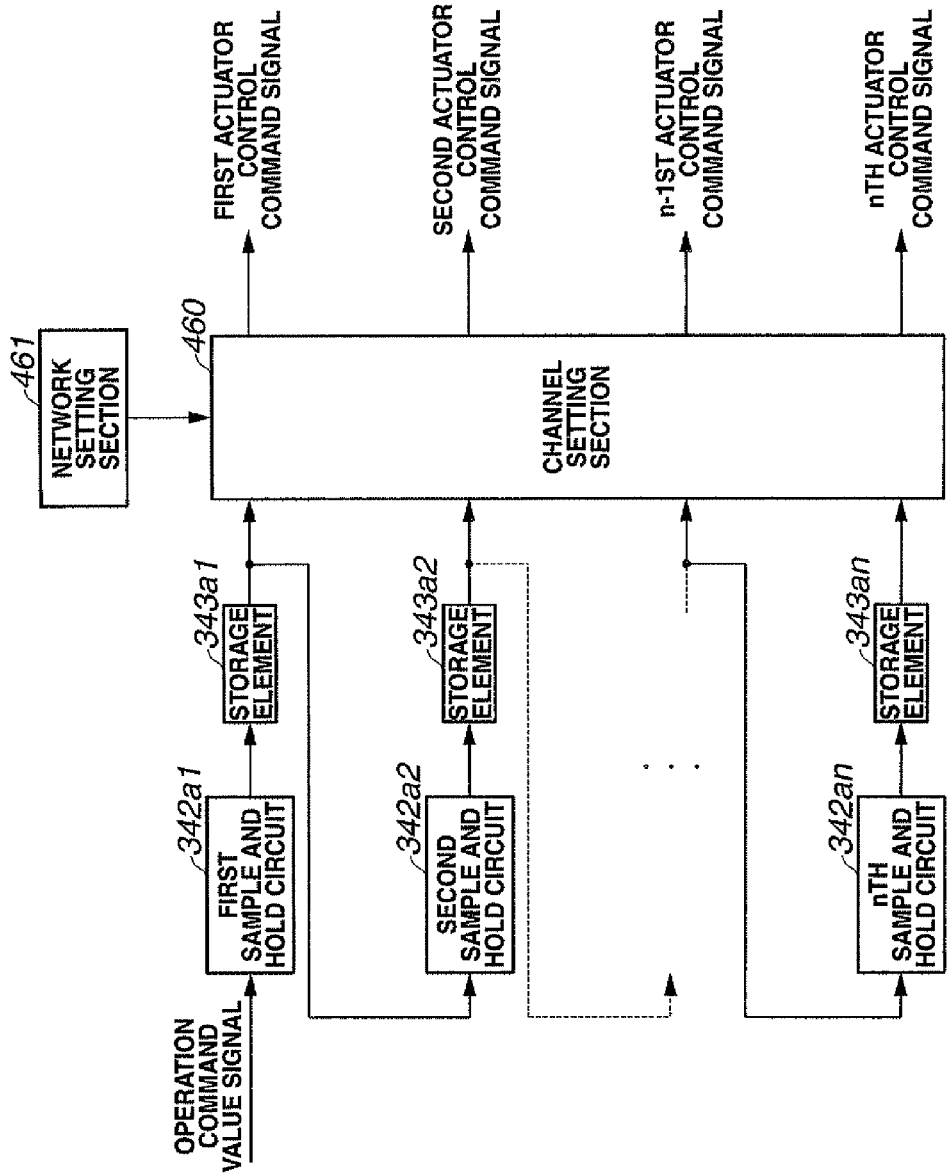
FIG. 87 represents a variation of the seventh embodiment and is a block diagram showing an overall configuration of a servo controller provided with setting section for setting a shift pathway.

FIG. 86 is a block diagram showing an overall configuration of a servo controller provided at each actuator control block, according to a seventh embodiment of the present invention. FIGS. 87 to 91 present a variation of the seventh embodiment, wherein: FIG. 87 is a block diagram showing an overall configuration of a servo controller provided with setting section for setting a shift pathway; FIG. 88 is an explanatory diagram for explaining channels settable by a channel setting section shown in FIG. 87; FIG. 89 is a diagram showing an example of an input/output signal of the channel setting section; FIG. 90 is a diagram showing a replacement matrix used during channel setting by the channel setting section; and FIG. 91 is a diagram showing an example of a channel setting set by the channel setting section.

An endoscope apparatus 1 according to the seventh embodiment is a modification of the endoscope apparatus according to the fifth embodiment and is capable of designating a link member 21*a* from which shift control is to be commenced, and is configured so that an arbitrary link member 21*a* that shifts the angle of the designated link member 21*a* is selectable.

As shown in FIG. 86, the overall configuration of the servo controller 36A according to the present embodiment is approximately the same as the block configuration shown in FIG. 71, with the exception of the servo controller 36A according to the present embodiment being provided with a shaft selection setting section 457 and a plurality of switches Sa1 to San and S1*a*1 to S1*an* provided at each sample and hold circuit 342 (342*a*1 to 342*an*).

More specifically, an operation command value signal inputted to the first sample and hold circuit 342*a*1 is supplied to the subsequent-stage second sample and hold circuit 342*a*2 and the switch Sa2 via the switch Sa1.

The switch S1*a*1 is provided on the output side of a storage element 343*a*1, and when the switch S1*a*1 is switched on, an output signal from the first sample and hold circuit 342*a*1 is outputted as a first actuator control command signal via the storage element 343*a*1.

An operation command value signal inputted to the second sample and hold circuit 342*a*2 is supplied to the subsequent-stage third sample and hold circuit 342*a*3 (not shown) and the switch Sa3 (not shown) via the switch Sa2.

The switch S1*a*2 is provided on the output side of a storage element 343*a*2, and when the switch S1*a*2 is switched on, an output signal from the second sample and hold circuit 342*a*2 is outputted as a second actuator control command signal via the storage element 343*a*2.

Henceforth, a switch San is connected in a similar manner to a sample and hold circuit 342*an* corresponding to a subsequent-stage link member 21*a*, and a similar switch S1*an* is also connected to the output side of a storage element 343*an* of the sample and hold circuit 342*an*.

The switch Sa1 and the switch S1*a*1 correspond to the distal end-side link member 21*a*1; the switch Sa2 and the switch S1*a*2 correspond to the subsequent-stage second link member 21*a*2; and subsequently, in the same manner, the switch San and the switch S1*an* are provided so as to correspond to the nth-stage link member 21*an*.

The shaft selection setting section 4457 sets a link member 21*a* at which shift control is to be commenced, and is also capable of setting an arbitrary link member 21*a* that shifts the angle of the set link member 21*a*. The shaft selection setting section 457 is also arranged to control switching of the switches Sa1 to San and switches S1*a*1 to S1*an* based on the set setting contents.

In this case, the shaft selection setting section 457 performs control so that the switch 5*a* corresponding to the set link member 21*a* is switched off and the switch S1*a* provided on the side of the storage element 343 corresponding to the set link member 21*a* is switched on.

Conversely, the shaft selection setting section 457 performs control so that a switch Sa corresponding to a link member 21*a* that has not been set is switched on and operation command value information is transmitted to a subsequent stage, and at the same time, a switch S1*a* provided on the side of the storage element 343 corresponding to the set link member 21*a* is switched off to suspend output of an actuator control command signal.

According to such a configuration, for example, by designating the second link member 21*a*2 as the link member 21*a* at which shift control is to be commenced and setting the fourth to nth link members 21a4 to 21an as the link member 21a that shifts the angle of the link member 21a2, the shaft selection setting section 457 can perform control so that the angle of the second link member 21a2 shifts along the fourth to nth link members 21a4 to 21an. Consequently, the insertability of the insertion portion 9 can be even more enhanced than that with the fifth embodiment.

As illustrated by the variation shown in FIG. 87, the seventh embodiment may be configured so that a channel setting section 460 to be connected to a network setting section 461 is provided at the output side of a storage element 343 corresponding to each link member 21a, and an order in which shift control is to be performed is changed by the channel setting section 460 based on a setting signal set by the network setting section 461.

In this case, the channel setting section 460 changes an output pathway (also referred to as a channel) of an output signal of each storage element 343a1 to 343an based on a setting signal set by the network setting section 461 or, in other words, a setting signal indicating an order in which shift control is to be performed.

For example, as shown in FIG. 88, assuming that input 1 is an output signal of the first sample and hold circuit 342a1, the channel setting section 460 is capable of arranging input 1 to be outputted by any of output 1 that is a first actuator control command signal, output 2 that is a second actuator control command signal, and output 3 that is a third actuator control command signal. In the same manner, the channel setting section 460 is capable of arranging input 2 to be outputted by any of output 1 that is the first actuator control command signal, output 2 that is the second actuator control command signal, and output 3 that is the third actuator control command signal. Henceforth, in a similar manner, input 3, . . . , input n can also be outputted via any of the output pathways (channels).

In other words, with the channel setting section 460, in the case where software for changing an output pathway is used, the channel can be changed by using a replacement matrix as shown in FIG. 90 based on a setting signal from the network setting section 461.

By using matrix computation on a replacement matrix, channel switching is now possible without having to perform special processing.

In the case of the replacement matrix shown in FIG. 90, channels of input/output signals such as those shown in FIG. 89 are realized. FIG. 91 shows an example of a channel setting set by the channel setting section 460.

As shown, by performing a computation that combines replacement matrices, arbitrary channel setting becomes possible.

Consequently, according to the present variation, by providing the network setting section 461 and the channel setting section 460, output pathways (channels) of input/output signals can be set arbitrarily. As a result, an order in which shifting is to be performed can now be changed in a simple and easy manner.

Figure 92:
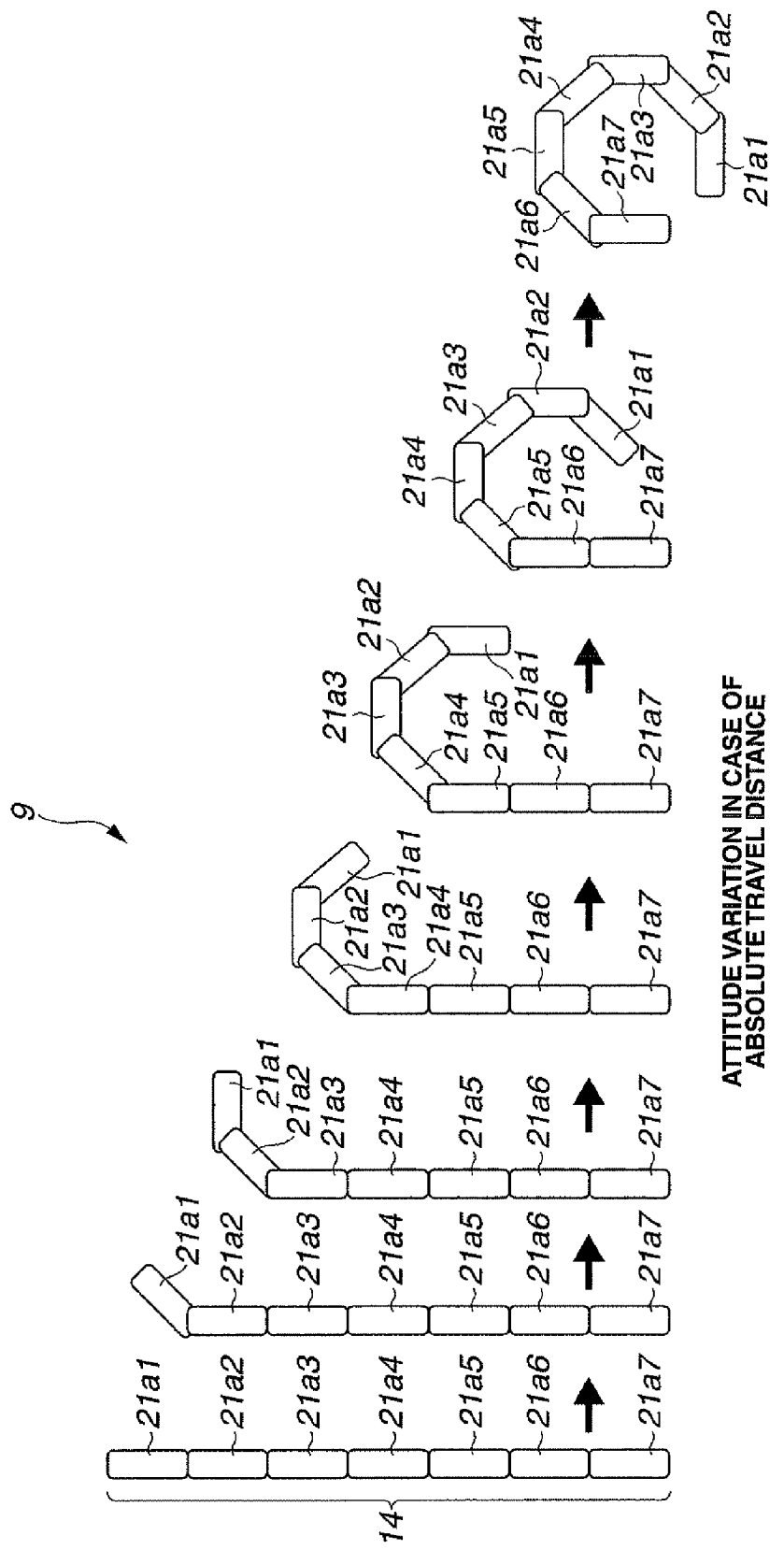
FIG. 92 is an explanatory diagram for explaining basic shifting control according to the fourth embodiment of the present invention.
Figure 93:
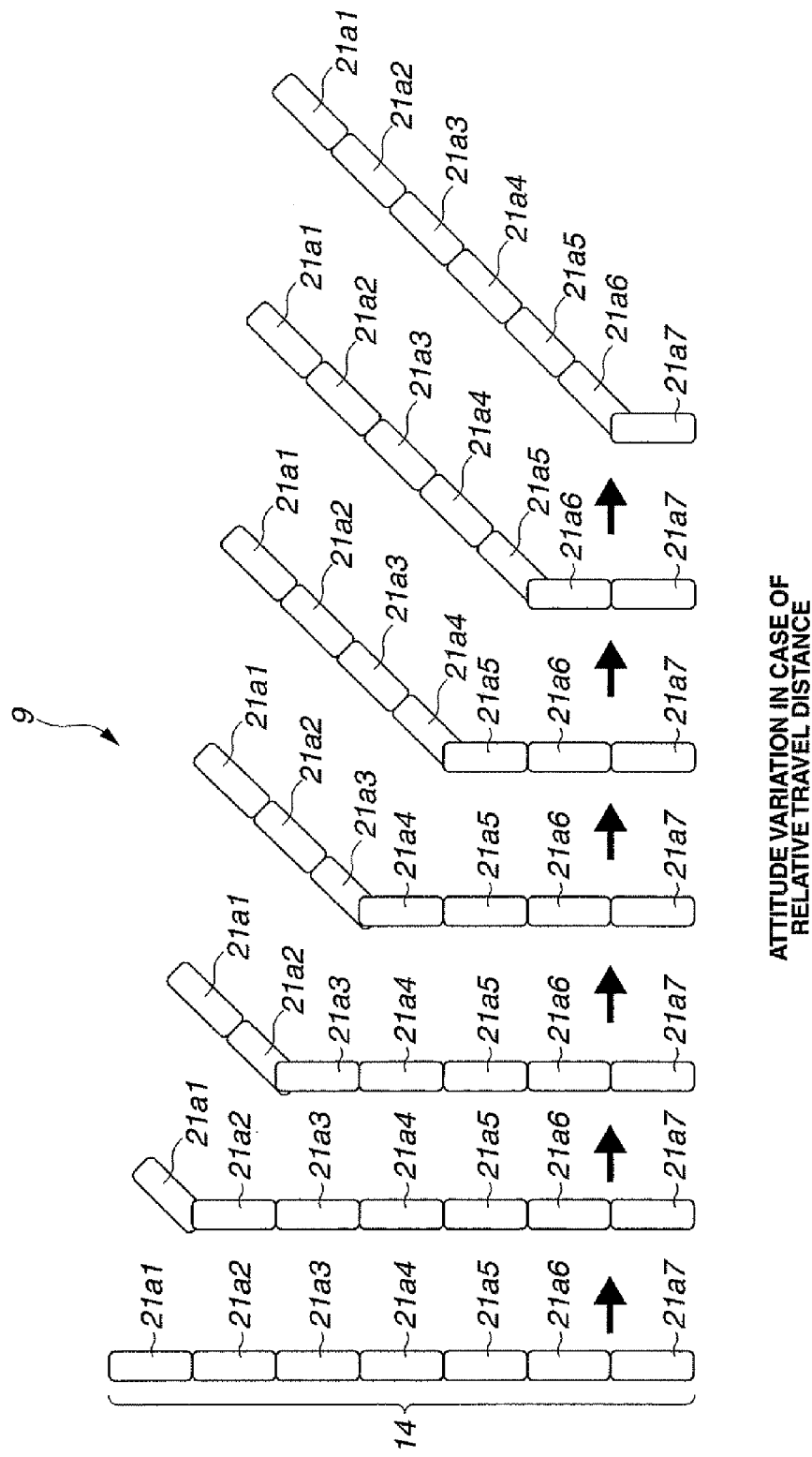
FIG. 93 relates to an eighth embodiment and is an explanatory diagram for explaining shifting control based on relative displacement.
Figure 94:
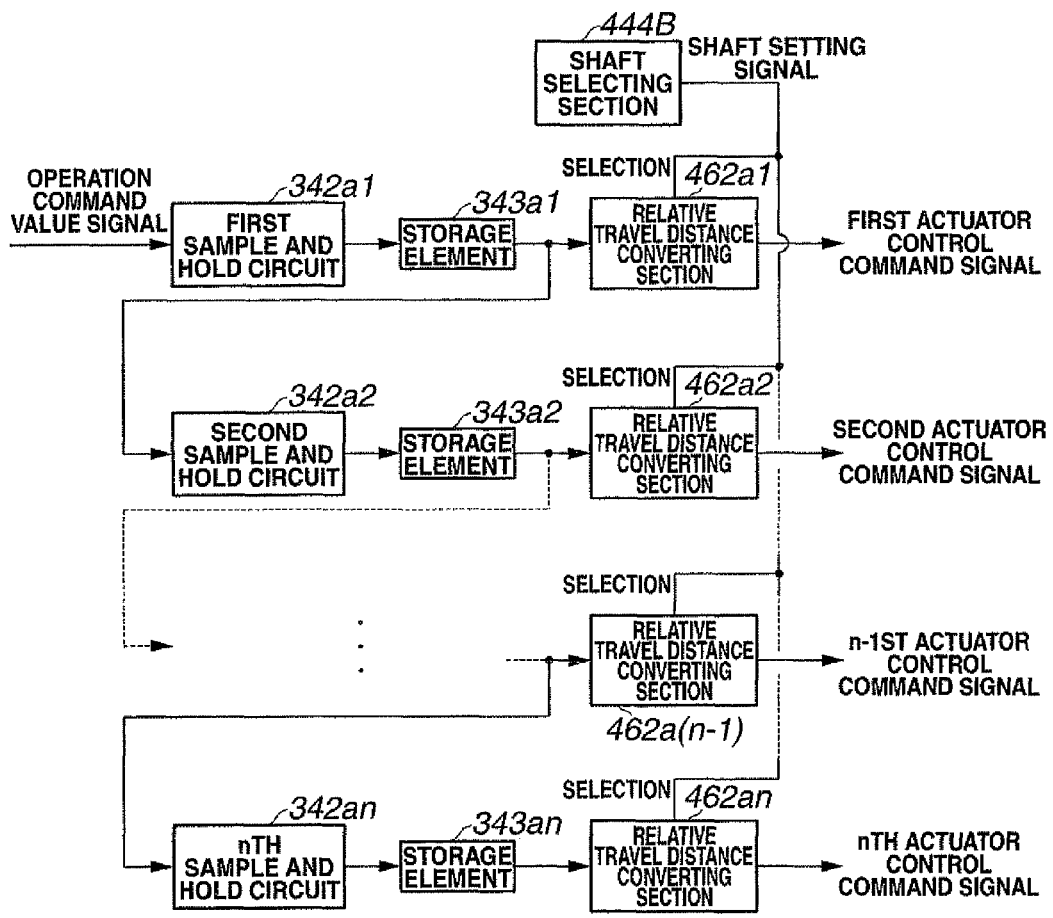
FIG. 94 relates to the eighth embodiment and is a block diagram showing an overall configuration of a servo controller provided at each actuator control block.
Figure 95:
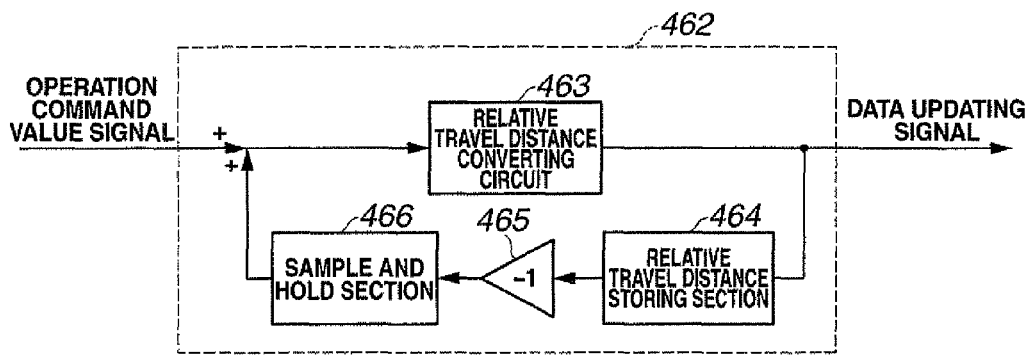
FIG. 95 relates to the eighth embodiment and is a block diagram showing a specific configuration of the relative displacement converting section shown in FIG. 94.
Figure 96:
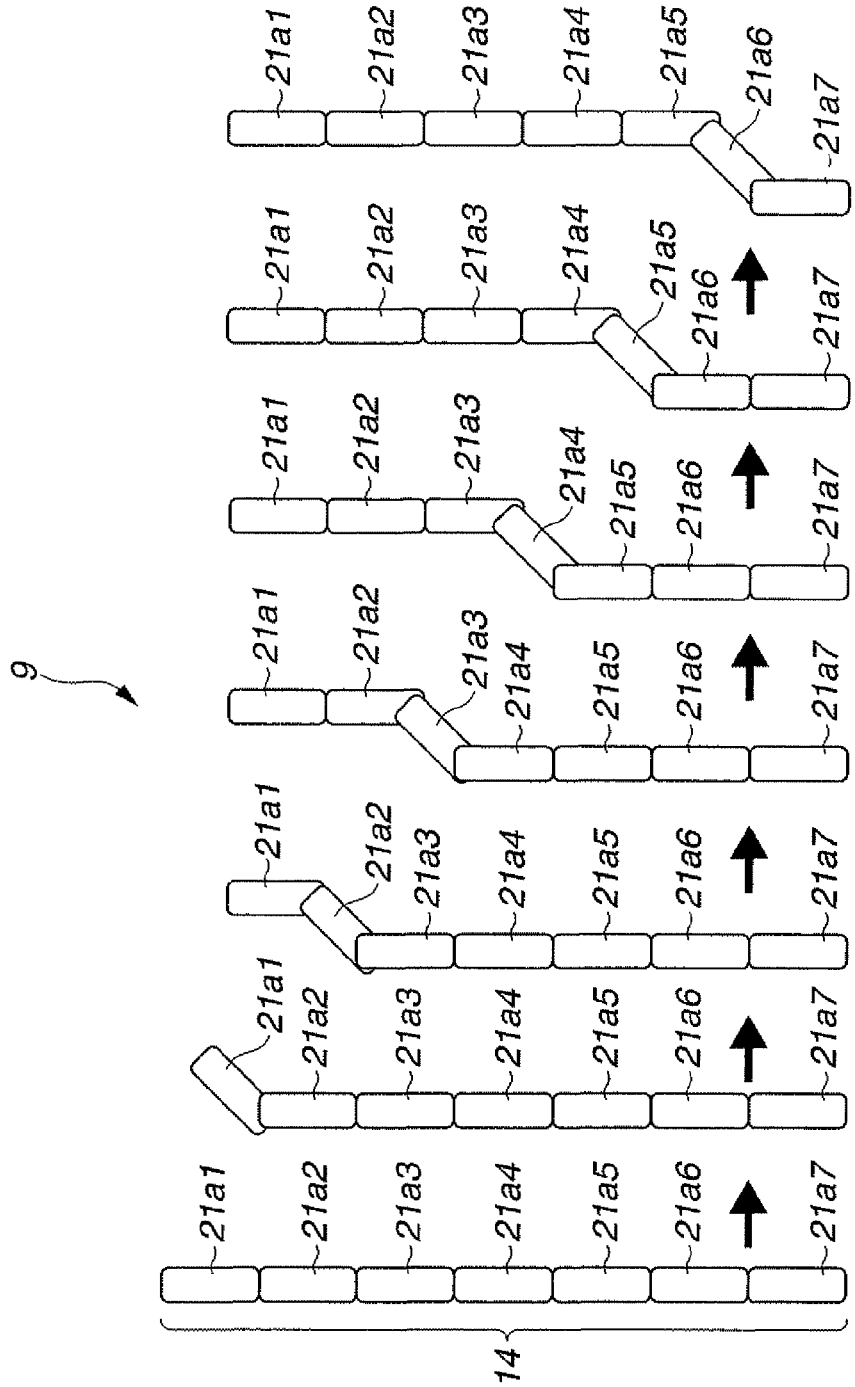
FIG. 96 represents a first variation of the eighth embodiment and is an explanatory diagram for explaining another shifting control based on relative displacement.
Figure 97:
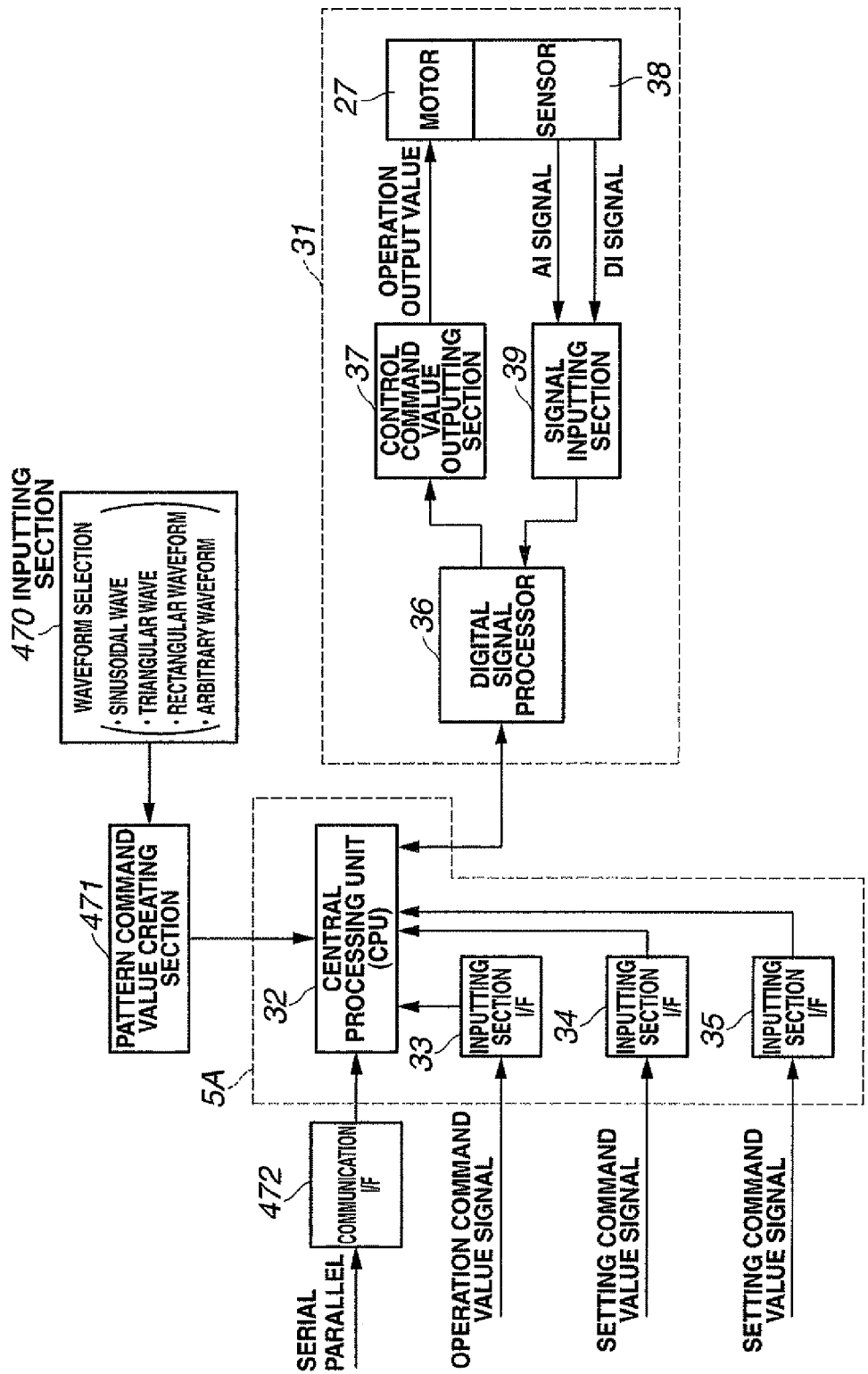
FIG. 97 is a block diagram showing a second variation of the eighth embodiment.

FIGS. 92 to 94 relate to an eighth embodiment of the present invention, wherein: FIG. 92 is an explanatory diagram for explaining basic shifting control; FIG. 93 is an explanatory diagram for explaining shifting control based on relative displacement according to the eighth embodiment; and FIG. 94 is a block diagram showing an overall configuration of a servo controller provided at each actuator control block according to the eighth embodiment. FIG. 95 is a block diagram showing a specific configuration of the relative displacement converting section shown in FIG. 94. FIG. 96 represents a first variation of the eighth embodiment, and is an explanatory diagram for explaining another shifting control based on relative displacement; and FIG. 97 represents a second variation of the eighth embodiment and is a block diagram showing an overall configuration of a controller 5 and peripheral devices of the controller 5.

The endoscope apparatus 1 according to the present invention is arranged so that an angle of a designated link member 21a is sequentially shift-controlled along subsequent stage-side link members 21a. Let us now assume that, for example, the angle of the distal end-side link member 21a1 is 45 degrees and that the angle of 45 degrees is sequentially shift-controlled along subsequent stage-side link members 21a2 to 21a7. Since the angle of 45 degrees that is to be shifted is an absolute travel distance, in the event that the angle of 45 degrees reaches the most proximal end-side link member 21a7, the attitude of the bending portion 14 will change in a procedure such as that shown in FIG. 92. In other words, simply performing shift control causes the bending portion 14 to perform bending movements which result in assuming the attitude such as that shown in FIG. 92. As a result, when performing operation, the links assume a coiled shape that is quite possibly an attitude that may inflict a burden on the patient inside a body cavity.

Therefore, for the purpose of further enhancing the insertability of the insertion portion 9 while considering the bending attitude of the bending portion 14, in addition to the absolute travel distance described earlier, the present embodiment also enables angles of the respective link members 21a to be controlled based on relative travel distances obtained based on angular displacements of link members 21a along which an angle is to be shifted.

More specifically, as shown in FIG. 94, the overall configuration of a servo controller 36A according to the present embodiment is approximately similar to the block configuration shown in FIG. 71 according to the fifth embodiment with the exception of the servo controller 36A according to the present embodiment being provided with a shaft selecting section 444B and a plurality of relative travel distance converting sections 462a1 to 462an respectively provided on the output side of a plurality of storage elements 343a1 to 343an corresponding to the plurality of link members 21a.

The shaft selecting section 444B is capable of respectively controlling the on/off states of the plurality of relative travel distance converting sections 462a1 to 462an. The shaft selecting section 444B is also capable of designating a link member 21a that performs shift control based on an absolute travel distance (hereinafter referred to as the absolute travel distance shift mode) similar to the fifth embodiment and which is shown in FIG. 92, and a ink member 21a that performs shift control based on an relative travel distance, to be described later (hereinafter referred to as the relative travel distance shift mode).

In other words, as for a link member 21a designated so as to execute the absolute travel distance shift mode, the shaft selecting section 444B switches off a relative travel distance converting section 462 on a corresponding output pathway, and causes an output signal from a storage element 463 to be outputted without modification as an actuator control command signal. On the other hand, as for a link member 21a designated so as to execute the relative travel distance shift mode, the shaft selecting section 444B switches on a relative travel distance converting section 462 on a corresponding output pathway, applies relative travel distance conversion processing on an output signal from a storage element 343, and causes the same to be outputted as an actuator control command signal.

The on/off state of the relative travel distance converting section 462 is controlled by the shaft selecting section 444B, and the relative travel distance converting section 462 is, for example, a differential circuit that applies relative travel distance conversion processing on an actuator control signal that is an input signal.

A specific configuration of the relative travel distance converting section 462 (relative travel distance converting sections 462a1 to 462an) is shown in FIG. 94.

As shown in FIG. 94, the relative travel distance converting section 462 includes: a relative travel distance converting circuit 463 that acquires a command value signal from a storage element 343 and calculates an angular relative travel distance (relative displacement) with respect to the command value signal; a relative travel distance storing section 464 that temporarily stores and outputs an output signal of the relative travel distance converting circuit 463; a converting section 465 that converts the relative travel distance from the relative travel distance storing section 464 into the opposite direction; and a sample and hold circuit 466 that samples the output signal of the converting section 465 over a set sampling time and feeds back the same to the relative travel distance converting circuit 463.

In other words, switching on the relative travel distance converting section 462 causes a corresponding link member 21a to be controlled so as to first rotationally move by an angle based on an operation command value signal, and then rotationally move by an angle that is the traveled relative travel distance (relative displacement) so as to return to its original angle.

For example, assuming that the relative travel distance shift mode has been designated for all link members 21a by the shaft selecting section 444B, the relative travel distance converting sections 462a1 to 462an shown in FIG. 94 are switched on. As a result, at the bending portion 14, as shown in FIG. 93, the distal end-side link member 21a1 first rotationally moves by an angle based on an operation command value signal as described above and then returns to its original angle. Subsequently, at the same time the angle is transmitted to the second-stage side, the second-stage link member 21a2 moves in a similar manner. Henceforth, subsequent-stage link members 21a3 to 21a7 sequentially move in a similar manner. In other words, the bending portion 14 performs bending movements as though the angle of the distal end-side link member 21a1 migrates without modification towards the proximal end-side.

Therefore, according to the present embodiment, appropriately designating a link member 21a that executes the absolute travel distance shift mode and a link member 21a that executes the above-mentioned relative travel distance shift mode by the shaft selecting section 444B enables bending movements more suited an object member can be performed. As a result, the insertability of the insertion portion 9 can be further enhanced.

With the present embodiment, by modifying the relative travel distance converting section 462, as illustrated by the first variation shown in FIG. 96, it is also possible to have the bending portion 14 perform bending movements (locomotion movement) as though a link member 21a that has rotationally moved by an angle based on an operation command value signal sequentially performs parallel translation towards the proximal end-side.

In addition, the present embodiment may be configured so that, as means for instructing the execution of a bending movement pattern of the bending portion 14, instead of operation by the operation command section 7 such as a joystick, as illustrated by the second variation shown in FIG. 97, "automatic control by a preset operation pattern" may be performed by providing an inputting section 470 and a pattern command value creating section 471.

In other words, as shown in FIG. 97, an endoscope apparatus 1 according to the second variation is further provided with: the inputting section 470 that is an inputting I/F that selects what bending movement waveform will be employed when performing shift control of a designated angle; the pattern command value creating section 471 that creates a pattern signal based on the bending movement waveform selected by the inputting section 470 and outputs the same to the CPU 32 shown in FIG. 10; and a communication I/F 472 connected to the CPU 32 and which is capable of communicating with other operation devices in a hospital or with a communication device for performing a remote operation from outside of the hospital.

For example, when sinusoidal wave is selected by the inputting section 470, the bending portion 14 will perform bending movements such that the designated angle sequentially shifts as though a sinusoidal wave. When triangular wave is selected by the inputting section 470, the bending portion 14 will perform bending movements such that the designated angle sequentially shifts as though tracing the respective sides of a triangle. When rectangular wave is selected by the inputting section 470, the bending portion 14 will perform bending movements such that the designated angle sequentially shifts as though a rectangular wave. An arbitrary waveform other than those described above may be inputted at the inputting section 470.

Consequently, by selecting and setting in advance a bending movement waveform for creating an optimum bending movement pattern in accordance with a procedure, the operator will be able to automatically perform shift control of the bending portion 14 in an optimum bending movement pattern in accordance with a procedure without operating the operation command section 7 such as a joystick. As a result, the insertability of the insertion portion 9 can be further enhanced.

For the embodiments according to the present invention, while the bending portion 14 having the insertion portion driving mechanism constituting a manipulator has been described as being provided at the insertion portion 9 of the endoscope 2, the bending portion 14 may be arranged to be provided at an insertion portion of an endoscope insertion aiding device that aids the insertion of the insertion portion 9 into a tube cavity by allowing insertion of the insertion portion 9 of the endoscope 2.

As seen, for the present embodiment, while descriptions on planar movements has been given for simplicity, in an endoscope, it is obvious that the descriptions shall translate to configurations for performing movements in three-dimensional space.

The present invention is not limited to the respective embodiments and variation thereof described above, and various modifications can be made without departing from the gist of the present invention. It is needless to say that the respective embodiments and variation thereof described above may be combined as appropriate.

What is claimed is:
1. A medical control apparatus comprising:
a bending portion, provided to a distal end side of an insertion portion of a medical device, comprising a plurality of link members which can be brought into a straight state and which are consecutively provided so as to be rotationally movable;

a driving section adapted to drive bending movements of the bending portion by rotationally moving the plurality of link members;

a designating section adapted to designate at least one of the plurality of link members;

a control section adapted to compute respective angles of the plurality of link members, and to control the driving section to rotationally move the plurality of link members based on the computation results; and a setting section adapted to set a parameter to prevent angles formed between the adjacent link members among the plurality of link members from assuming an acute angle exceeding a preset moveable range when computing the angles formed between respective adjacent link members, and to inhibit the bending movements by the driving section as the angles formed between the adjacent link members approaches the limit of the moveable range, wherein the designating section designates positions and orientations of the link members at a distal most end side in the plurality of link members, and wherein the control section:

obtains a coordinate position of the link member at a distal most end side in a predetermined two or three dimensional space at the time the link member at the distal most end side in the plurality of link members was designated, obtains a direction of the link member at the distal most end side in the obtained coordinate position, and controls the driving section based on the obtained coordinate position of the link member at the distal most end side, the obtained direction of the link member at the distal most end side at the obtained coordinate position, and the parameter set by the setting section, such that respective angles of the plurality of link members are computed so that other link members contiguous to the link member at the distal most end side are oriented in the obtained direction when the other link members pass through the obtained coordinate position and the plurality of link members are rotationally moved based on the computation results, by performing computation to determine the positions of the link members at the distal most end side by decomposing a matrix space that shows a dynamic relationship between an acceleration of the positions of the link members at the distal most end side and an acceleration of each of the plurality of link members into a kernel space and a null space, when solving kinematics of a restraint condition of each of the link members.

2. The medical control apparatus according to claim 1, comprising:

a first detecting section that detects angles mutually formed by the plurality of link members and displacements of the angles, wherein the control section uses a detection result by the first detecting section to compute respective angles formed by adjacent link members among the plurality of link members, and based on the computation result, controls the driving section so as to rotationally move the plurality of link members.

3. The medical control apparatus according to claim 1, wherein the link members designated by the designating section include at least a most distal end-side link member and a link member other than the most distal end-side link member, from the plurality of link members.

4. The medical control apparatus according to claim 1, wherein the designating section includes changing section that changes the position or the direction of a link member designated by the designating section by only a preset quantity.

5. The medical control apparatus according to claim 1, wherein the control section causes all or a part of the plurality of link members to freely rotationally move by suspending driving by the driving section.

6. The medical control apparatus according to claim 5, wherein the designating section includes selecting section for selecting a link member to be freely rotationally moved, and the control section causes only the link member selected by the selecting section to be freely rotationally movable.

7. The medical control apparatus according to claim 1, comprising: a second detecting section that detects forces respectively applied to the plurality of link members for each link member, wherein the control section uses a detection result by the second detecting section to change the parameter, computes respective angles formed by adjacent link members among the plurality of link members based on the changed parameter, and based on the computation result, controls the driving section so as to rotationally move the plurality of link members.

8. The medical control apparatus according to claim 1, comprising:

a first detecting section that detects angles mutually formed by the plurality of link members and displacements of the angles, wherein the control section changes the parameter according to a detection result by the first detecting section, computes respective angles formed by adjacent link members among the plurality of link members based on the changed parameter, and based on the computation result, controls the driving section so as to rotationally move the plurality of link members.

9. The medical control apparatus according to claim 1, wherein the plurality of link members are respectively connected to a plurality of bending operation wires consecutively so as to be respectively rotationally movable at a distal end-side of the insertion portion to be inserted into a subject to be examined, the driving section causes bending movements of the bending portion by respectively rotationally moving the plurality of link members by respectively pulling or relaxing the bending operation wires, and the designating section designates a position and a direction of a most distal end-side link member of the insertion portion among the plurality of link members.

10. The medical control apparatus according to claim 9, comprising:

a first detecting section that detects angles mutually formed by the plurality of link members and displacements of the angles, wherein the control section uses a detection result by the first detecting section to compute respective angles formed by adjacent link members among the plurality of link members, and based on the computation result, controls the driving section so as to rotationally move the plurality of link members.

11. The medical control apparatus according to claim 10, wherein
  when the most distal end-side link member changes to a direction that is different from the direction designated by the designating section, the control section uses a detection result by the first detecting section to compute respective angles formed by adjacent link members among the plurality of link members contiguous to the most distal end-side link member so that rotational movement is performed by just the changed quantity in the direction opposite to the direction in which the most distal end-side link member had changed, and based on the computation result, controls the driving section so as to rotationally move the plurality of link members.

12. The medical control apparatus according to claim 9, wherein
  the plurality of bending operation wires include first and second bending operation wires for respectively causing the bending portion to rotationally move in at least two directions, and
  the control section causes stiffness to occur in the bending portion by, after bending movement of the bending portion in the two directions, controlling the driving section so that a force pulling the first bending operation wire becomes equal to a force pulling the second bending operation wire.

* * * * *